United States Patent [19]
Araki et al.

[11] Patent Number: 6,004,773
[45] Date of Patent: Dec. 21, 1999

[54] METHOD FOR PRODUCING L-LYSINE

[75] Inventors: Masayuki Araki; Masakazu Sugimoto; Yasuhiko Yoshihara; Tsuyoshi Nakamatsu, all of Kawasaki, Japan

[73] Assignee: Ajinomoto Co., Inc., Tokyo, Japan

[21] Appl. No.: 08/985,908

[22] Filed: Dec. 5, 1997

[30]     Foreign Application Priority Data

Dec. 5, 1996   [JP]   Japan ..................... 8-325659

[51] Int. Cl.$^6$ .............. C12P 1/00; C12P 21/02; C12N 15/63; C07H 21/04
[52] U.S. Cl. ................. 435/41; 435/69.1; 435/106; 435/252.3; 435/252.32; 435/320.1; 536/23.1
[58] Field of Search .................... 435/41, 69.1, 106, 435/115, 320.1, 252.3, 252.32; 536/23.1

[56]           References Cited

U.S. PATENT DOCUMENTS

| 4,861,722 | 8/1989 | Sano et al. | 435/252.32 |
|---|---|---|---|
| 4,980,285 | 12/1990 | Sano et al. | 435/108 |
| 5,688,671 | 11/1997 | Sugimoto et al. | 435/115 |
| 5,804,414 | 9/1998 | Moriya et al. | 435/69.1 |

FOREIGN PATENT DOCUMENTS

| 0077548A2 | 4/1983 | European Pat. Off. . |
|---|---|---|
| 406261766A | 9/1994 | Japan . |
| 94/25605 | 11/1994 | WIPO . |
| 96/40934 | 12/1996 | WIPO . |

OTHER PUBLICATIONS

Rudinger, "Characteristics of the amino acids as components of a peptide hormone sequence. In: Peptide Hormones", Ed. J. A. Parsons, University Park Press, Baltimore, Md. pp. 1–7, 1976.

Ngo et al, "Computational complexity, protein structure prediction, and the Levinthal Paradox. In: The Protein Folding Problem and Tertiary Structure Prediction", Eds. Merz et al. Birkhauser et al. Boston, MA. pp. 491–495, 1994.

Thornton et al, Protein Engineering: Editorial Overview. Current Opinion in Biotechnology 6(4): pp. 367–369, 1995.

Wallace, "Understanding cytochrome c function: engineering protein structure by semisynthesis", The FASEB Journal, vol. 7. pp. 505–515, 1993.

Cremer et al, "Regulation of enzymes of lysine biosynthesis in *Corynebacterium glutamicum*", J. Gen. Microbiol., vol. 134, No. 12., pp. 3221–3229, 1988 (Abstract only).

PHSG299 TaKARa catalog.

ATCC No.: 13869 Organism: *Corynebacterium glutamic*.

*Primary Examiner*—Nancy Degen
*Attorney, Agent, or Firm*—Oblon, Spivak, McClelland, Maier & Neustadt, P.C.

[57]            ABSTRACT

A coryneform bacterium harboring an aspartokinase in which feedback inhibition by L-lysine and L-threonine is substantially desensitized, and comprising an enhanced DNA sequence coding for a dihydrodipicolinate reductase, an enhanced DNA sequence coding for dihydropicolinate reductase, an enhance DNA sequence coding for dihydropicolinate synthase, an enhanced DNA sequence coding for diaminopimelate decarboxylase and an enhanced DNA sequence coding for aspartate aminotransferase; a method for producing L-lysine comprising the steps of cultivating the coryneform bacterium in an appropriate medium to allow L-lysine to be produced and accumulated in a culture of the bacterium, and collecting L-lysine from the culture; and a recombinant DNA usable for production of the coryneform bacterium.

12 Claims, 13 Drawing Sheets

METHOD FOR PRODUCING L-LYSINE

BACKGROUND OF THE INVENTION

The present invention relates to a method for producing L-lysine by cultivating a microorganism obtained by modifying a coryneform bacterium used for fermentative production of amino acid or the like by means of a technique based on genetic engineering.

L-Lysine, which is used as a fodder additive, is usually produced by a fermentative method by using an L-lysine-producing mutant strain belonging to the coryneform bacteria. Various L-lysine-producing bacteria known at present are those created by artificial mutation starting from wild type strains belonging to the coryneform bacteria.

As for the coryneform bacteria, there are disclosed a vector plasmid which is autonomously replicable in bacterial cells and has a drug resistance marker gene (see U.S. Pat. No. 4,514,502), and a method for introducing a gene into bacterial cells (for example, Japanese Patent Application Laid-open No. 2-207791). There is also disclosed a possibility for breeding an L-threonine- or L-isoleucine-producing bacterium by using the techniques as described above (see U.S. Pat. Nos. 4,452,890 and 4,442,208). As for breeding of an L-lysine-producing bacterium, a technique is known, in which a gene participating in L-lysine biosynthesis is incorporated into a vector plasmid to amplify the gene in bacterial cells (for example, Japanese Patent Application Laid-open No. 56-160997).

Known genes for L-lysine biosynthesis include, for example, a dihydrodipicolinate reductase gene (Japanese Patent Application Laid-open No. 7-75578) and an aspartate aminotransferase gene (Japanese Patent Application Laid-open No. 6-102028) in which a gene participating in L-lysine biosynthesis is cloned, as well as a phosphoenolpyruvate carboxylase gene (Japanese Patent Application Laid-open No. 60-87788), a dihydrodipicolinate synthase gene (Japanese Patent Publication No. 6-55149), and a diaminopimelate decarboxylase gene (Japanese Patent Application Laid-open No. 60-62994) in which amplification of a gene affects L-lysine productivity.

As for enzymes participating in L-lysine biosynthesis, a case is known for an enzyme which undergoes feedback inhibition when used as a wild type. In this case, L-lysine productivity is improved by introducing an enzyme gene having such mutation that the feedback inhibition is desensitized. Those known as such a gene specifically include, for example, an aspartokinase gene (International Publication Pamphlet of WO 94/25605).

As described above, certain successful results have been obtained by means of amplification of genes for the L-lysine biosynthesis system, or introduction of mutant genes. For example, a coryneform bacterium, which harbors a mutant aspartokinase gene with desensitized concerted inhibition by lysine and threonine, produces a considerable amount of L-lysine (about 25 g/L). However, this bacterium suffers decrease in growth speed as compared with a bacterium harboring no mutant aspartokinase gene. It is also reported that L-lysine productivity is improved by further introducing a dihydrodipicolinate synthase gene in addition to a mutant aspartokinase gene (*Applied and Environmental Microbiology*, 57(6), 1746–1752 (1991)). However, such a bacterium suffers further decrease in growth speed.

As for the dihydrodipicolinate reductase gene, it has been demonstrated that the activity of dihydrodipicolinate reductase is increased in a coryneform bacterium into which the gene has been introduced, however, no report is included for the influence on L-lysine productivity (Japanese Patent Application Laid-open No. 7-75578).

In the present circumstances, no case is known for the coryneform bacteria, in which anyone has succeeded in remarkable improvement in L-lysine yield without restraining growth by combining a plurality of genes for L-lysine biosynthesis. No case has been reported in which growth is intended to be improved by enhancing a gene for L-lysine biosynthesis as well.

SUMMARY OF THE INVENTION

An object of the present invention is to improve the L-lysine productivity of a coryneform bacterium by using genetic materials of DNA sequences each coding for aspartokinase (hereinafter referred to as "AK", provided that a gene coding for an AK protein is hereinafter referred to as "lysC", if necessary), dihydrodipicolinate reductase (hereinafter referred to as "DDPR", provided that a gene coding for a DDPR protein is hereinafter referred to as "dapB", if necessary), dihydrodipicolinate synthase (hereinafter abbreviate as "DDPS", provided that a gene coding for a DDPS protein is hereinafter referred to as "dapA", if necessary), diaminopimelate decarboxylase (hereinafter referred to as "DDC", provided that a gene coding for a DDC protein is hereinafter referred to as "lysA", if necessary), and aspartate aminotransferase (hereinafter referred to as "AAT", provided that a gene coding for an AAT protein is hereinafter referred to as "aspC", if necessary) which are important enzymes for L-lysine biosynthesis in cells of coryneform bacteria.

The principle of the present invention is based on the fact that the L-lysine productivity can be improved by enhancing mutant lysC (hereinafter simply referred to as "imutant lysC", if necessary) coding for mutant AK (hereinafter simply referred to as "mutant AK", if necessary) in which concerted inhibition by lysine and threonine is desensitized, dapA, dapB, lysA and aspC in combination.

Namely, the present invention provides a recombinant DNA autonomously replicable in cells of coryneform bacteria, comprising a DNA sequence coding for an aspartokinase in which feedback inhibition by L-lysine and L-threonine is substantially desensitized, a DNA sequence coding for a dihydrodipicolinate reductase, a DNA sequence coding for dihydrodipicolinate synthase, a DNA sequence coding for diaminopimelate decarboxylase, and a DNA sequence coding for aspartate aminotransferase.

In another aspect, the present invention provides a coryneform bacterium harboring an aspartokinase in which feedback inhibition by L-lysine and L-threonine is substantially desensitized, and comprising an enhanced DNA sequence coding for a dihydrodipicolinate reductase, an enhanced DNA sequence coding for dihydropicolinate reductase, an enhance DNA sequence coding for dihydropicolinate synthase, an enhanced DNA sequence coding for diaminopimelate decarboxylase and an enhanced DNA sequence coding for aspartate aminotransferase.

In still another aspect, the present invention provides a method for producing L-lysine comprising the steps of cultivating any one of the coryneform bacteria described above in an appropriate medium, to allow L-lysine to be produced and accumulated in a culture of the bacterium, and collecting L-lysine from the culture.

The present invention also provides a DNA coding for a protein comprising an amino acid sequence shown in SEQ ID NO: 31. An example of the DNA is a DNA comprising a nucleotide sequence of nucleotide number 879 to 2174 in a nucleotide sequence shown in SEQ ID NO: 30.

The present invention further provides a vector pVK7, which is autonomously replicable in cells of *Eschericia coli* and *Brevibacterium lactofermentum*, and comprising a multiple cloning site and lacZ'.

The coryneform bacteria referred to in the present invention are a group of microorganisms as defined in *Beraev's Manual of Determinative Bacteriology*, 8th ed., p. 599 (1974), which are aerobic Gram-positive non-acid-fast rods having no spore-forming ability. The coryneform bacteria include bacteria belonging to the genus Corynebacterium, bacteria belonging to the genus Brevibacterium having been hitherto classified into the genus Brevibacterium but united as bacteria belonging to the genus Corynebacterium at present, and bacteria belonging to the genus Brevibacterium closely relative to bacteria belonging to the genus Corynebacterium.

According to the present invention, the L-lysine productivity of coryneform bacteria can be improved.

DETAILED DESCRIPTION OF THE INVENTION

Figure 1:
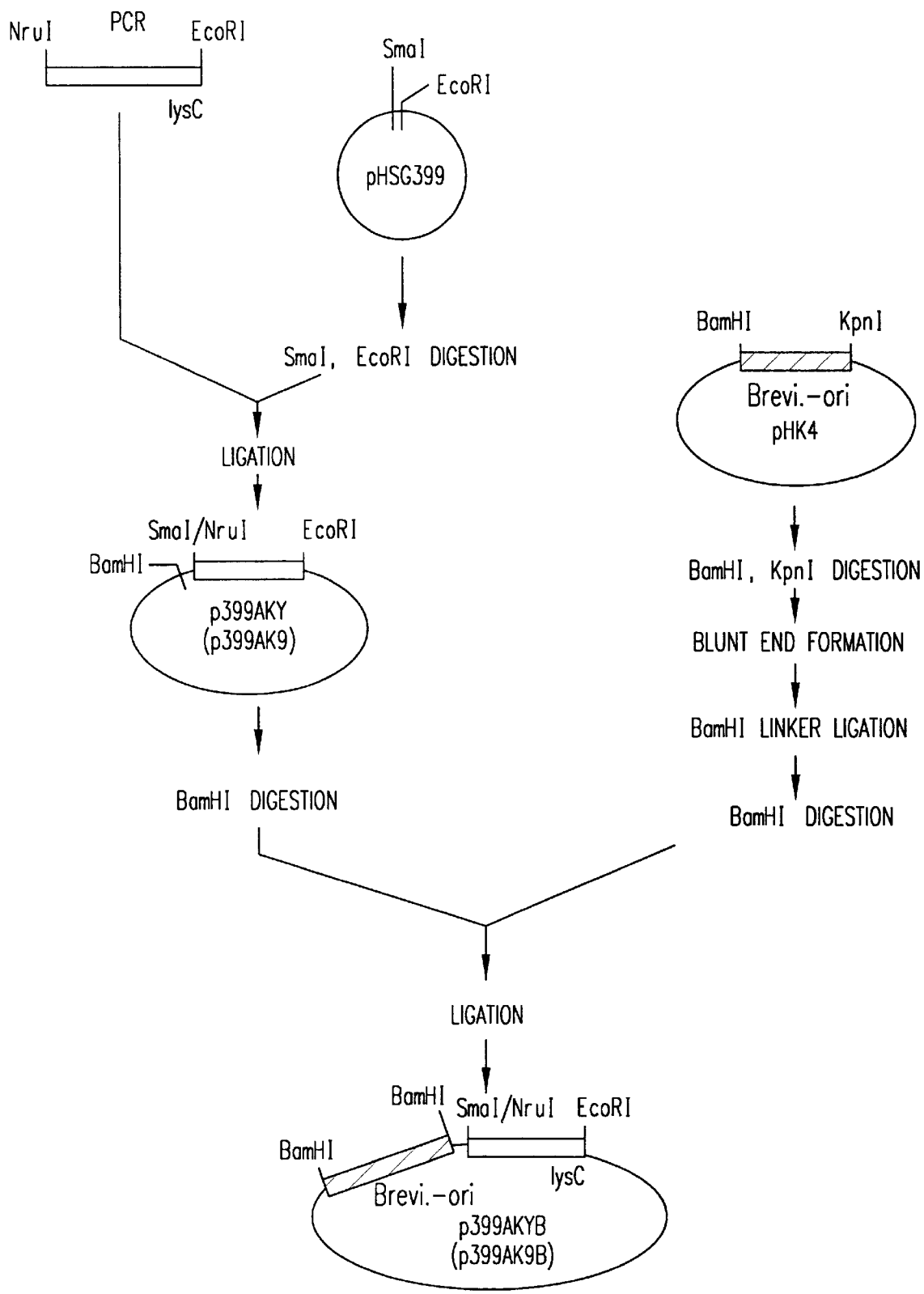
FIG. 1 illustrates a process of construction of plasmids p399AK9B and p399AKYB comprising mutant lysC.

<1>Preparation of genes for L-lysine biosynthesis used for the present invention The genes for L-lysine biosynthesis used in the present invention are obtained respectively by preparing chromosomal DNA from a bacterium as a DNA donor, constructing a chromosomal DNA library by using a plasmid vector or the like, selecting a strain harboring a desired gene, and recovering, from the selected strain, recombinant DNA into which the gene has been inserted. The DNA donor for the gene for L-lysine biosynthesis used in the present invention is not specifically limited provided that the desired gene for L-lysine biosynthesis expresses an enzyme protein which functions in cells of coryneform bacteria. However, the DNA donor is preferably a coryneform bacterium.

All of the genes of lysC, dapA, dapB and lysA originating from coryneform bacteria have known sequences. Accordingly, they can be obtained by performing amplification in accordance with the polymerase chain reaction method (PCR; see White, T. J. et al., *Trends Genet.*, 5, 185 (1989)).

Each of the genes for L-lysine biosynthesis used in the present invention is obtainable in accordance with certain methods as exemplified below.

(1) Preparation of mutant lysC

A DNA fragment containing mutant lysC can be prepared from a mutant strain in which synergistic feedback inhibition on the AK activity by L-lysine and L-threonine is substantially desensitized (International Publication Pamphlet of WO 94/25605). Such a mutant strain can be obtained, for example, from a group of cells originating from a wild type strain of a coryneform bacterium subjected to a mutation treatment by applying an ordinary mutation treatment such as ultraviolet irradiation and treatment with a mutating agent such as N-methyl-N'-nitro-N-nitrosoguanidine (NTG). The AK activity can be measured by using a method described by Miyajima, R. et al. in *The Journal of Biochemistry* (1968), 63(2), 139–148. The most preferred as such a mutant strain is represented by an L-lysine-producing bacterium AJ3445 (FERM P-1944) derived by a mutation treatment from a wild type strain of *Brevibacterium lactofermentum* ATCC 13869 (having its changed present name of *Corynebacterium glutamicum*).

Alternatively, mutant lysC is also obtainable by an in vitro mutation treatment of plasmid DNA containing wild type lysC. In another aspect, information is specifically known on mutation to desensitize synergistic feedback inhibition on AK by L-lysine and L-threonine (International Publication Pamphlet of WO 94/25605). Accordingly, mutant lysC can be also prepared from wild type lysC on the basis of the information in accordance with, for example, the site-directed mutagenesis method.

A fragment comprising lysC can be isolated from a coryneform bacterium by preparing chromosomal DNA in accordance with, for example, a method of Saito and Miura (H. Saito and K. Miura, *Biochem. Biophys. Acta*, 72, 619 (1963)), and amplifying lvsC in accordance with the polymerase chain reaction method (PCR; see White, T. J. et al., *Trends Genet.*, 5, 185 (1989)).

DNA primers are exemplified by single strand DNA's of 23-mer and 21-mer having nucleotide sequences shown in SEQ ID NOs: 1 and 2 in Sequence Listing in order to amplify, for example, a region of about 1,643 bp coding for lisC based on a sequence known for *Corynebacterium glutamicum* (see *Molecular Microbiology* (1991), 5(5), 1197–1204; *Mol. Gen. Genet.* (1990), 224, 317–324). DNA can be synthesized in accordance with an ordinary method by using DNA synthesizer model 380B produced by Applied Biosystems and using the phosphoamidite method (see *Tetrahedron Letters* (1981), 22, 1859). PCR can be performed by using DNA Thermal Cycler Model PJ2000 produced by Takara Shuzo, and using Taq DNA polymerase in accordance with a method designated by the supplier.

It is preferred that lysC amplified by PCR is ligated with vector DNA autonomously replicable in cells of *E. coli* and/or coryneform bacteria to prepare recombinant DNA, and the recombinant DNA is introduced into cells of *E. coli* beforehand. Such provision makes following operations easy. The vector autonomously replicable in cells of *E. coli* is preferably a plasmid vector which is preferably autonomously replicable in cells of a host, including, for example, pUC19, pUC18, pBR322, pHSG299, pHSG399, pHSG398, and RSF1010.

When a DNA fragment having an ability to allow a plasmid to be autonomously replicable in coryneform bacteria is inserted into these vectors, they can be used as a shuttle vector autonomously replicable in both *E. coli* and coryneform bacteria.

Such a shuttle vector includes the followings. Microorganisms harboring each of vectors and accession numbers in international deposition authorities (in parentheses) are shown.

pHC4: *Escherichia coli* AJ12617 (FERM BP-3532)

pAJ655: *Escherichia coli* AJ11882 (FERM BP-136)
Corynebacterium glutamicum SR8201 (ATCC 39135)

pAJ1844: *Escherichia coli* AJ11883 (FERM BP-137)
Corynebacterium glutamicum SR8202 (ATCC 39136)

pAJ611: *Escherichia coli* AJ11884 (FERM BP-138)

pAJ3148: Corynebacterium glutamicum SR8203 (ATCC 39137)

pAJ440: *Bacillus subtilis* AJ11901 (FERM BP-140)

These vectors are obtainable from the deposited microorganisms as follows. Cells collected at a logarithmic growth phase were lysed by using lysozyme and SDS, followed by separation from a lysate by centrifugation at 30,000×g to obtain a supernatant. To the supernatant, polyethylene glycol is added, followed by fractionation and purification by means of cesium chloride-ethidium bromide equilibrium density gradient centrifugation.

*E. coli* can be transformed by introducing a plasmid in accordance with, for example, a method of D. M. Morrison (*Methods in Enzymology*, 68, 326 (1979)) or a method in which recipient cells are treated with calcium chloride to increase permeability for DNA (Mandel, M. and Higa, A., *J. Mol. Biol.*, 53, 159 (1970)).

Wild type lysC is obtained when lysC is isolated from an AK wild type strain, while mutant lysC is obtained when lysC is isolated from an AK mutant strain in accordance with the method as described above.

An example of a nucleotide sequence of a DNA fragment containing wild type lysC is shown in SEQ ID NO: 3 in Sequence Listing. An amino acid sequence of α-subunit of a wild type AK protein is deduced from the nucleotide sequence, and is shown in SEQ ID NO: 4 in Sequence Listing together with the DNA sequence. Only the amino acid sequence is shown in SEQ ID NO: 5. An amino acid sequence of β-subunit of the wild type AK protein is deduced from the nucleotide sequence of DNA, and is shown in SEQ ID NO: 6 in Sequence Listing together with the DNA sequence. Only the amino acid sequence is shown in SEQ ID NO: 7. In each of the subunits, GTG is used as an initiation codon, and a corresponding amino acid is represented by methionine. However, this representation refers to methionine, valine, or formylmethionine.

The mutant lysC used in the present invention is not specifically limited provided that it codes for AK in which synergistic feedback inhibition by L-lysine and L-threonine is desensitized. However, the mutant lysC is exemplified by one including mutation in which an amino acid residue corresponding to a 279th alanine residue as counted from the N-terminal is changed into an amino acid residue other than alanine and other than acidic amino acid in the α-subunit, and an amino acid residue corresponding to a 30th alanine residue from the N-terminal is changed into an amino acid residue other than alanine and other than acidic amino acid in the β-subunit in the amino acid sequence of the wild type AK. The amino acid sequence of the wild type AK specifically includes the amino acid sequence shown in SEQ ID NO: 5 in Sequence Listing as the α-subunit, and the amino acid sequence shown in SEQ ID NO: 7 in Sequence Listing as the β-subunit.

Those preferred as the amino acid residue other than alanine and other than acidic amino acid include threonine, arginine, cysteine, phenylalanine, proline, serine, tyrosine, and valine residues.

The codon corresponding to an amino acid residue to be substituted is not specifically limited for its type provided that it codes for the amino acid residue. It is predicted that the amino acid sequence of wild type AK may slightly differ depending on the difference in bacterial species and bacterial strains. AK's, which have mutation based on, for example, substitution, deletion, or insertion of one or more amino acid residues at one or more positions irrelevant to the enzyme activity as described above, can be also used for the present invention. A DNA coding for AK having the spontaneous mutation can be obtained by isolating a DNA which is hybridizable with, for example, the DNA having a part of the nucleotide sequence shown in SEQ ID NO: 3 under the stringent condition. By the "stringent condition" referred to herein is meant a condition under which a specific hybrid is formed, and nonspecific hybrid is not formed. It is difficult to clearly express the condition with numerical values. However, the condition is exemplified by a condition under which, nucleic acid having high homology, for example, DNA's having homology of not less than 90% are hybridized with each other, and nucleic acids having homology lower than the above are not hybridized with each other, or a condition of a temperature of from a melting out temperature (Tm) of a completely-matched hybrid to (Tm—30)° C., preferably from Tm to (Tm—20)° C. and a salt concentration corresponding to 1× SSC, preferably 0.1× SSC.

Other AK's, which have artificial mutation based on, for example, substitution, deletion, or insertion of other one or more amino acid residues, can be also used provided that no influence is substantially exerted on the AK activity, and on the desensitization of synergistic feedback inhibition by L-lysine and L-threonine. A DNA coding for AK having the artificial mutation can be obtained by modifying the nucleotide sequence to give substitution, deletion or insertion of a specified site by, for example, site-specific mutagenesis. Also, lysC having the mutation can be obtained by known mutagen treatment. The mutagen treatment includes in vitro treatment of a DNA containing lysC with hydroxylamine or the like, and treatment of microorganism harboring a DNA containing lysC with a mutagen such as ultraviolet irradiation or a mutagenic agent used for ordinary artificial mutagenesis such as N-methyl-N'-nitro-N-nitrosoguanidine (NTG) or nitric acid. After the mutagen treatment, a site to which mutation is introduced or in which mutation occurs can be determined by selecting a DNA or a microorganism which codes for or produces AK which has the AK activity and whose amino acid sequence is mutated from the DNA subjected to the mutagen treatment or the microorganism subjected to the mutagen treatment. A site of the introduced mutation is not specifically restricted provided that no influence is substantially exerted on the AK activity and on desensitization of feedback inhibition. A number of the introduced mutation varies depending on a site or a kind of the mutated amino acid in a steric structure of a protein, and is not specifically restricted provided that no influence is substantially exerted on the AK activity and on desensitization of feedback inhibition. The number is usually 1 to 20, preferably 1 to 10.

An amino acid residue corresponding to the specified alanine residue in the amino acid sequence of AK having the mutation as described above can be easily determined by one skilled in the art.

An AJ12691 strain obtained by introducing a mutant lysC plasmid p399AK9B into an AJ12036 strain (FERM BP-734) as a wild type strain of *Brevibacterium lactofermentum* has been deposited on Apr. 10, 1992 under an accession number of FERM P-12918 in National Institute of Bioscience and Human Technology of Agency of Industrial Science and Technology of Ministry of International Trade and Industry (1–3, Higashi 1-chome, Tsukuba-shi, Ibaraki-ken, 305 Japan), transferred to international deposition based on the Budapest Treaty on February 10, 1995, and deposited under an accession number of FERM BP-4999.

(2) Preparation of dapB

A DNA fragment containing dapB can be prepared from chromosome of a coryneform bacterium by means of PCR. The DNA donor is not specifically limited, however, it is exemplified by *Brevibacterium lactofermentum* ATCC 13869 strain.

A DNA sequence coding for DDPR is known for *Brevibacterium lactofermentum* (*Journal of Bacteriology*, 175(9), 2743–2749 (1993)), on the basis of which DNA primers for PCR can be prepared. Such DNA primers are specifically exemplified by DNA's of 23-mers respectively having nucleotide sequences depicted in SEQ ID NOs: 8 and 9 in Sequence Listing. Synthesis of DNA, PCR, and preparation of a plasmid containing obtained dapB can be performed in the same manner as those for lysC described above.

A nucleotide sequence of a DNA fragment containing dapB and an amino acid sequence deduced from the nucleotide sequence are illustrated in SEQ ID NO: 10. Only the amino acid sequence is shown in SEQ ID NO: 11. In addition to DNA fragments coding for this amino acid sequence, the present invention can equivalently use DNA fragments coding for amino acid sequences substantially the same as the amino acid sequence shown in SEQ ID NO: 11, namely amino acid sequences having mutation based on, for example, substitution, deletion, or insertion of one or more amino acids provided that there is no substantial influence on the DDPR activity. The dapB having spontaneous or artificial mutation can be obtained in the same manner as those for the DNA coding for AK having mutation which exerts no influence on the AK activity and on the desensitization of synergistic feedback inhibition by L-lysine and L-threonine.

A transformant strain AJ13107 obtained by introducing a plasmid pCRDAPB containing dapB obtained in Example described later on into *E. coli* JM109 strain has been internationally deposited since May 26, 1995 under an accession number of FERM BP-5114 in National Institute of Bioscience and Human Technology of Agency of Industrial Science and Technology of Ministry of International Trade and Industry (1–3, Higashi 1-chome, Tsukuba-shi, Ibaraki-ken, 305 Japan) based on the Budapest Treaty.

(3) Preparation of dapA

A DNA fragment containing dapA can be prepared from chromosome of a coryneform bacterium by means of PCR. The DNA donor is not specifically limited, however, it is exemplified by *Brevibacterium lactofermentum* ATCC 13869 strain.

A DNA sequence coding for DDPS is known for *Corynebacterium glutamicum* (see *Nucleic Acids Research*, 18(21), 6421 (1990); EMBL accession No. X53993), on the basis of which DNA primers for PCR can be prepared. Such DNA primers are specifically exemplified by DNA's of 23-mers respectively having nucleotide sequences depicted in SEQ ID NOs: 12 and 13 in Sequence Listing. Synthesis of DNA, PCR, and preparation of a plasmid containing obtained dapA can be performed in the same manner as those for lysC described above.

A nucleotide sequence of a DNA fragment containing dapA and an amino acid sequence deduced from the nucleotide sequence are exemplified in SEQ ID NO: 14. Only the amino acid sequence is shown in SEQ ID NO: 15. In addition to DNA fragments coding for this amino acid sequence, the present invention can equivalently use DNA fragments coding for amino acid sequences substantially the same as the amino acid sequence shown in SEQ ID NO: 15, namely amino acid sequences having mutation based on, for example, substitution, deletion, or insertion of one or more amino acids provided that there is no substantial influence on the DDPS activity. The dapA having spontaneous or artificial mutation can be obtained in the same manner as those for the DNA coding for AK having mutation which exerts no influence on the AK activity and on the desensitization of synergistic feedback inhibition by L-lysine and L-threonine.

A transformant strain AJ13106 obtained by introducing a plasmid pCRDAPA containing dapA obtained in Example described later on into *E. coli* JM109 strain has been internationally deposited since May 26, 1995 under an accession number of FERM BP-5113 in National Institute of Bioscience and Human Technology of Agency of Industrial Science and Technology of Ministry of International Trade and Industry (1-3, Higashi 1-chome, Tsukuba-shi, Ibaraki-ken, 305 Japan) based on the Budapest Treaty.

(4) Preparation of lysA

A DNA fragment containing lysA can be prepared from chromosome of a coryneform bacterium by means of PCR. The DNA donor is not specifically limited, however, it is exemplified by *Brevibacterium lactofermentum* ATCC 13869 strain.

In the coryneform bacteria, lysA forms an operon together with argS (arginyl-tRNA synthase gene), and lysA exists downstream from argS. Expression of lysA is regulated by a promoter existing upstream from argS (see *Journal of Bacteriology*, November, 7356–7362 (1993)). DNA sequences of these genes are known for *Corynebacterium glutamicum* (see *Molecular Microbiology*, 4(11), 1819–1830 (1990); *Molecular and General Genetics*, 212, 112–119 (1988)), on the basis of which DNA primers for PCR can be prepared. Such DNA primers are specifically exemplified by DNA's of 23-mers respectively having nucleotide sequences shown in SEQ ID NO: 16 in Sequence Listing (corresponding to nucleotide numbers 11 to 33 in a nucleotide sequence described in *Molecular Microbiology*, 4(11), 1819–1830 (1990)) and SEQ ID NO: 17 (corresponding to nucleotide numbers 1370 to 1392 in a nucleotide sequence described in *Molecular and General Genetics*, 212, 112–119 (1988)). Synthesis of DNA, PCR, and preparation of a plasmid containing obtained lysA can be performed in the same manner as those for lysC described above.

In Example described later on, a DNA fragment containing a promoter, argS, and lysA was used in order to enhance lysA. However, argS is not essential for the present invention. It is allowable to use a DNA fragment in which lysA is ligated just downstream from a promoter.

A nucleotide sequence of a DNA fragment containing argS and lysA, and an amino acid sequence deduced to be encoded by the nucleotide sequence are exemplified in SEQ ID NO: 18. An example of an amino acid sequence encoded by argS is shown in SEQ ID NO: 19, and an example of an amino acid sequence encoded by lysA is shown in SEQ ID NO: 20. In addition to DNA fragments coding for these amino acid sequences, the present invention can equivalently use DNA fragments coding for amino acid sequences substantially the same as the amino acid sequence shown in SEQ ID NO: 20, namely amino acid sequences having mutation based on, for example, substitution, deletion, or insertion of one or more amino acids provided that there is no substantial influence on the DDC activity. The lysA having spontaneous or artificial mutation can be obtained in the same manner as those for the DNA coding for AK having mutation which exerts no influence on the AK activity and on the desensitization of synergistic feedback inhibition by L-lysine and L-threonine.

(5) Preparation of aspC

A DNA fragment containing aspC can be prepared from a gene library prepared from chromosome of a microorganism such as a coryneform bacterium and a bacterium belonging to the genus Escherichia by using complementarity to an auxotrophic property of an AAT-deficient strain as an indication. The DNA donor of the coryneform bacterium is not specifically limited, however, it is exemplified by *Brevibacterium lactofermentum* ATCC 13869 strain. The DNA donor of the bacterium belonging to the genus Escherichia is not specifically limited, however, it is exemplified by *E. coli* JM109 strain.

Specifically, a method for preparing aspC of coryneform bacteria is known (Japanese Patent Publication No. 6-102028) and aspC can be prepared according to this method.

A DNA sequence coding for AAT is known for *E. coli* (Kuramitsu, S. et al., *J. Biochem.*, 97(4), 1259–1262 (1985)), on the basis of which primers for PCR can be prepared. Such DNA primers are specifically exemplified by DNA's of 20-mers respectively having nucleotide sequences depicted in SEQ ID NOs: 21 and 22 in Sequence Listing. Synthesis of DNA, PCR, and preparation of a plasmid containing obtained aspC can be performed in the same manner as those for lysC described above.

A nucleotide sequence of a DNA fragment containing aspC and an amino acid sequence deduced from the nucleotide sequence are illustrated in SEQ ID NO: 23. Only the amino acid sequence is shown in SEQ ID NO: 24. Another nucleotide sequence of a DNA fragment containing aspC and an amino acid sequence deduced from the nucleotide sequence are illustrated in SEQ ID NO: 30. Only the amino acid sequence is shown in SEQ ID NO: 31. In addition to DNA fragments coding for this amino acid sequence, the present invention can equivalently use DNA fragments coding for amino acid sequences substantially the same as the amino acid sequence shown in SEQ ID NO: 24 or 31, namely amino acid sequences having mutation based on, for example, substitution, deletion, or insertion of one or more amino acids provided that there is no substantial influence on the AAT activity. The aspC having spontaneous or artificial mutation can be obtained in the same manner as those for the DNA coding for AK having mutation which exerts no influence on the AK activity and on the desensitization of synergistic feedback inhibition by L-lysine and L-threonine.

The aspC having the nucleotide sequence shown in SEQ ID NO: 30 originates from *Corynebacterium lactofermentum*, and has been firstly obtained according to the method described in Example 9 described below by the present invention. Thus, the present invention provides a DNA coding for a protein comprising the amino acid sequence shown in SEQ ID NO: 31. An example of the DNA includes a DNA comprising a nucleotide sequence of nucleotide number 879 to 2174 in a nucleotide sequence shown in SEQ ID NO: 30.

<2>Recombinant DNA and coryneform bacterium of the present invention

The coryneform bacterium of the present invention harbors an aspartokinase (mutant AK) in which feedback inhibition by L-lysine and L-threonine is substantially desensitized, wherein the DNA sequence coding for a dihydrodipicolinate reductase, the DNA sequence coding for a dihydordipicolinate synthase, the DNA sequence coding for a diaminopimelate decarboxylase and the DNA coding for an aspartate aminotransferase are enhanced.

The term "enhance" herein refers to the fact that the intracellular activity of an enzyme encoded by the DNA is raised by, for example, increasing the copy number of a gene, using a strong promoter, using a gene coding for an enzyme having a high specific activity, or combining these means.

The coryneform bacterium harboring the mutant AK may be those which produce the mutant aspartokinase as a result of mutation, or those which are transformed by introducing mutant lysC.

Examples of the coryneform bacterium used to introduce the DNA described above include, for example, the following lysine-producing wild type strains:
*Corynebacterium acetoacidophilum* ATCC 13870;
*Corynebacterium acetoglutamicum* ATCC 15806;
*Corynebacterium callunae* ATCC 15991;
*Corynebacterium glutamicum* ATCC 13032;
(*Brevibacterium divaricatum*) ATCC 14020;
(*Brevibacterium lactofermentum*) ATCC 13869;
(*Corynebacterium lilium*) ATCC 15990;
(*Brevibacterium flavum*) ATCC 14067;
*Corynebacterium melassecola* ATCC 17965;
*Brevibacterium saccharolyticum* ATCC 14066;
*Brevibacterium immariophilum* ATCC 14068;
*Brevibacterium roseum* ATCC 13825;
*Brevibacterium thiogenitalis* ATCC 19240;
*Microbacterium ammoniaphilum* ATCC 15354;
*Corynebacterium thermoaminogenes* AJ12340 (FERM BP-1539).

Other than the bacterial strains described above, those usable as a host include, for example, mutant strains having an L-lysine-producing ability derived from the aforementioned strains. Such artificial mutant strains includes the followings: S-(2-aminoethyl)-cystein (hereinafter abbreviated as "AEC") resistant mutant strains (for example, *Brevibacterium lactofermentum* AJ11082 (NRRL B-1147), Japanese Patent Publication Nos. 56-1914, 56-1915, 57-14157, 57-14158, 57-30474, 58-10075, 59-4993, 61-35840, 62-24074, 62-36673, 5-11958, 7-112437, and 7-112438); mutant strains which require amino acid such as L-homoserine for their growth (Japanese Patent Publication Nos. 48-28078 and 56-6499); mutant strains which exhibit resistance to AEC and require amino acids such as L-leucine, L-homoserine, L-proline, L-serine, L-arginine, L-alanine, and L-valine (U.S. Pat. Nos. 3,708,395 and 3,825,472); L-lysine-producing mutant strains which exhibit resistance to DL-α-amino-ε-caprolactam, α-aminolauryllactam, aspartate-analog, sulfa drug, quinoid, and N-lauroylleucine; L-lysine-producing mutant strains which exhibit resistance to inhibitors of oxyaloacetate decarboxylase or respiratory system enzymes (Japanese Patent Application Laid-open Nos. 50-53588, 50-31093, 52-102498, 53-9394, 53-86089, 55-9783, 55-9759, 56-32995 and 56-39778, and Japanese Patent Publication Nos. 53-43591 and 53-1833); L-lysine-producing mutant strains which require inositol or acetic acid (Japanese Patent Application Laid-open Nos. 55-9784 and 56-8692); L-lysine-producing mutant strains which exhibit sensitivity to fluoropyruvic acid or temperature not less than 34° C (Japanese Patent Application Laid-open Nos. 55-9783 and 53-86090); and producing mutant strains belonging to the genus Brevibacterium or Corynebacterium which exhibit resistance to ethylene glycol and produce L-lysine (U.S. Pat. No. 4,411,997).

In a specified embodiment, in order to enhance the genes for L-lysine biosynthesis in the host as described above, the genes are introduced into the host by using a plasmid vector, transposon or phage vector or the like. Upon the introduction, it is expected to make enhancement to some extent even by using a low copy type vector. However, it is preferred to use a multiple copy type vector. Such a vector includes, for example, plasmid vectors, pAJ655, pAJ1844, pAJ611, pAJ3148, and pAJ440 described above. Besides, transposons derived from coryneform bacteria are described in International Publication Pamphlets of WO02/02627 and WO93/18151, European Patent Publication No. 445385, Japanese Patent Application Laid-open No. 6-46867, Vertes, A. A. et al., Mol. Microbiol., 11, 739–746 (1994), Bonamy, C., et al., Mol. Microbiol., 14, 571–581 (1994), Vertes, A. A. et al., Mol. Gen. Genet., 245, 397–405 (1994), Jagar, W. et al., FEMS Microbiology Letters, 126, 1–6 (1995), Japanese Patent Application Laid-open No. 7-107976, Japanese Patent Application Laid-open No. 7-327680 and the like.

In the present invention, it is not indispensable that the mutant lysC is necessarily enhanced. It is allowable to use those which have mutation on lysC on chromosomal DNA, or in which the mutant lysC is incorporated into chromosomal DNA. Alternatively, the mutant lysC may be introduced by using a plasmid vector. On the other hand, dapA, dapB, lysA, and aspC are preferably enhanced in order to efficiently produce L-lysine.

Each of the genes of lysC, dapA, dapB, lysA, and aspC may be successively introduced into the host by using different vectors respectively. Alternatively, two, three, four, or five species of the genes may be introduced together by using a single vector. When different vectors are used, the genes may be introduced in any order, however, it is preferred to use vectors which have a stable sharing and harboring mechanism in the host, and which are capable of co-existing with each other.

Particularly, as a vector for introducing aspC into coryneform bacteria, a vector pVK7 is preferably used. The vector pVK7 is a cloning vector for coryneform bacteria provided by the present invention, which is autonomously replicable in cells of *Eschericia coli* and *Brevibacterium lactofermentum*, and comprising a multiple cloning site and lacZ'. The vector pVK7 can be constructed according to the method described in Example 8 described below.

A coryneform bacterium harboring the mutant AK and further comprising enhanced dapB, dapA, lysA and aspC is obtained, for example, by introducing, into a host coryneform bacterium, a recombinant DNA containing mutant lysC and dapB, dapA, lysA and aspC autonomously replicable in cells of coryneform bacteria.

The above-mentioned recombinant DNAs can be obtained, for example, by inserting each of the genes participating in L-lysine biosynthesis into a vector such as plasmid vector, transposon or phage vector as described above.

In the case in which a plasmid is used as a vector, the recombinant DNA can be introduced into the host in accordance with an electric pulse method (Sugimoto et al., Japanese Patent Application Laid-open No. 2-207791). Amplification of a gene using transposon can be performed by introducing a plasmid which carrying a transposon into the host cell and inducing transposition of the transposon.

In coryneform bacteria used in the present invention, a gene participating in L-lysine biosynthesis such as a DNA sequence coding for a phosphoenolpyruvate carboxylase and a DNA sequence coding for a diaminopimelate dehydrogenase may be enhanced in addition to the above-mentioned genes.

<3>Method for producing L-lysine

L-Lysine can be efficiently produced by cultivating, in an appropriate medium, the coryneform bacterium comprising the enhanced genes for L-lysine biosynthesis as described above, to allow L-lysine to be produced and accumulated in a culture of the bacterium, and collecting L-lysine from the culture.

The medium to be used is exemplified by an ordinary medium containing a carbon source, a nitrogen source, inorganic ions, and optionally other organic components.

As the carbon source, it is possible to use sugars such as glucose, fructose, sucrose, molasses, and starch hydrolysate; and organic acids such as fumaric acid, citric acid, and succinic acid.

As the nitrogen source, it is possible to use inorganic ammonium salts such as ammonium sulfate, ammonium chloride, and ammonium phosphate; organic nitrogen such as soybean hydrolysate; ammonia gas; and aqueous ammonia.

As organic trace nutrient sources, it is desirable to contain required substances such as vitamin Bs and L-homoserine or yeast extract or the like in appropriate amounts. Other than the above, potassium phosphate, magnesium sulfate, iron ion, manganese ion and so on are added in small amounts, if necessary.

Cultivation is preferably carried out under an aerobic condition for about 30 to 90 hours. The cultivation temperature is preferably controlled at 25° C. to 37° C., and pH is preferably controlled at 5 to 8 during cultivation. Inorganic or organic, acidic or alkaline substances, or ammonia gas or the like can be used for pH adjustment. L-lysine can be collected from a culture by combining an ordinary ion exchange resin method, a precipitation method, and other known methods.

EXAMPLES

The present invention will be more specifically explained below with reference to Examples.

Example 1

Preparation of Wild Type lysC Gene and Mutant lysC Gene from *Brevibacterium lactofermentum*

<1>Preparation of wild type and mutant lysC's and preparation of plasmids containing them A strain of *Brevibacterium lactofermentum* ATCC 13869, and an L-lysine-producing mutant strain AJ3445 (FERM P-1944) obtained from the ATCC 13869 strain by a mutation treatment were used as chromosomal DNA donors. The AJ3445 strain had been subjected to mutation so that lysC was changed to involve substantial desensitization from concerted inhibition by lysine and threonine (*Journal of Biochemistry*, 68, 701–710 (1970)).

A DNA fragment containing lysC was amplified from chromosomal DNA in accordance with the PCR method (polymerase chain reaction; see White, T. J. et al., *Trends Genet.*, 5, 185 (1989)). As for DNA primers used for amplification, single strand DNA's of 23-mer and 21-mer having nucleotide sequences shown in SEQ ID NOs: 1 and 2 were synthesized in order to amplify a region of about 1,643 bp coding for lysC on the basis of a sequence known for *Corynebacterium glutamicum* (see *Molecular Microbiology* (1991), 5(5), 1197–1204; and Mol. Gen. Genet. (1990), 224, 317-324). DNA was synthesized in accordance with an ordinary method by using DNA synthesizer model 380B produced by Applied Biosystems and using the phosphoamidite method (see *Tetrahedron Letters* (1981), 22, 1859).

The gene was amplified by PCR by using DNA Thermal Cycler Model PJ2000 produced by Takara Shuzo, and using Taq DNA polymerase in accordance with a method designated by the supplier. An amplified gene fragment of 1,643 kb was confirmed by agarose gel electrophoresis. After that, the fragment excised from the gel was purified in accordance with an ordinary method, and it was digested with restriction enzymes NruI (produced by Takara Shuzo) and EcoRI (produced by Takara Shuzo).

pHSG399 (see Takeshita, S. et al., *Gene* (1987), 61, 63–74) was used as a cloning vector for the gene fragment. pHSG399 was digested with restriction enzymes SmaI (produced by Takara Shuzo) and EcoRI, and it was ligated with the amplified lysC fragment. DNA was ligated by using DNA ligation kit (produced by Takara Shuzo) in accordance with a designated method. Thus plasmids were prepared, in which the lysC fragments amplified from chromosomes of *Brevibacterium lactofermentum* were ligated with pHSG399 respectively. A plasmid comprising lysC from ATCC 13869 (wild type strain) was designated as p399AKY, and a plasmid comprising lysC from AJ3463 (L-lysine-producing bacterium) was designated as p399AK9.

A DNA fragment (hereinafter referred to as "Brevi.-ori") having an ability to make a plasmid autonomously replicable in bacteria belonging to the genus Corynebacterium was introduced into p399AKY and p399AK9 respectively to prepare plasmids carrying lysC autonomously replicable in bacteria belonging to the genus Corynebacterium. Brevi.-ori was prepared from a plasmid vector pHK4 containing Brevi.-ori and autonomously replicable in cells of both *Escherichia coli* and bacteria belonging to the genus Corynebacterium. pHK4 was constructed by digesting pHC4 with KpnI (produced by Takara Shuzo) and BamHI (produced by Takara Shuzo), extracting a Brevi.-ori fragment, and ligating it with pHSG298 having been also digested with KpnI and BamHI (see Japanese Patent Application Laid-open No. 5-7491). pHK4 gives kanamycin resistance to a host. *Eschericia coli* harboring pHK4 was designated as *Eschericia coli* AJ13136, and deposited on Aug. 1, 1995 under an accession number of FERM BP-5186 in National Institute of Bioscience and Human Technology of Agency of Industrial Science and Technology of Ministry of International Trade and Industry (1-3, Higashi 1-chome, Tsukuba-shi, Ibaraki-ken, 305 Japan).

pHK4 was digested with restriction enzymes KpnI and BamHI, and cleaved edges were blunt-ended. Blunt end formation was performed by using DNA Blunting kit (produced by Takara Shuzo) in accordance with a designated method. After the blunt end formation, a phosphorylated BamHI linker (produced by Takara Shuzo) was ligated to make modification so that the DNA fragment corresponding to the Brevi.-ori portion might be excised from pHK4 by digestion with only BamHI. This plasmid was digested with BamHI, and the generated Brevi.-ori DNA fragment was ligated with p399AKY and p399AK9 having been also digested with BamHI respectively to prepare plasmids each containing the lysC gene autonomously replicable in bacteria belonging to the genus Corynebacterium.

A plasmid containing the wild type lysC gene originating from p399AKY was designated as p399AKYB, and a plasmid containing the mutant lvsC gene originating from p399AK9 was designated as p399AK9B. The process of construction of p399AK9B and p399AKYB is shown in FIG. 1. A strain AJ12691 obtained by introducing the mutant lvsC plasmid p399AK9B into a wild type strain of *Brevibacterium lactofermentum* (AJ12036 strain, FERM BP-734) was deposited on Apr. 10, 1992 under an accession number of FERM P-12918 in National Institute of Bioscience and Human Technology of Agency of Industrial Science and Technology of Ministry of International Trade and Industry (1–3, Higashi 1-chome, Tsukuba-shi, Ibaraki-ken, 305 Japan), transferred to international deposition based on the Budapest Treaty on Feb. 10, 1995, and deposited under an accession number of FERM BP-4999.

<2>Determination of nucleotide sequences of wild type lysC and mutant lysC from *Brevibacterium lactofermentum*

The plasmid p399AKY containing the wild type lysC and the plasmid p399AK9 containing the mutant lysC were prepared from the respective transformants to determine nucleotide sequences of the wild type and mutant lysC's. Nucleotide sequence determination was performed in accordance with a method of Sanger et al. (for example, F. Sanger et al., *Proc. Natl. Acad. Sci.*, 74, 5463 (1977)).

The nucleotide sequence of wild type lysC encoded by p399AKY is shown in SEQ ID NO: 3 in Sequence Listing. On the other hand, the nucleotide sequence of mutant lysC encoded by p399AK9 had only mutation of one nucleotide such that 1051st G was changed into A in SEQ ID NO: 3 as compared with wild type lysC. It is known that lysC of *Corynebacterium glutamicum* has two subunits ($\alpha$, $\beta$) encoded in an identical reading frame on an identical DNA strand (see Kalinowski, J. et al., *Molecular Microbiology* (1991) 5(5), 1197–1204). Judging from homology, it is assumed that the gene sequenced herein also has two subunits ($\alpha$, $\beta$) encoded in an identical reading frame on an identical DNA strand.

An amino acid sequence of the $\alpha$-subunit of the wild type AK protein deduced from the nucleotide sequence of DNA is shown in SEQ ID NO: 4 together with the DNA sequence. Only the amino acid sequence is shown in SEQ ID NO: 5. An amino acid sequence of the i-subunit of the wild type AK protein deduced from the nucleotide sequence of DNA is shown in SEQ ID NO: 6 together with the DNA sequence. Only the amino acid sequence is shown in SEQ ID NO: 7. In each of the subunits, GTG is used as an initiation codon, and a corresponding amino acid is represented by methionine. However, this representation refers to methionine, valine, or formylmethionine.

On the other hand, mutation on the sequence of mutant lysC means occurrence of amino acid residue substitution such that a 279th alanine residue of the $\alpha$-subunit is changed into a threonine residue, and a 30th alanine residue of the $\beta$-subunit is changed into a threonine residue in the amino acid sequence of the wild type AK protein (SEQ ID NOs: 5, 7).

Example 2

Preparation of dapB from *Brevibacterium lactofermentum*

<1>Preparation of dapB and construction of plasmid containing dapB

A wild type strain of *Brevibacterium lactofermentum* ATCC 13869 was used as a chromosomal DNA donor. Chromosomal DNA was prepared from the ATCC 13869 strain in accordance with an ordinary method. A DNA fragment containing daDb was amplified from the chromosomal DNA in accordance with PCR. As for DNA primers used for amplification, DNA's of 23-mers having nucleotide sequences shown in SEQ ID NOs: 8 and 9 in Sequence Listing respectively were synthesized in order to amplify a region of about 2.0 kb coding for DDPR on the basis of a sequence known for *Brevibacterium lactofermentum* (see *Journal of Bacteriology*, 175(9), 2743-2749 (1993)). Synthesis of DNA and PCR were performed in the same manner as described in Example 1. pCR-Script (produced by Invitrogen) was used as a cloning vector for the amplified gene fragment of 2,001 bp, and was ligated with the amplified dapB fragment. Thus a plasmid was constructed, in which the dapB fragment of 2,001 bp amplified from chromosome of *Brevibacterium lactofermentum* was ligated with pCR-Script. The plasmid obtained as described above, which had dapB originating from ATCC 13869, was designated as PCRDAPB. A transformant strain AJ13107 obtained by introducing pCRDAPB into *E. coli* JM109 strain has been internationally deposited since May 26, 1995 under an accession number of FERM BP-5114 in National Institute of Bioscience and Human Technology of Agency of Industrial Science and Technology of Ministry of International Trade and Industry (1-3, Higashi 1-chome, Tsukuba-shi, Ibaraki-ken, 305 Japan) based on the Budapest Treaty.

A fragment of 1,101 bp containing a structural gene of DDPR was extracted by digesting pCRDAPB with EcoRV and SphI. This fragment was ligated with pHSG399 having been digested with HincII and SphI to prepare a plasmid. The prepared plasmid was designated as p399DPR.

Figure 2:
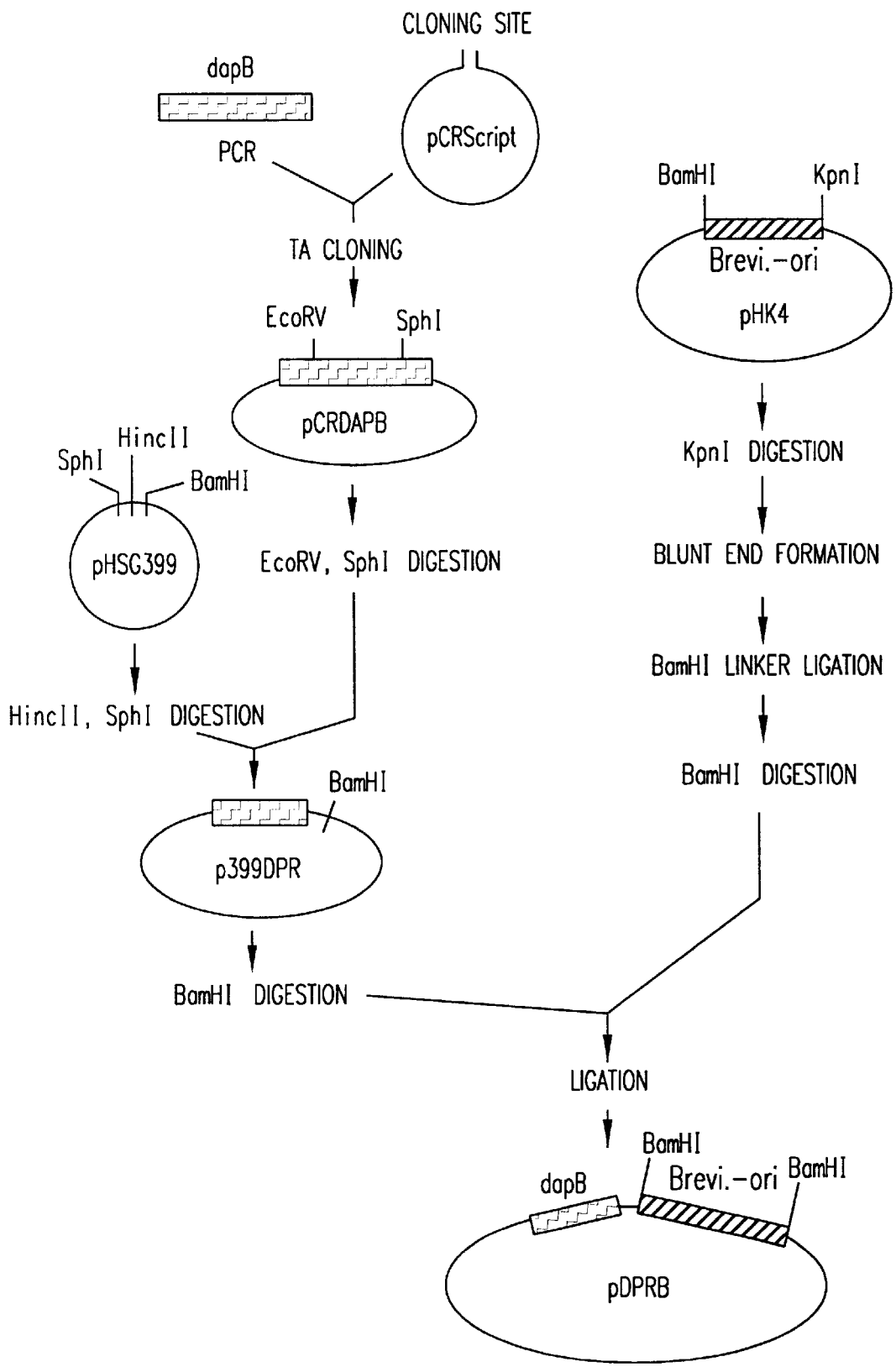
FIG. 2 illustrates a process of construction of a plasmid pDPRB comprising dapB and Brevi.-ori.

Brevi.-ori was introduced into the prepared p399DPR to construct a plasmid carrying dapB autonomously replicable in coryneform bacteria. pHK4 was digested with a restriction enzyme KpnI (produced by Takara Shuzo), and cleaved edges were blunt-ended. Blunt end formation was performed by using DNA Blunting kit (produced by Takara Shuzo) in accordance with a designated method. After the blunt end formation, a phosphorylated BamHI linker (produced by Takara Shuzo) was ligated to make modification so that the DNA fragment corresponding to the Brevi.-ori portion might be excised from pHK4 by digestion with only BamHI. This plasmid was digested with PmHI, and the generated Brevi.-ori DNA fragment was ligated with p399DPR having been also digested with BamHI to prepare a plasmid containing dapB autonomously replicable in coryneform bacteria. The prepared plasmid was designated as pDPRB. The process of construction of pDPRB is shown in FIG. 2.

<2>Determination of nucleotide sequence of dapB from *Brevibacterium lactofermentum*

Plasmid DNA was prepared from the AJ13107 strain harboring p399DPR, and its nucleotide sequence was determined in the same manner as described in Example 1. A determined nucleotide sequence and an amino acid sequence deduced from the nucleotide sequence are shown in SEQ ID NO: 10. Only the amino acid sequence is shown in SEQ ID NO: 11.

Example 3

Preparation of dapA from *Brevibacterium lactofermentum*

<1>Preparation of dapA and construction of plasmid containing dapA

A wild type strain of *Brevibacterium lactofermentum* ATCC 13869 was used as a chromosomal DNA donor. Chromosomal DNA was prepared from the ATCC 13869 strain in accordance with an ordinary method. A DNA fragment containing dapA was amplified from the chromosomal DNA in accordance with PCR. As for DNA primers used for amplification, DNAs of 23-mers having nucleotide sequences shown in SEQ ID NOs: 12 and 13 in Sequence Listing respectively were synthesized in order to amplify a region of about 1.5 kb coding for DDPS on the basis of a sequence known for *Corynebacterium glutamicum* (see *Nucleic Acids Research*, 18(21), 6421 (1990); EMBL accession No. X53993). Synthesis of DNA and PCR were performed in the same manner as described in Example 1. pCR1000 (produced by Invitrogen, see *Bio/Technology*, 9, 657–663 (1991)) was used as a cloning vector for the amplified gene fragment of 1,411 bp, and was ligated with the amplified dapA fragment. Ligation of DNA was performed by using DNA ligation kit (produced by Takara Shuzo) in accordance with a designated method. Thus a plasmid was constructed, in which the dapA fragment of 1,411 bp amplified from chromosome of *Brevibacterium lactofermentum* was ligated with pCR1000. The plasmid obtained as described above, which had dapA originating from ATCC 13869, was designated as pCRDAPA.

A transformant strain AJ13106 obtained by introducing pCRDAPA into *E. coli* JM109 strain has been internationally deposited since May 26, 1995 under an accession number of FERM BP-5113 in National Institute of Bioscience and Human Technology of Agency of Industrial Science and Technology of Ministry of International Trade and Industry (1–3, Higashi 1-chome, Tsukuba-shi, Ibaraki-ken, 305 Japan) based on the Budapest Treaty.

Figure 3:
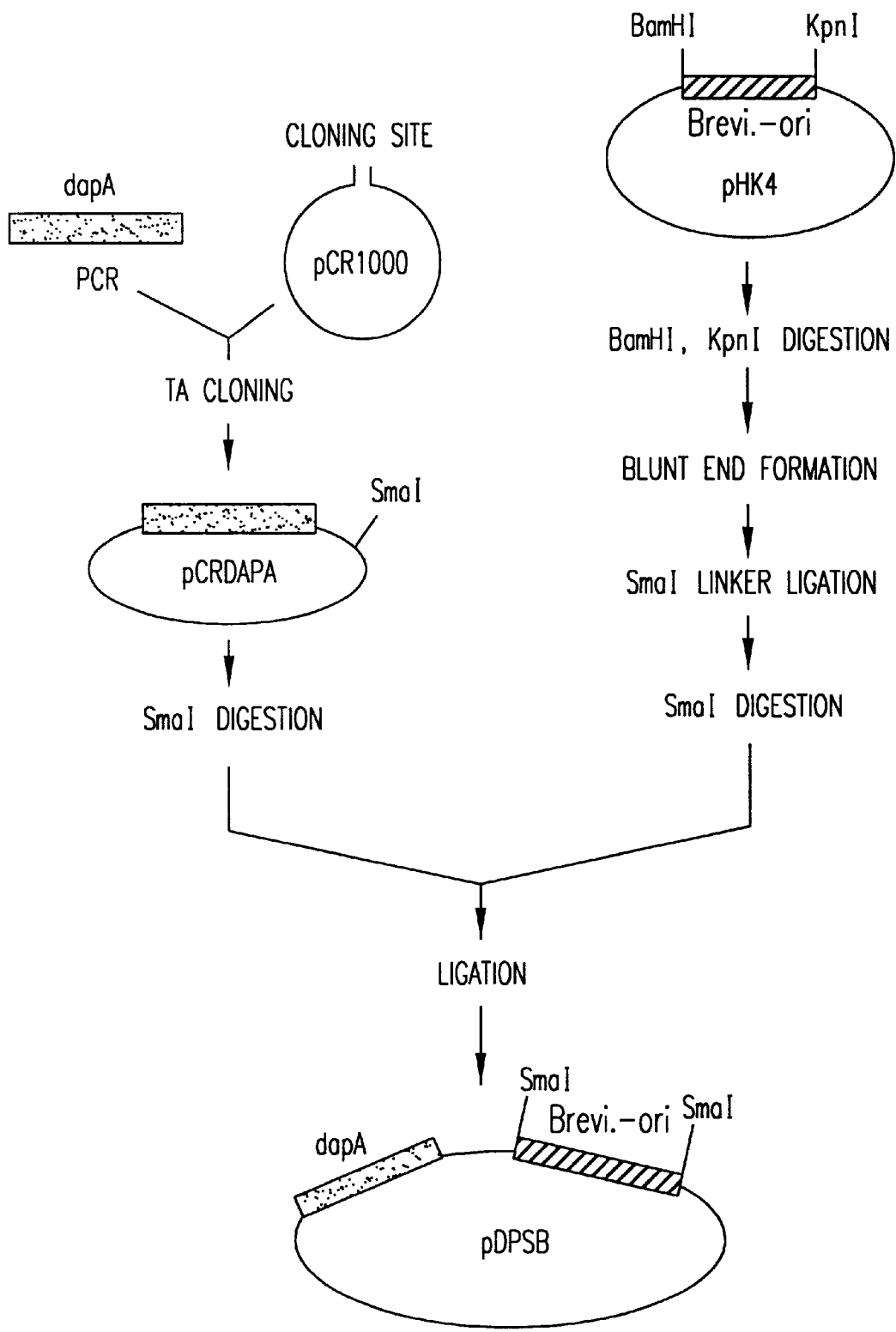
FIG. 3 illustrates a process of construction of a plasmid pDPSB comprising danA and Brevi.-ori.

Brevi.-ori was introduced into the prepared pCRDAPA to construct a plasmid carrying dapA autonomously replicable in coryneform bacteria. pHK4 was digested with restriction enzymes KpnI and BamHI (produced by Takara Shuzo), and cleaved edges were blunt-ended. Blunt end formation was performed by using DNA Blunting kit (produced by Takara Shuzo) in accordance with a designated method. After the blunt end formation, a phosphorylated SmaI linker (produced by Takara Shuzo) was ligated to make modification so that the DNA fragment corresponding to the Brevi.-ori portion might be excised from pHK4 by digestion with only SmaI. This plasmid was digested with SmaI, and the generated Brevi.-ori DNA fragment was ligated with pCRDAPA having been also digested with SmaI to prepare a plasmid containing dapA autonomously replicable in coryneform bacteria. This plasmid was designated as pDPSB. The process of construction of pDPSB(Km$^r$) is shown in FIG. 3.

<2>Determination of nucleotide sequence of dapA from *Brevibacterium lactofermentum*

Plasmid DNA was prepared from the AJ13106 strain harboring pCRDAPA, and its nucleotide sequence was determined in the same manner as described in Example 1. A determined nucleotide sequence and an amino acid sequence deduced from the nucleotide sequence are shown in SEQ ID NO: 14. Only the amino acid sequence is shown in SEQ ID NO: 15.

Example 4

Preparation of lysA from *Brevibacterium lactofermentum*

<1>Preparation of lysA and construction of plasmid containing lysA

A wild type strain of *Brevibacterium lactofermentum* ATCC 13869 was used as a chromosomal DNA donor. Chromosomal DNA was prepared from the ATCC 13869 strain in accordance with an ordinary method. A DNA fragment containing argS, lysA, and a promoter of an operon containing them was amplified from the chromosomal DNA in accordance with PCR. As for DNA primers used for amplification, synthetic DNAs of 23-mers having nucleotide sequences shown in SEQ ID NOs: 16 and 17 in Sequence Listing respectively were used in order to amplify a region of about 3.6 kb coding for arginyl-tRNA synthase and DDC on the basis of a sequence known for *Corynebacterium glutamicum* (see *Molecular Microbiology,* 4(11), 1819–1830 (1990); *Molecular and General Genetics,* 212, 112–119 (1988)). Synthesis of DNA and PCR were performed in the same manner as described in Example 1. pHSG399 was used as a cloning vector for the amplified gene fragment of 3,579 bp. pHSG399 was digested with a restriction enzyme SmaI (produced by Takara Shuzo), which was ligated with the DNA fragment containing amplified lysA. A plasmid obtained as described above, which had lysA originating from ATCC 13869, was designated as p399LYSA.

Figure 4:
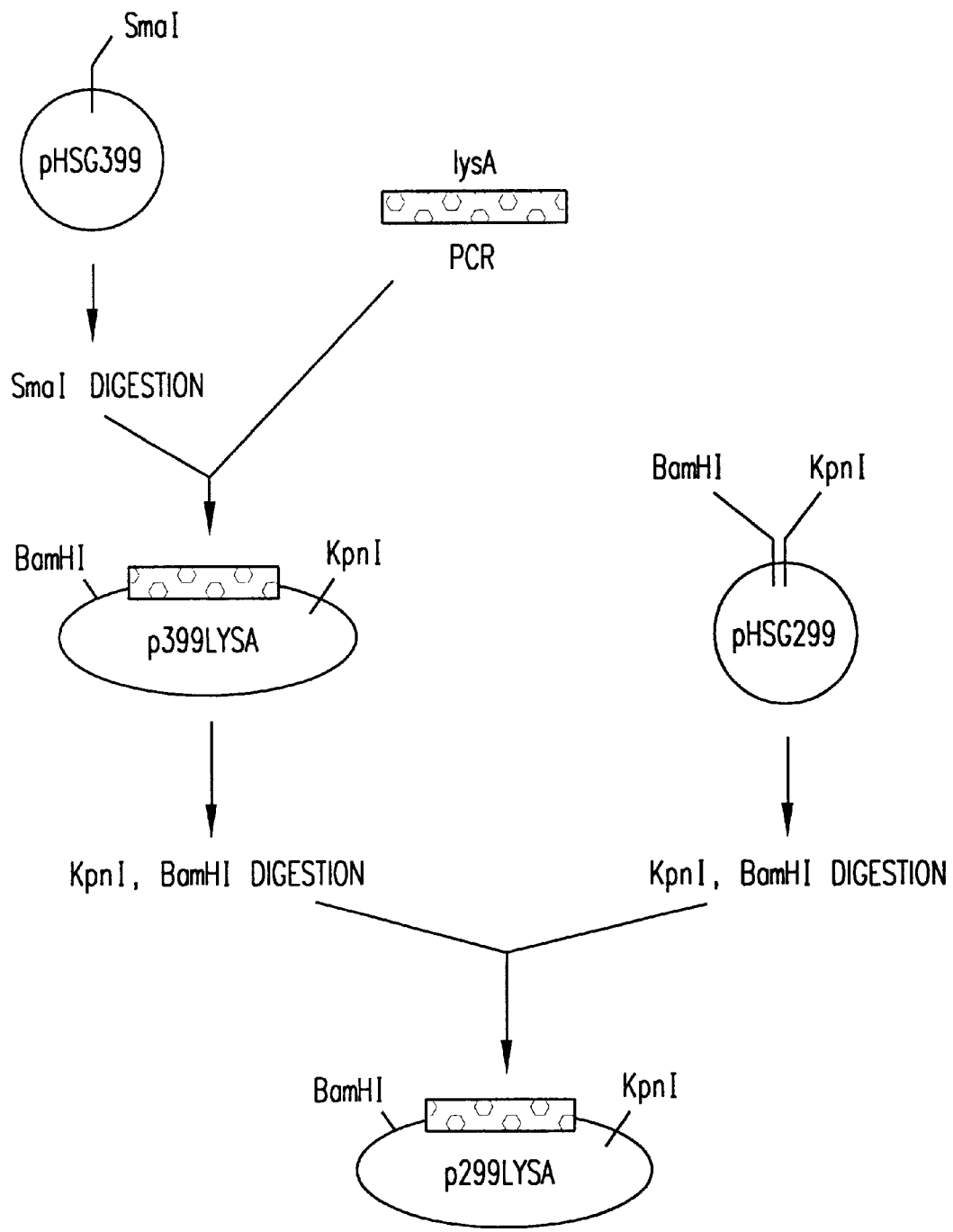
FIG. 4 illustrates a process of construction of a plasmid p299LYSA comprising lysA.

A DNA fragment containing lysA was extracted by digesting p399LYSA with KpnI (produced by Takara Shuzo) and BamHI (produced by Takara Shuzo). This DNA fragment was ligated with pHSG299 having been digested with KpnI and BamHI. An obtained plasmid was designated as p299LYSA. The process of construction of p299LYSA is shown in FIG. 4.

Figure 5:
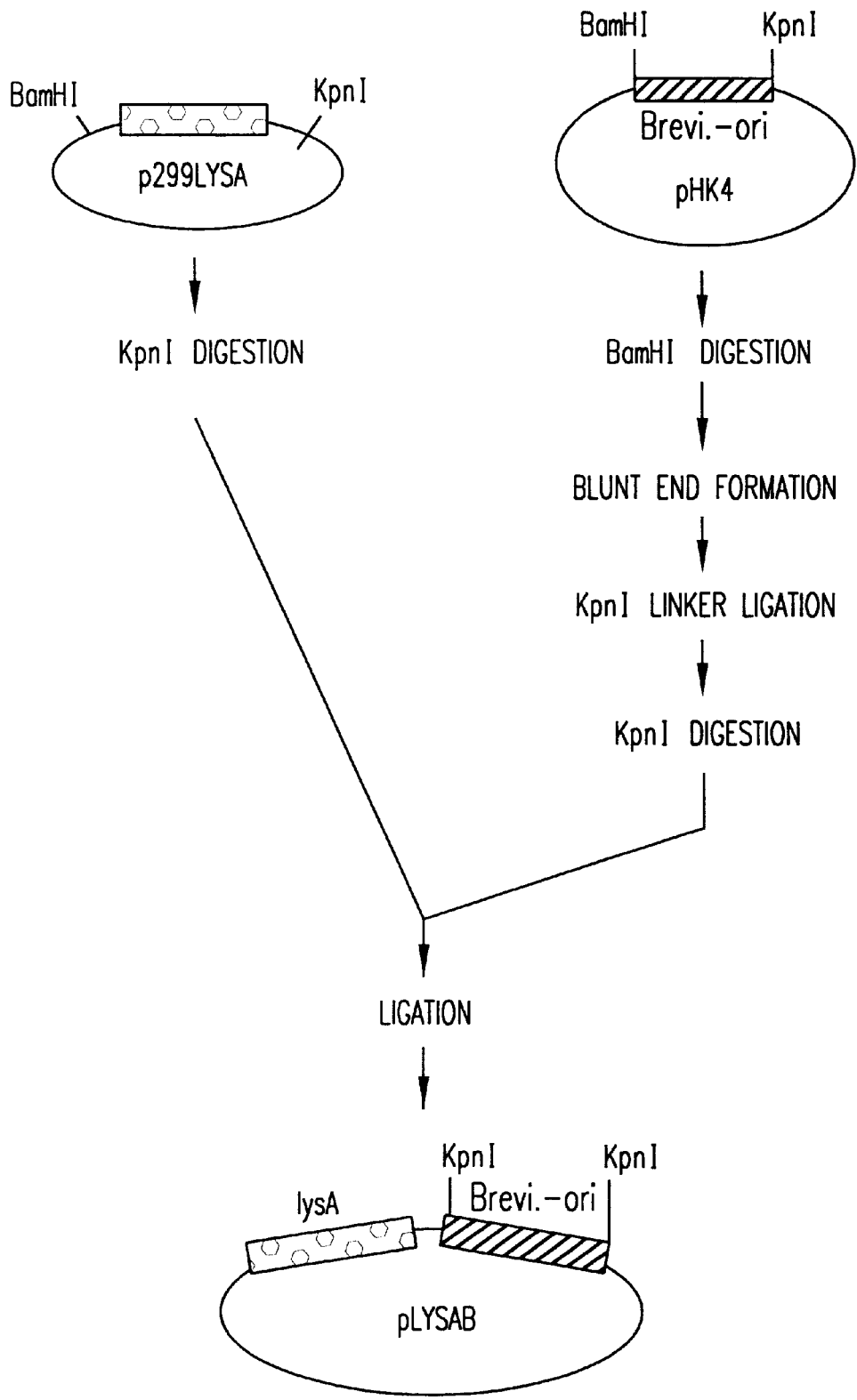
FIG. 5 illustrates a process of construction of a plasmid pLYSAB comprising lysA and Brevi.-ori.

Brevi.-ori was introduced into the obtained p299LYSA to construct a plasmid carrying lysA autonomously replicable in coryneform bacteria. pHK4 was digested with restriction enzymes KpnI and BamHI, and cleaved edges were blunt-ended. Blunt end formation was performed by using DNA Blunting kit (produced by Takara Shuzo) in accordance with a designated method. After the blunt end formation, a phosphorylated KpnI linker (produced by Takara Shuzo) was ligated to make modification so that the DNA fragment corresponding to the Brevi.-ori portion might be excised from pHK4 by digestion with only KpnI. This plasmid was digested with KpnI, and the generated Brevi.-ori DNA fragment was ligated with p299LYSA having been also digested with KpnI to prepare a plasmid containing lysA autonomously replicable in coryneform bacteria. The prepared plasmid was designated as PLYSAB. The process of construction of pLYSAB is shown in FIG. 5.

<2>Determination of nucleotide sequence of lysA from *Brevibacterium lactofermentum*

Plasmid DNA of p299LYSA was prepared, and its nucleotide sequence was determined in the same manner as described in Example 1. A determined nucleotide sequence and an amino acid sequence deduced to be encoded by the nucleotide sequence are shown in SEQ ID NO: 18. Concerning the nucleotide sequence, an amino acid sequence encoded by argS and an amino acid sequence encoded by lysA are shown in SEQ ID NOs: 19 and 20 respectively.

Example 5

Preparation of aspc from *Escherichia coli* and Construction of Plasmid Containing aspC An *Eschericia coli* JM109 strain was used as a chromosomal DNA donor. Chromosomal DNA was prepared from the *E. coli* JM109 strain in accordance with an ordinary method. A DNA fragment containing aspC was amplified from the chromosomal DNA in accordance with PCR. As for DNA primers used for amplification, synthetic DNA's of 20-mers having nucleotide sequences shown in SEQ ID NOs: 21 and 22 in Sequence Listing respectively were used on the basis of a sequence known for *E. coli* (see Kuramitsu, S. et al., *J. Biochem.,* 97(4), 1259–1262 (1985)). Synthesis of DNA and PCR were performed in the same manner as described in Example 1. The amplified fragment of 1,331 bp was cloned into TA cloning vector pCR1000. The constructed plasmid was designated as pCRASPC.

A nucleotide sequence of the amplified DNA containing aspC and an amino acid sequence deduced to be encoded by the nucleotide sequence are shown in SEQ ID NO: 23. Only the amino acid sequence is shown in SEQ ID NO: 24.

Comparative Example 1

Construction of Plasmid Comprising Combination of Mutant lysC and dapA

Figure 6:
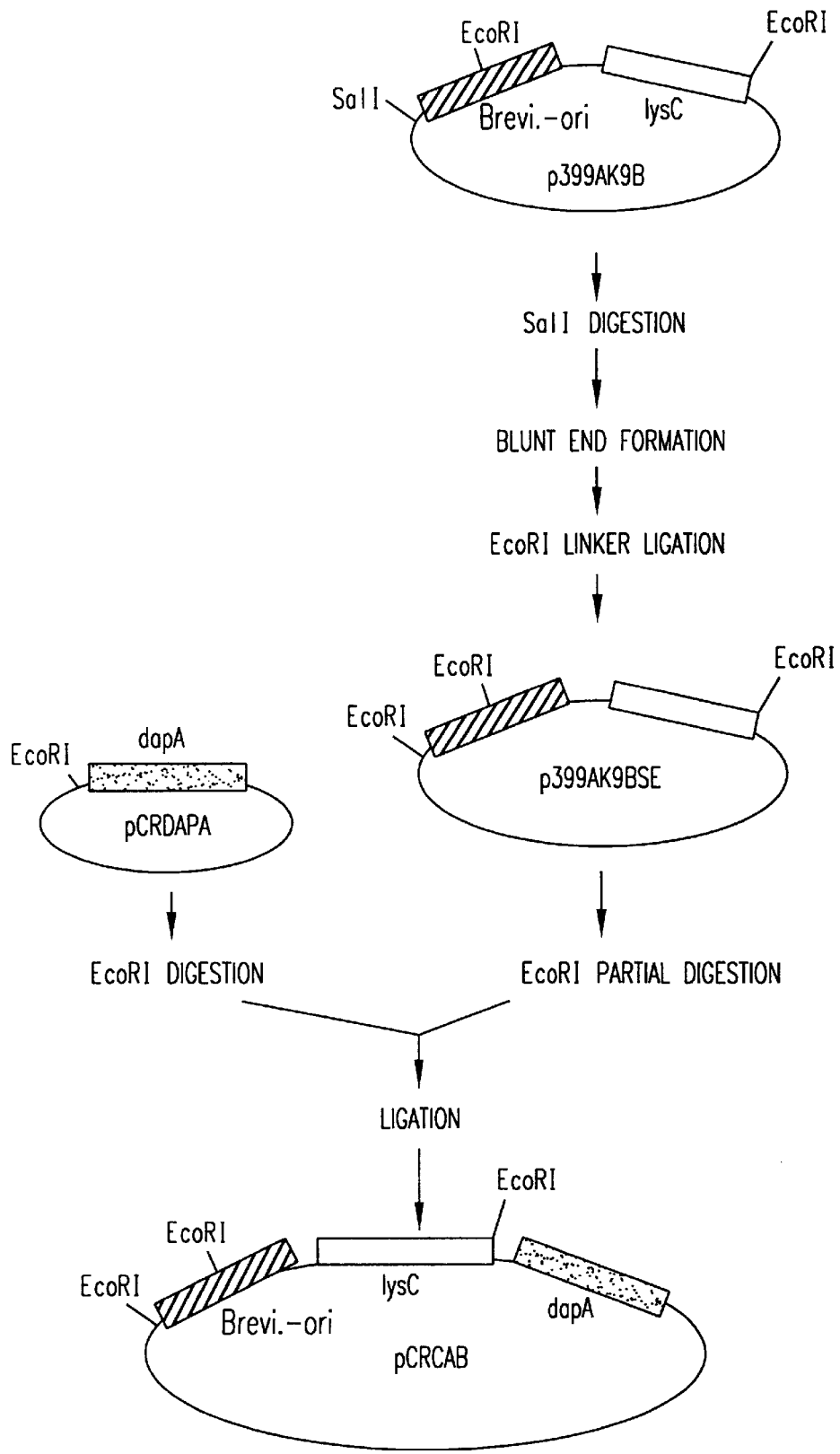
FIG. 6 illustrates a process of construction of a plasmid pCRCAB comprising lysC, dapB and Brevi.-ori.

A plasmid comprising mutant lysC, dapA, and replication origin of coryneform bacteria was constructed from the plasmid pCRDAPA comprising dapA and the plasmid p399AK9B comprising mutant lysC and Brevi.-ori. p399AK9B was completely digested with SalI, and then blunt-ended, and was ligated with an EcoRI linker to construct a plasmid in which the SalI site was modified into an EcoRI site. The obtained plasmid was designated as p399AK9BSE. The mutant lysC and Brevi.-ori were excised as one fragment by partially digesting p399AK9BSE with EcoRI. This fragment was ligated with pCRDAPA having been digested with S RI. An obtained plasmid was designated as pCRCAB. This plasmid is autonomously replicable in *E. coli* and coryneform bacteria, and it gives kanamycin resistance to a host, the plasmid comprising a combination of mutant lysC and dapA. The process of construction of pCRCAB is shown in FIG. 6.

Comparative Example 2

Construction of Plasmid Comprising Combination of Mutant lysC and dapB

A plasmid comprising mutant lysC and dapB was constructed from the plasmid p399AK9 having mutant lysC and the plasmid p399DPR having dapB. A fragment of 1,101 bp containing a structural gene of DDPR was extracted by digesting p399DPR with EcoRV and SphI. This fragment was ligated with p399AK9 having been digested with SalI and then blunt-ended and having been further digested with SphI to construct a plasmid comprising a combination of mutant lysC and dapB. This plasmid was designated as p399AKDDPR.

Figure 7:
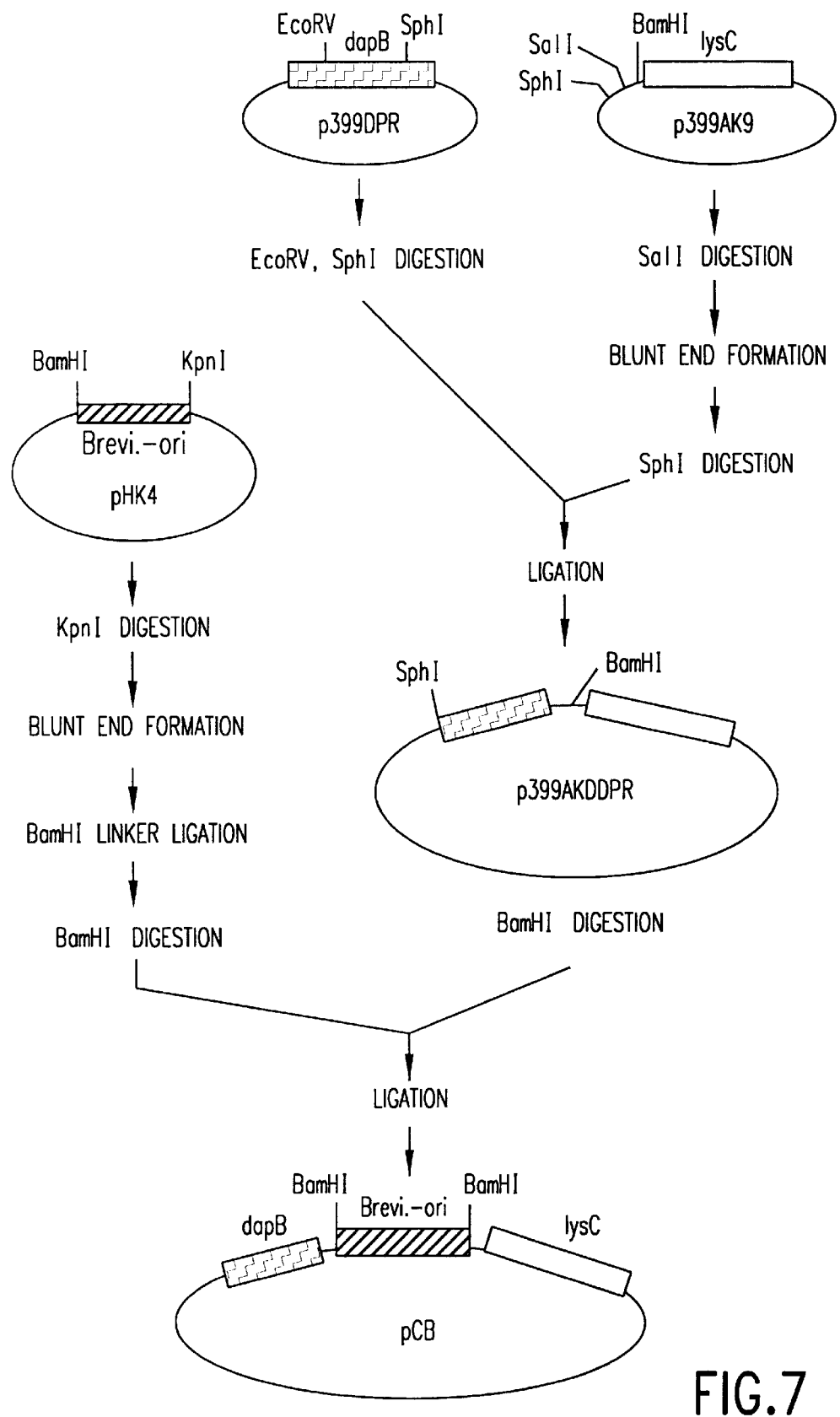
FIG. 7 illustrates a process of construction of a plasmid pCB comprising mutant lysC and dapB.

Next, Brevi.-ori was introduced into the obtained p399AKDDPR. The plasmid pHK4 containing Brevi.-ori was digested with a restriction enzyme KpnI (produced by Takara Shuzo), and cleaved edges were blunt-ended. Blunt end formation was performed by using DNA Blunting kit (produced by Takara Shuzo) in accordance with a designated method. After the blunt end formation, a phosphorylated BamHI linker (produced by Takara Shuzo) was ligated to make modification so that the DNA fragment corresponding to the Brevi.-ori portion might be excised from pHK4 by digestion with only BamHI. This plasmid was digested with BamHI, and the generated Brevi.-ori DNA fragment was ligated with p399AKDDPR having been also digested with BamHI to construct a plasmid containing mutant lysC and dapB autonomously replicable in coryneform bacteria. The constructed plasmid was designated as pCB. The process of construction of pCB is shown in FIG. 7.

Comparative Example 3

Construction of Plasmid Comprising Combination of dapA and dapB

The plasmid pCRDAPA comprising daDA was digested with KpnI and EcoRI to extract a DNA fragment containing dapA, and was ligated with the vector plasmid pHSG399 having been digested with KpNI and EcoRI. An obtained plasmid was designated as p399DPS.

On the other hand, the plasmid pCRDAPB comprising dapB was digested with S II and EcoRI to extract a DNA fragment of 2.0 kb containing a region coding for DDPR, and was ligated with p399DPS having been digested with SacII and EcoRI to construct a plasmid comprising a combination of dapA and dapB. The obtained plasmid was designated as p399AB.

Figure 8:
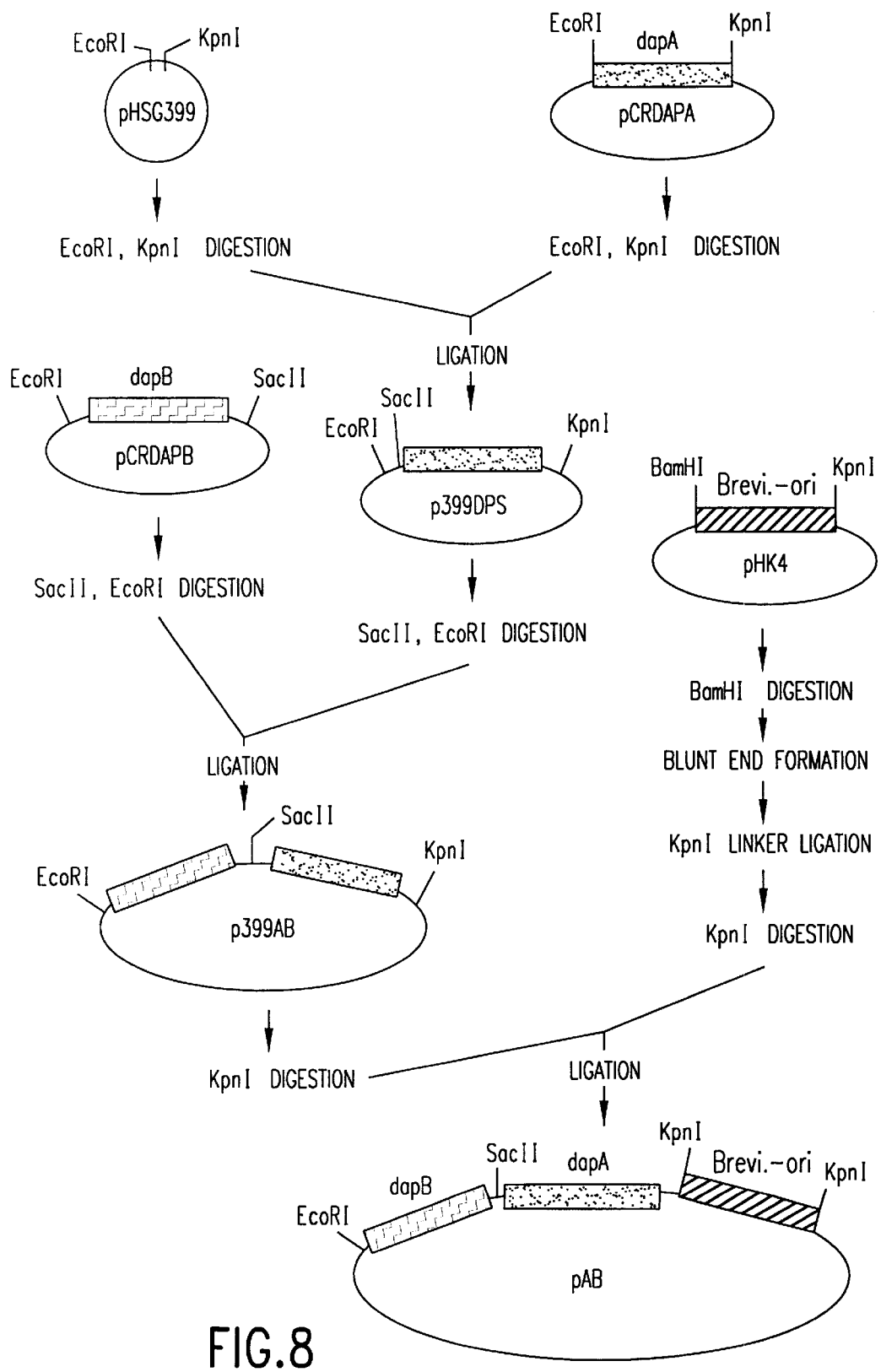
FIG. 8 illustrates a process of construction of a plasmid pAB comprising dapA, dapB and Brevi.-ori.

Next, Brevi.-ori was introduced into p399AB. pHK4 containing Brevi.-ori was digested with a restriction enzyme BamHI (produced by Takara Shuzo), and cleaved edges were blunt-ended. Blunt end formation was performed by using DNA Blunting kit (produced by Takara Shuzo) in accordance with a designated method. After the blunt end formation, a phosphorylated KpnI linker (produced by Takara Shuzo) was ligated to make modification so that the DNA fragment corresponding to the Brevi.-ori portion might be excised from pHK4 by digestion with only KpNI. This plasmid was digested with KpnI, and the generated Brevi.-ori DNA fragment was ligated with p399AB having been also digested with KDnI to construct a plasmid containing dapA and dapB autonomously replicable in coryneform bacteria. The constructed plasmid was designated as pAB. The process of construction of pAB is shown in FIG. 8.

Example 6

Construction of Plasmid Comprising Combination of Mutant lysC, dapA, and dapB p399DPS was digested with EcoRI and SphI and blunt-ended, followed by extraction of a dapA gene fragment. This fragment was ligated with the p399AK9 having been digested with SalI and blunt-ended to construct a plasmid p399CA in which mutant lysC and daiA co-existed.

The plasmid PCRDAPB comprising dapB was digested with EcoRI and blunt-ended, followed by digestion with SacI to extract a DNA fragment of 2.0 kb comprising dapB. The plasmid p399CA comprising dapA and mutant lysC was digested with SpeI and blunt-ended, and was thereafter digested with SacI and ligated with the extracted dapB fragment to obtain a plasmid comprising mutant lysC, dapA, and dapB. This plasmid was designated as p399CAB.

Figure 9:
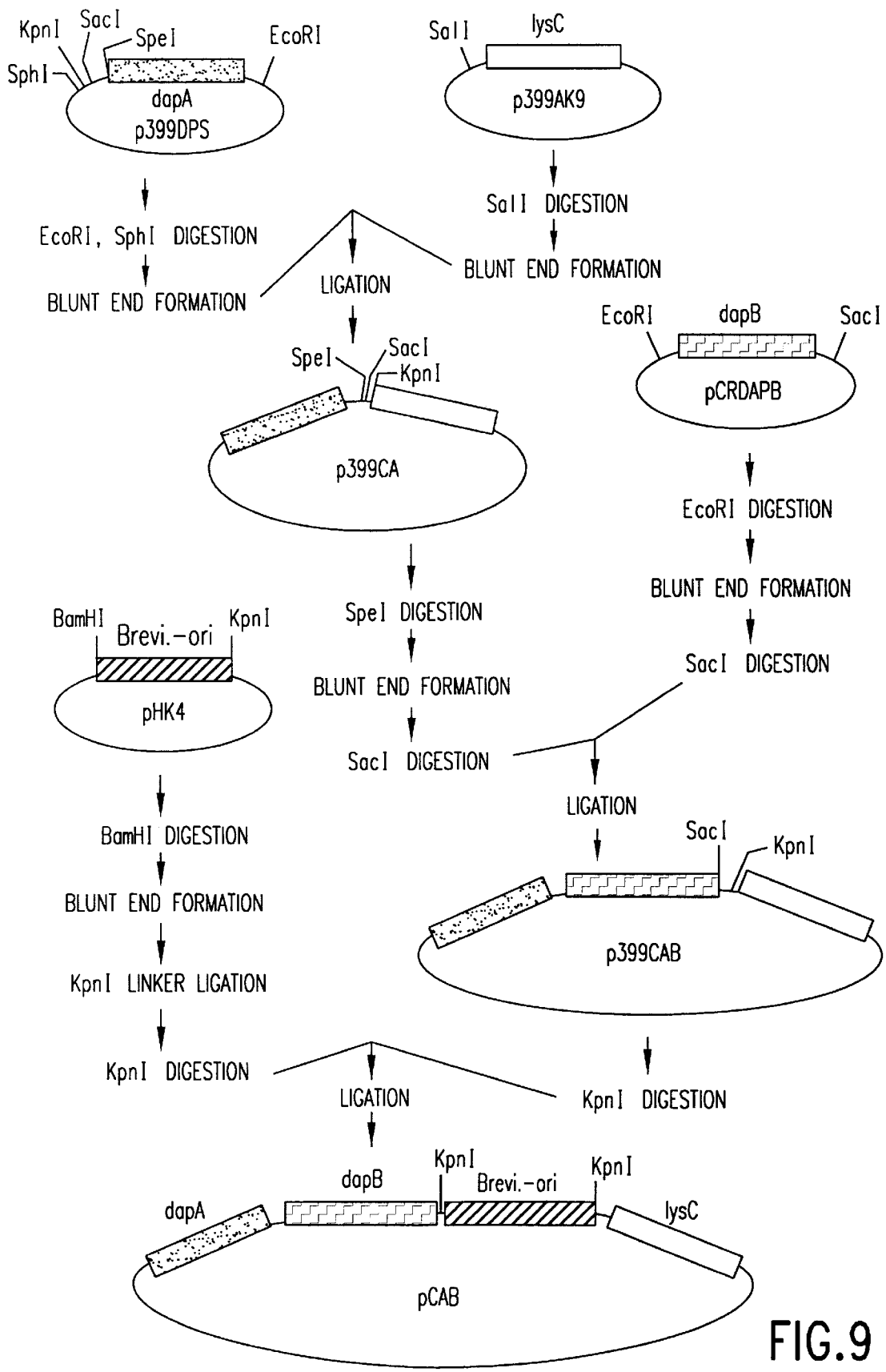
FIG. 9 illustrates a process of construction of a plasmid pCAB comprising mutant lysC, dapA, dapB, and Brevi.-ori.

Next, Brevi.-ori was introduced into p399CAB. The plasmid pHK4 comprising Brevi.-ori was digested with a restriction enzyme BamHI (produced by Takara Shuzo), and cleaved edges were blunt-ended. Blunt end formation was performed by using DNA Blunting kit (produced by Takara Shuzo) in accordance with a designated method. After the blunt end formation, a phosphorylated KpnI linker (produced by Takara Shuzo) was ligated to make modification so that the DNA fragment corresponding to the Brevi.-ori portion might be excised from pHK4 by digestion with only KpnI. This plasmid was digested with KpnI, and the generated Brevi.-ori DNA fragment was ligated with p399CAB having been also digested with KpnI to construct a plasmid comprising a combination of mutant lysC, dapA, and dapB autonomously replicable in coryneform bacteria. The constructed plasmid was designated as pCAB. The process of construction of pCAB is shown in FIG. 9.

Example 7

Figure 10:
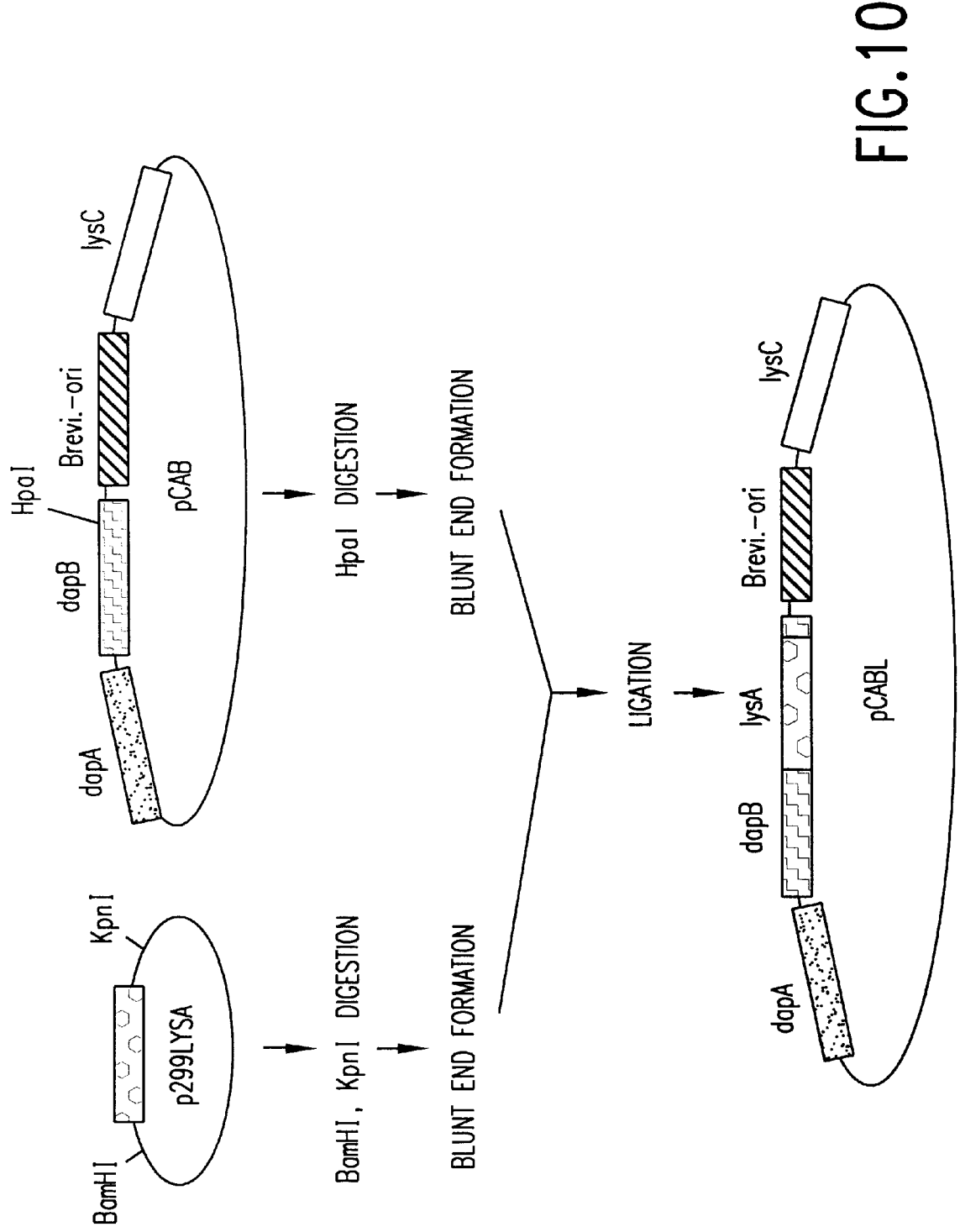
FIG. 10 illustrates a process of construction of a plasmid PCABL comprising mutant lysC, dapA, dapB, lysA, and Brevi.-ori.

Construction of Plasmid Comprising Combination of Mutant lysC, dapA, dapB, and lysA The plasmid p299LYSA comprising lysA was digested with KpnI and BamHI and blunt-ended, and then a lysA gene fragment was extracted. This fragment was ligated with pCAB having been digested with HpaI (produced by Takara Shuzo) and blunt-ended to construct a plasmid comprising a combination of mutant lysC, dapA, dapB, and lysA autonomously replicable in coryneform bacteria. The constructed plasmid was designated as pCABL. The process of construction of PCABL is shown in FIG. 10. It is noted that the lysA gene fragment is inserted into a HpaI site in a DNA fragment containing the dapB gene in pCABL, however, the HpaI site is located upstream from a promoter for the dapB gene (nucleotide numbers 611 to 616 in SEQ ID NO: 10), and the dapB gene is not decoupled.

Example 8

Construction of Plasmid Comprising aspC

Figure 11:
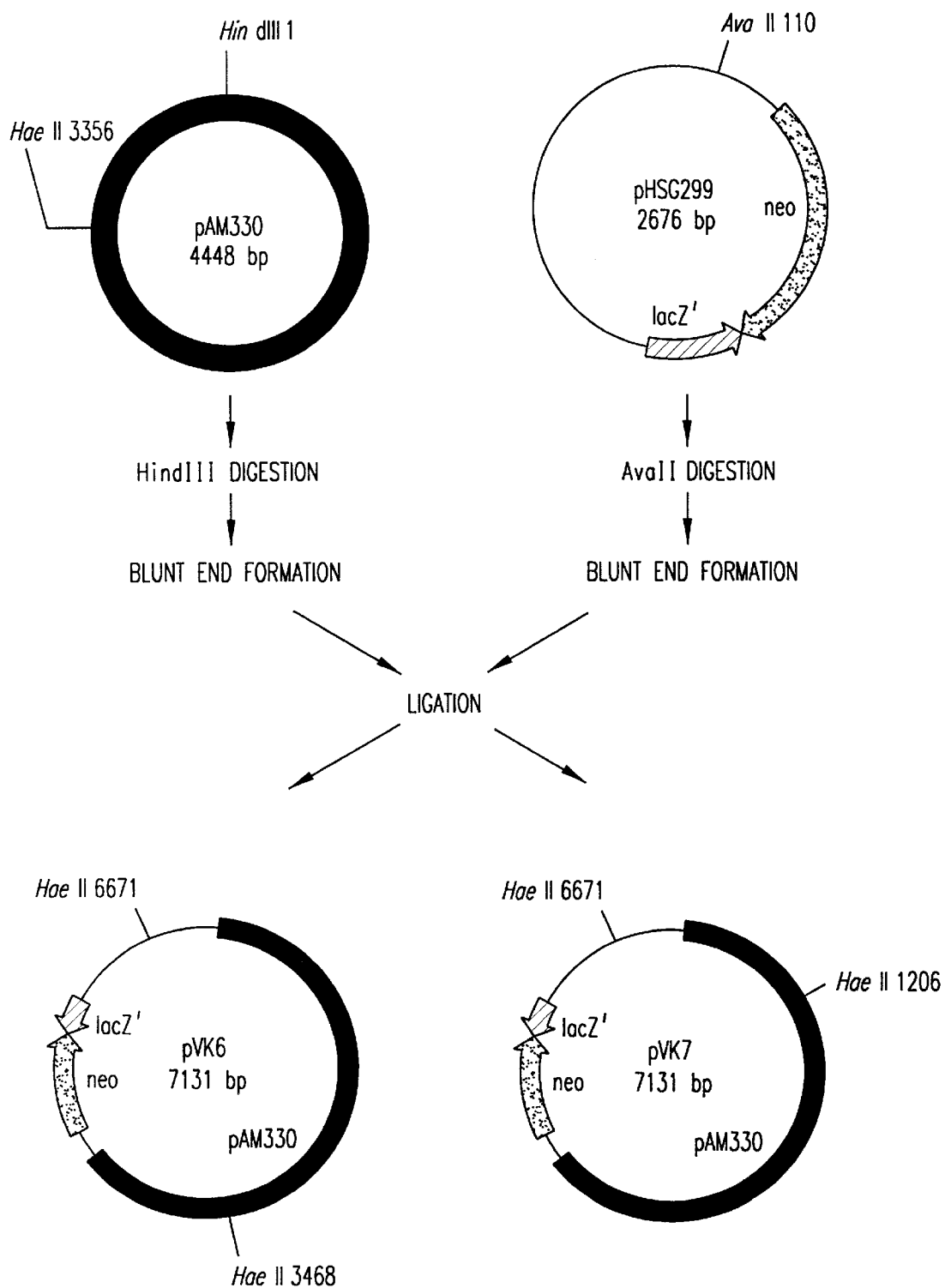
FIG. 11 illustrates a process of construction of novel cloning vectors for Coryneform bacteria, pVK6 and pVK7.

As a vector for introducing aspC into coryneform bacteria, a cloning vector for coryneform bacteria, pVK7 which was newly constructed was used. pVK7 was constructed by ligating pHSG299, a vector for *E. coli* (Kmr; Takeshita, S. et al., *Gene*, 61, 63–74 (1987)) with pAM330, a cryptic plasmid for *Brevibacterium lactofermentum* as described below. pAM330 was prepared from *Brevibacterium lactofermentum* ATCC 13869 strain. pHSG299 was digested with a restriction enzyme resulting one cleavage site, AvaII (produced by Takara Shuzo), blunt-ended by using T4 DNA polymerase, and ligated with pAM330 having been digested with HindIII (produced by Takara Shuzo) and blunt-ended by using T4 DNA polymerase. Depending on orientation of the inserted pAM330 in pHSG299, the two obtained plasmids were designated as pVK6 and pVK7, and pVK7 was used for the following experiments. pVK7 is autonomously replicable in both of *E. coli* and *Brevibacterium lactofermentum* and has a multiple cloning site originating from pHSG299 and lacZ'. The process of construction of pVK6 and pVK7 is shown in FIG. 11.

Figure 12:
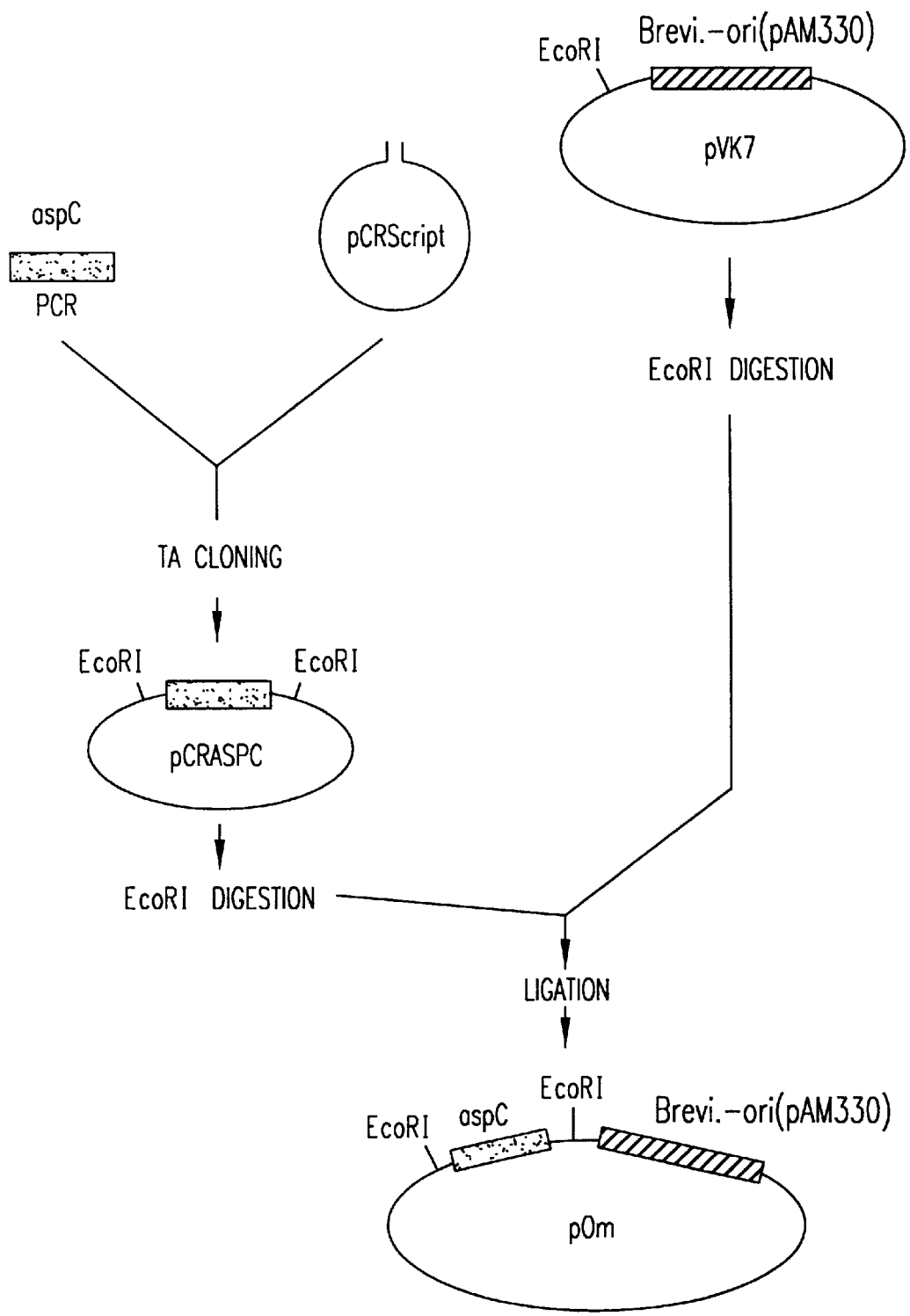
FIG. 12 illustrates a process of construction of a plasmid pOm comprising aspC.

With the constructed shuttle vector pVK7, aspC was ligated. pCRASPC was digested with a restriction enzyme EcoRI (produced by Takara Shuzo) and ligated with pVK7 having been also digested with EcoRI. Ligation of DNA was performed by using DNA Ligation kit (produced by Takara Shuzo). Among those in which a fragment of aspC was ligated with pVK7, one in which the fragment was inserted in the same orientation as the transcription orientation of lac promoter possessed by pVK7 was designated as pOm. The process of construction of pOm is shown in FIG. 12.

Example 9

Preparation of aspC from *Brevibacterium lactofermentum*

<1>Preparation of aspC originating from *Brevibacterium lactofermentum*

An aspartic acid auxotrophic strain 102-7 belonging to the genus Corynebacterium which was deficient in aspC activity (AAT activity) to be aspartic acid auxotrophic (I. Shiio and K. Ujikawa, *J. Biochem.*, 84, 647 (1978)), was transformed by introducing a gene library (International Publication No. WO95/23224) prepared by ligating various fragments of chromosomal DNA of wild type ATCC 13869 strain of *Brevibacterium lactofermentum* with a vector which functions in cells of bacteria belonging to the genus Corynebacterium. The obtained transformants were collected and washed with distilled water twice. Tens of thousands of the transformants were plated on agar plates of a minimum medium, Medium 10 containing no nitrogen source other than ammonia (I. Shiio and K. Ujikawa, *J. Biochem.*, 84, 647

(1978)) to obtain transformants which restored aspartic acid auxotrophy and showed excellent growth on the plate. Plasmid DNA was recovered from the obtained stain restoring the aspartic acid auxotrophy, and the obtained plasmid was designated as pAC. When the wild type ATCC 13869 strain of *Brevibacterium lactofermentum* was transformed with pAC, the aspC activity of the transformant was increased (Table 1). The activity determination was conducted according to a known method (see Sizer, I. W. and Jenkins, W. T., *Meth. Enzymol.*, vol. 5, 677–679 (1962)).

From the results, it was confirmed that the about 2.5 kb fragment of the chromosomal DNA of the ATCC 13869 strain on the plasmid DNA contained aspC of *Brevibacterium lactofermentum*.

TABLE 1

| Strain/Plasmid | aspC Activity (Relative value) |
| --- | --- |
| ATCC 13869 | 1.0 |
| ATCC 13869/pCABL | 8.9 |

<2>Analysis of aspC originating from *Brevibacterium lactofermentum*

Figure 13:
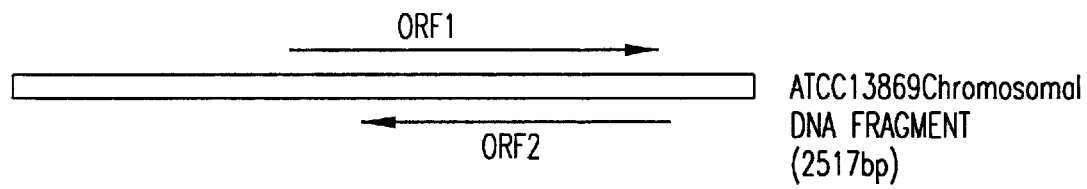
FIG. 13 illustrates two ORFs on an ATCC 13869 chromosomal DNA fragment.

A nucleotide sequence of the 2.5 kb DNA fragment was determined according to the dideoxy method of Sangar et al. (*Proc, Natl. Acad, Sci. USA,* 74, 5463 (1977)). The determined nucleotide sequence was shown in SEQ ID NO: 25. The nucleotide sequence was analyzed by using GENETYX-MAC Version 7.3 program (Software Kaihatsu KK). ORF (Open Reading Frame) search showed two ORFs which overlapped in the opposite orientation as shown in FIG. 13. The ORF of 432 amino acids or 426 amino acids which was encoded in the normal orientation between ATG of nucleotide number of 579 to 881 or 897 to 899 as an initiation codon and TAG of nucleotide number of 2175 to 2177 as a termination codon in the nucleotide sequence shown in SEQ ID NO: 25 was designated as ORF1. The ORF of 393 amino acids which was encoded in the reverse orientation between GTG complementary to CAC of nucleotide number of 2163 to 2165 as an initiation codon and TGA complementary to TCA of nucleotide number of 984 to 986 as a termination codon in the nucleotide sequence shown in SEQ ID NO: 25 was designated as ORF2.

<3>Determination of ORF coding for aspC

A DNA fragment which did not contained the full length of ORF2 and coded for the full length of ORF1 was amplified by PCR from pAC to confirm whether ORF codes for the AAT protein among the two ORFs. As for DNA primers used for amplification, synthetic DNAs of 23-mers having nucleotide sequences shown in SEQ ID NOs: 26 and 27 in Sequence Listing respectively were used on the basis of the sequence shown in SEQ ID NO: 25. Synthesis of DNA and PCR were performed in the same manner as described in Example 1. The amplified fragment of 2,062 bp of the nucleotide number 126 to 2,187 in the nucleotide sequence shown in SEQ ID NO: 25 was cloned into TA cloning vector pCR2.1 (produced by Invitrogen). The constructed plasmid was designated as pCRORF1.

In the same manner, a gene fragment of 1,543 bp of the nucleotide number 975 to 2,517 in the nucleotide sequence shown in SEQ ID NO: 25, which coded for the full length of only ORF2, was amplified and cloned. The constructed plasmid was designated as pCRORF2.

Figure 14:
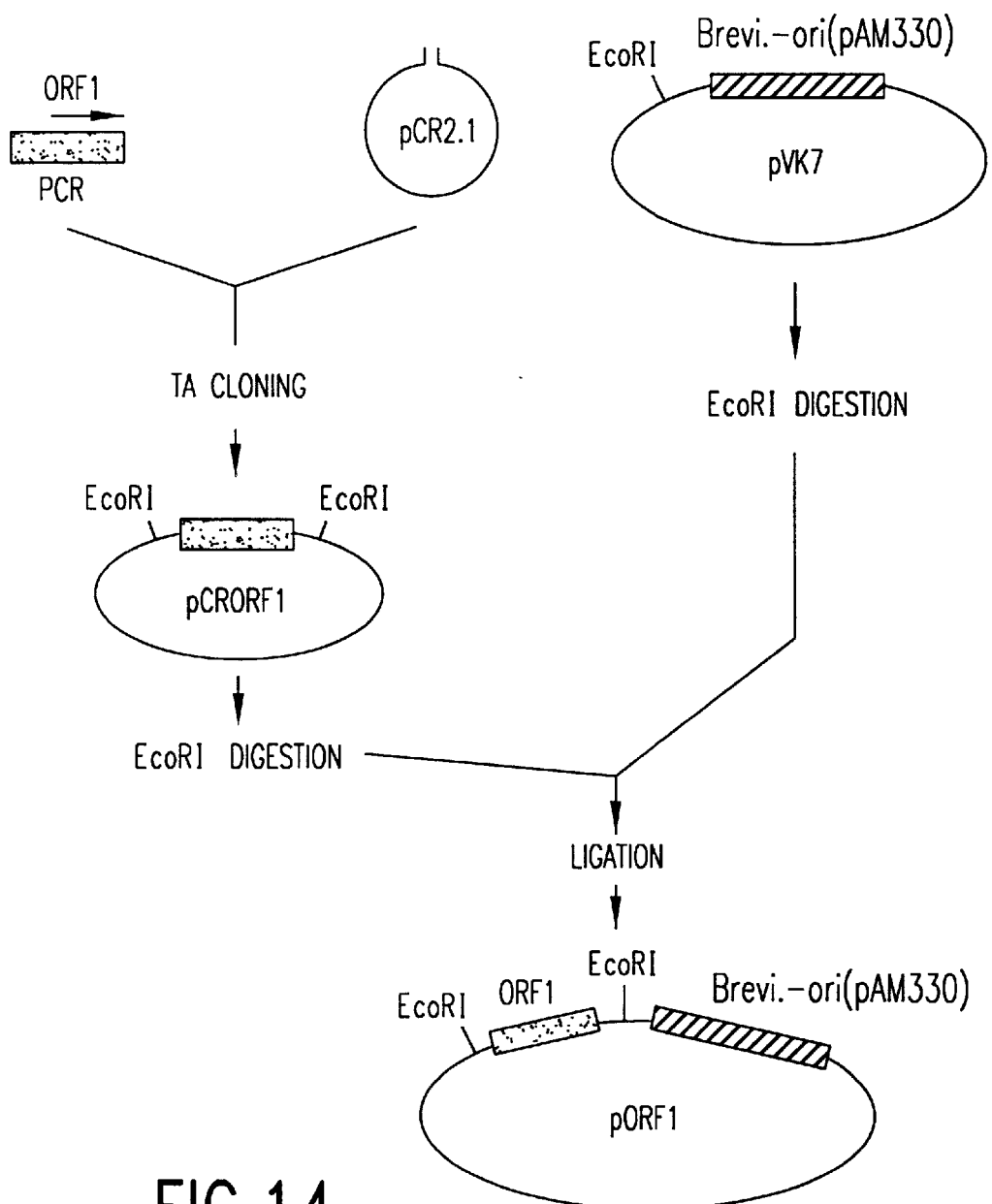
FIG. 14 illustrates a process of construction of pORF1.

To introduce the cloned DNA fragments into cells of bacteria belonging to the genus Corynebacterium, the DNA fragments were ligated with the shuttle vector described in Example 8. pCRORF1 was digested with a restriction enzyme EcoRI (produced by Takara Shuzo), and ligated with pVK7 having been digested with the restriction enzyme EcoRI. Ligation of DNA was performed by using DNA Ligation kit (produced by Takara Shuzo). The constructed plasmid was designated as pORF1. The process of construction of pORF1 is shown in FIG. 14.

In the same manner, pORF2 was constructed from pCRORF2 and pVK7.

The prepared pORF1 and pORF2 were introduced into cells of *Brevibacterium lactofermentum* wild type ATCC 13869 strain in the same manner as in Example 9. The aspC activities of ATCC 13869 and obtained plasmid-introduced strains ATCC 13869/pORFl and ATCC 13869/pORF2 were determined. The activity determination was conducted in the same manner as described in Example 1. As shown in Table 2, an increase in the aspC activity was observed only for ATCC 13869/pORF1, indicating that aspC is encoded by ORF1.

The nucleotide sequence of aspC of Brevibacterium lactofermentum determined by the above-mentioned experiments and an amino acid sequence deduced to be encoded by the nucleotide sequence are shown in SEQ ID NO: 30. Only the amino acid sequence is shown in SEQ ID NO: 31. Homology search on GENEBANK showed no homology to known amino acid sequences including AAT proteins originating from other organisms.

TABLE 2

| Strain/Plasmid | aspC Activity (Relative value) |
| --- | --- |
| ATCC 13869 | 1.0 |
| ATCC 13869/pORF1 | 10.1 |
| ATCC 13869/pORF2 | 1.2 |

Example 10

Introduction of Plasmids Comprising Genes for L-Lysine Biosynthesis into L-Lysine-Producing Bacterium of *Brevibacterium lactofermentum*

The PCABL(Cm$^r$) constructed in Example 7 was introduced into an L-lysine-producing bacterium AJ11082 (NRRL B-11470) of *Brevibacterium lactofermentum* respectively. The AJ11082 strain has a property of AEC resistance. The plasmid was introduced in accordance with an electric pulse method (Sugimoto et al., Japanese Patent Application Laid-open No. 2-207791). Transformants were selected based on a drug resistance marker possessed by the plasmid. Transformants were selected on a complete medium containing 5 µg/ml of chloramphenicol when a plasmid comprising a chloramphenicol resistance gene was introduced, or transformants were selected on a complete medium containing 25 µg/ml of kanamycin when a plasmid comprising a kanamycin resistance gene was introduced.

The transformant AJ11082/pCABL obtained as described above was transformed with plasmid pOm (KM$^r$) having aspC of *Eschericia coli* or pORF1 (Km$^r$) having aspC of *Brevibacterium lactofermentum*. Since pCABL uses pHM1519 as an replication origin in cells of *Brevibacterium lactofermentum* and a Cm resistance gene as a marker, and pOm uses pAM330 as an replication origin in cells of *Brevibacterium lactofermentum* and a Km resistance gene as a marker, both plasmids are stably harbored in cells of *Brevibacterium lactofermentum*. Thus, strains AJ11082/pCABL/pOm and AJ11082/pCABL/pORF1 in which a plasmid containing a gene participating in L-lysine biosynthesis and a plasmid containing aspC were obtained.

In the same manner as described above, p399AK9B (Cm'), pDPSB(Km'), PDPRB(Cm'), PLYSAB(Cm'), poM, PCRCAB(Km'), PAB(Cm'), PCB(Cm'), and PCAB(Cm') were introduced into the AJ11082 strain to obtain transformants in which mutant lysC, dapA, dapB, lysA or aspC was enhanced singly, or two or three of these genes were enhanced in combination.

Example 11

Determination of aspC activity of transformants

The aspC activities of the transformants AJ11082/pCABL, AJ11082/pCABL/pOm and AJ11082/pCABL/pORF1 were determined. The activity determination was conducted in the same manner as described in Example 9 <3>. As shown in Table 3, it was observed that the lac promoter on the pOm vector also functioned in *Brevibacterium lactofermentum* and the aspc activity of AJ11082/pCABL/pOm increased by about three times. A further increase in the aspc activity by about nine times was observed for AJ11082/pCABL/pORF1.

TABLE 3

| Strain/Plasmid | aspC Activity (Relative value) |
| --- | --- |
| AJ11082 | 1.0 |
| AJ11082/pOm | 3.2 |
| AJ11082/pORF1 | 10.1 |
| AJ11082/pCABL | 0.9 |
| AJ11082/pCABL/pOm | 2.9 |
| AJ11082/pCABL/pORF1 | 11.5 |

Example 12

Production of L-Lysine

Each of the transformants obtained in Example 10 was cultivated in an L-lysine-producing medium to evaluate its L-lysine productivity. The L-lysine-producing medium had the following composition.
[L-Lysine-producing medium]The following components other than calcium carbonate (in 1 L) were dissolved, and pH was adjusted at 8.0 with KOH. The medium was sterilized at 115° C. for 15 minutes, and calcium carbonate (50 g) having been separately sterilized in hot air in a dry state was thereafter added thereto.

| | |
| --- | --- |
| Glucose | 100 g |
| $(NH_4)_2SO_4$ | 55 g |
| $KH_2PO_4$ | 1 g |
| $MgSO_4.7H_2O$ | 1 g |
| Biotin | 500 μg |
| Thiamin | 2000 μg |
| $FeSO_4.7H_2O$ | 0.01 g |
| $MnSO_4.7H_2O$ | 0.01 g |
| Nicotinamide | 5 mg |
| Protein hydrolysate (Mamenou) | 30 ml |
| Calcium carbonate | 50 g |

Each of the various types of the transformants and the parent strain was inoculated to the medium having the composition described above to perform cultivation at 31.5° C. with reciprocating shaking. The amount of produced L-lysine after 40 or 72 hours of cultivation, and the growth after 72 hours (ODs62) are shown in Table 4. In the table, lysC* represents mutant lysC. The growth was quantitatively determined by measuring OD at 562 nm after 101-fold dilution.

TABLE 4

Accumulation of L-Lysine after Cultivation for 40 or 72 Hours

| Bacterial strain/plasmid | Introduced gene | Amount of produced L-lysine (g/L) | | Growth $(OD_{562}/101)$ |
| --- | --- | --- | --- | --- |
| | | after 40 hrs | after 72 hrs | |
| AJ11082 | | 22.0 | 29.8 | 0.450 |
| AJ11082/p399AK9B | lysC* | 16.8 | 34.5 | 0.398 |
| AJ11082/pDPSB | dapA | 18.7 | 33.8 | 0.410 |
| AJ11082/pDPRB | dapB | 19.9 | 29.9 | 0.445 |
| AJ11082/pLYSAB | lysA | 19.8 | 32.5 | 0.356 |
| AJ11082/pOm | aspC(E) [Note 1] | 21.8 | 30.9 | 0.457 |
| AJ11082/pOm | aspC(B) [Note 2] | 21.5 | 31.2 | 0.450 |
| AJ11082/pCRCAB | lysC*, dapA | 19.7 | 36.5 | 0.360 |
| AJ11082/pAB | dapA, dapB | 19.0 | 34.8 | 0.390 |
| AJ11082/pCB | lysC*, dapB | 23.3 | 35.0 | 0.440 |
| AJ11082/pCAB | lysC*, dapA, dapB | 23.0 | 45.0 | 0.425 |
| AJ11082/pCABL | lysC*, dapA, dapB, lysA | 26.2 | 46.5 | 0.379 |
| AJ11082/pCABL/pOm | lysC*, dapA, dapB, lysA, aspC(E) | 26.7 | 47.6 | 0.415 |
| AJ11082/pCABL/pORF1 | lysC*, dapA, dapB, lysA, aspC(B) | 27.1 | 48.8 | 0.410 |

Note 1: aspC of *Escherichia coli*
Note 2: aspC of *Brevibacterium lactofermentum*

As shown in the above, when mutant lysC, dapA, dapB, lysA or aspC was enhanced singly, the amount of produced L-lysine was larger than or equivalent to that produced by the parent strain after 72 hours of cultivation, however, the amount of produced L-lysine was smaller than that produced by the parent strain after 40 hours of cultivation. Namely, the L-lysine-producing speed was lowered in cultivation for a short period. Similarly, when mutant lysC and dapA, or dapA and dapB were enhanced in combination, the amount of produced L-lysine was larger than that produced by the parent strain after 72 hours of cultivation, however, the amount of produced L-lysine was smaller than that produced by the parent strain after 40 hours of cultivation. Thus the L-lysine-producing speed was lowered.

On the contrary, in the case of the strain in which dapB was enhanced together with mutant lysC, the strain in which three of mutant lysc, dapA and dapB were enhanced, and the strain in which four of mutant lysC, dapA, dapB and lysA were enhanced, the accumulated amount of L-lysine was improved in both of the short period and the long period of cultivation.

In the case of the strain in which five of mutant lysC, dapA, dapB, lysA, and aspC of *Escherichia coli* were enhanced, and the strain in which five of mutant lysC, dapA, dapB, lysA, and aspC of *Brevibacterium lactofermentum* were enhanced, the L-lysine productivity was further improved in any of the periods. The extent of the improvement of the latter was larger than that of the former.

What is claimed is:

1. A recombinant DNA autonomously replicable in cells of coryneform bacteria, comprising a DNA sequence coding for an aspartokinase in which feedback inhibition by L-lysine and L-threonine is desensitized, a DNA sequence coding for a dihydrodipicolinate reductase, a DNA sequence coding for dihydrodipicolinate synthase, a DNA sequence coding for diaminopimelate decarboxylase, and a DNA sequence coding for aspartate aminotransferase.

2. The recombinant DNA according to claim 1, wherein said aspartokiniase in which feedback inhibition by L-lysine and L-threonine is desensitized is an aspartokinase originating from coryneform bacteria, and wherein said aspartokinase is a mutant aspartokinase in which an amino acid residue corresponding to a 279th alanine residue as counted from its N-terminal in the amino acid sequence shown in SEQ ID NO: 5 is changed into an amino acid residue other than alanine and other than an acidic amino acid in its α-subunit, and an amino acid residue corresponding to a 30th alanine residue as counted from its N-terminal in the amino acid sequence shown in SEQ ID NO: 7 is changed into an amino acid residue other than alanine and other than an acidic amino acid in its β-subunit.

3. The recombinant DNA according to claim 1, wherein said DNA sequence coding for the dihydrodipicolinate reductase codes for an amino acid sequence shown in SEQ ID NO: 15.

4. The recombinant DNA according to claim 1, wherein said DNA sequence coding for the dihydrodipicolinate synthase codes for an amino acid sequence shown in SEQ ID NO: 11.

5. The recombinant DNA according to claim 1, wherein said DNA sequence coding for the diaminopimelate decarboxylase codes for an amino acid sequence shown in SEQ ID NO: 19.

6. The recombinant DNA according to claim 1, wherein said DNA sequence coding for the aspartate aminotransferase codes for an amino acid sequence shown in SEQ ID NO: 24 or 31.

7. A coryneform bacterium harboring an aspartokinase in which feedback inhibition by L-lysine and L-threonine is desensitized, and comprising a DNA sequence coding for a dihydrodipicolinate reductase, a DNA sequence coding for dihydrodipicolinate synthase, a DNA sequence coding for diaminopimelate decarboxylase and a DNA sequence coding for aspartate aminotransferase, intracellular activities of the dihydrodipicolinate reductase, the dihydrodipicolinate synthase, the diaminopimelate decarboxylase and the aspartate aminotransferase being raised.

8. The coryneform bacterium according to claim 7, transformed by introduction of the recombinant DNA as defined in claim 1.

9. A method for producing L-lysine comprising the steps of cultivating said coryneform bacterium as defined in claim 8 in a medium to allow L-lysine to be produced and accumulated in a culture of the bacterium, and collecting L-lysine from the culture.

10. An isolated DNA coding for a protein comprising an amino acid sequence shown in SEQ ID NO: 31.

11. The DNA according to claim 10, which comprises a nucleotide sequence of nucleotide numbers 879 to 2174 in a nucleotide sequence shown in SEQ ID NO: 30.

12. A vector pVK7, which is autonomously replicable in cells of *Escherichia coli* and *Brevibacterium lactofermentum*, and comprising a multiple cloning site and lacZ'.

* * * * *

SEQUENCE LISTING (1) GENERAL INFORMATION:

(iii) NUMBER OF SEQUENCES: 31

(2) INFORMATION FOR SEQ ID NO:1:

(i) SEQUENCE CHARACTERISTICS:
       (A) LENGTH: 23 bases
       (B) TYPE: nucleic acid
       (C) STRANDEDNESS: single
       (D) TOPOLOGY: linear (ii) MOLECULE TYPE: other nucleic acid
       (A) DESCRIPTION:   /desc = "synthetic DNA"

(iv) ANTI-SENSE: no (xi) SEQUENCE DESCRIPTION: SEQ ID NO: 1:

TCGCGAAGTA GCACCTGTCA CTT                                              23

(2) INFORMATION FOR SEQ ID NO:2:

(i) SEQUENCE CHARACTERISTICS:
       (A) LENGTH: 21 bases
       (B) TYPE: nucleic acid
       (C) STRANDEDNESS: single
       (D) TOPOLOGY: linear (ii) MOLECULE TYPE: other nucleic acid
       (A) DESCRIPTION:   /desc = "synthetic DNA"

(iv) ANTI-SENSE: yes (xi) SEQUENCE DESCRIPTION: SEQ ID NO: 2:

ACGGAATTCA ATCTTACGGC C                                                21

(2) INFORMATION FOR SEQ ID NO:3:

(i) SEQUENCE CHARACTERISTICS:
       (A) LENGTH: 1643 bases
       (B) TYPE: nucleic acid
       (C) STRANDEDNESS: double
       (D) TOPOLOGY: linear (ii) MOLECULE TYPE: genomic DNA (vi) ORIGINAL SOURCE:
       (A) ORGANISM: Brevibacterium lactofermentum
       (B) STRAIN: ATCC 13869

(xi) SEQUENCE DESCRIPTION: SEQ ID NO: 3:

TCGCGAAGTA GCACCTGTCA CTTTTGTCTC AAATATTAAA TCGAATATCA ATATACGGTC       60

TGTTTATTGG AACGCATCCC AGTGGCTGAG ACGCATCCGC TAAAGCCCCA GGAACCCTGT      120

GCAGAAAGAA AACACTCCTC TGGCTAGGTA GACACAGTTT ATAAAGGTAG AGTTGAGCGG      180

GTAACTGTCA GCACGTAGAT CGAAAGGTGC ACAAAGGTGG CCCTGGTCGT ACAGAAATAT      240

GGCGGTTCCT CGCTTGAGAG TGCGGAACGC ATTAGAAACG TCGCTGAACG GATCGTTGCC      300

ACCAAGAAGG CTGGAAATGA TGTCGTGGTT GTCTGCTCCG CAATGGGAGA CACCACGGAT      360

GAACTTCTAG AACTTGCAGC GGCAGTGAAT CCCGTTCCGC CAGCTCGTGA AATGGATATG      420

CTCCTGACTG CTGGTGAGCG TATTTCTAAC GCTCTCGTCG CCATGGCTAT TGAGTCCCTT      480

GGCGCAGAAG CTCAATCTTT CACTGGCTCT CAGGCTGGTG TGCTCACCAC CGAGCGCCAC      540

GGAAACGCAC GCATTGTTGA CGTCACACCG GGTCGTGTGC GTGAAGCACT CGATGAGGGC      600

-continued

```
AAGATCTGCA TTGTTGCTGG TTTTCAGGGT GTTAATAAAG AAACCCGCGA TGTCACCACG      660

TTGGGTCGTG GTGGTTCTGA CACCACTGCA GTTGCGTTGG CAGCTGCTTT GAACGCTGAT      720

GTGTGTGAGA TTTACTCGGA CGTTGACGGT GTGTATACCG CTGACCCGCG CATCGTTCCT      780

AATGCACAGA AGCTGGAAAA GCTCAGCTTC GAAGAAATGC TGGAACTTGC TGCTGTTGGC      840

TCCAAGATTT TGGTGCTGCG CAGTGTTGAA TACGCTCGTG CATTCAATGT GCCACTTCGC      900

GTACGCTCGT CTTATAGTAA TGATCCCGGC ACTTTGATTG CCGGCTCTAT GGAGGATATT      960

CCTGTGGAAG AAGCAGTCCT TACCGGTGTC GCAACCGACA AGTCCGAAGC CAAAGTAACC     1020

GTTCTGGGTA TTTCCGATAA GCCAGGCGAG GCTGCCAAGG TTTTCCGTGC GTTGGCTGAT     1080

GCAGAAATCA ACATTGACAT GGTTCTGCAG AACGTCTCCT CTGTGGAAGA CGGCACCACC     1140

GACATCACGT TCACCTGCCC TCGCGCTGAC GGACGCCGTG CGATGGAGAT CTTGAAGAAG     1200

CTTCAGGTTC AGGGCAACTG GACCAATGTG CTTTACGACG ACCAGGTCGG CAAAGTCTCC     1260

CTCGTGGGTG CTGGCATGAA GTCTCACCCA GGTGTTACCG CAGAGTTCAT GGAAGCTCTG     1320

CGCGATGTCA ACGTGAACAT CGAATTGATT TCCACCTCTG AGATCCGCAT TTCCGTGCTG     1380

ATCCGTGAAG ATGATCTGGA TGCTGCTGCA CGTGCATTGC ATGAGCAGTT CCAGCTGGGC     1440

GGCGAAGACG AAGCCGTCGT TTATGCAGGC ACCGGACGCT AAAGTTTTAA AGGAGTAGTT     1500

TTACAATGAC CACCATCGCA GTTGTTGGTG CAACCGGCCA GGTCGGCCAG GTTATGCGCA     1560

CCCTTTTGGA AGAGCGCAAT TTCCCAGCTG ACACTGTTCG TTTCTTTGCT TCCCCGCGTT     1620

CCGCAGGCCG TAAGATTGAA TTC                                             1643
```

(2) INFORMATION FOR SEQ ID NO:4:

(i) SEQUENCE CHARACTERISTICS:
        (A) LENGTH: 1643 bases
        (B) TYPE: nucleic acid
        (C) STRANDEDNESS: double
        (D) TOPOLOGY: linear (ii) MOLECULE TYPE: genomic DNA (vi) ORIGINAL SOURCE:
        (A) ORGANISM: Brevibacterium lactofermentum
        (B) STRAIN: ATCC 13869

(ix) FEATURE:
        (A) NAME/KEY: CDS
        (B) LOCATION: 217..1482

(xi) SEQUENCE DESCRIPTION: SEQ ID NO: 4:

```
TCGCGAAGTA GCACCTGTCA CTTTTGTCTC AAATATTAAA TCGAATATCA ATATACGGTC       60

TGTTTATTGG AACGCATCCC AGTGGCTGAG ACGCATCCGC TAAAGCCCCA GGAACCCTGT      120

GCAGAAAGAA AACACTCCTC TGGCTAGGTA GACACAGTTT ATAAAGGTAG AGTTGAGCGG      180

GTAACTGTCA GCACGTAGAT CGAAAGGTGC ACAAAG GTG GCC CTG GTC GTA CAG       234
                                       Met Ala Leu Val Val Gln
                                         1               5

AAA TAT GGC GGT TCC TCG CTT GAG AGT GCG GAA CGC ATT AGA AAC GTC       282
Lys Tyr Gly Gly Ser Ser Leu Glu Ser Ala Glu Arg Ile Arg Asn Val
         10                  15                  20

GCT GAA CGG ATC GTT GCC ACC AAG AAG GCT GGA AAT GAT GTC GTG GTT       330
Ala Glu Arg Ile Val Ala Thr Lys Lys Ala Gly Asn Asp Val Val Val
     25                  30                  35

GTC TGC TCC GCA ATG GGA GAC ACC ACG GAT GAA CTT CTA GAA CTT GCA       378
Val Cys Ser Ala Met Gly Asp Thr Thr Asp Glu Leu Leu Glu Leu Ala
 40                  45                  50

GCG GCA GTG AAT CCC GTT CCG CCA GCT CGT GAA ATG GAT ATG CTC CTG       426
```

```
Ala Ala Val Asn Pro Val Pro Pro Ala Arg Glu Met Asp Met Leu Leu
 55              60              65              70

ACT GCT GGT GAG CGT ATT TCT AAC GCT CTC GTC GCC ATG GCT ATT GAG    474
Thr Ala Gly Glu Arg Ile Ser Asn Ala Leu Val Ala Met Ala Ile Glu
                 75              80              85

TCC CTT GGC GCA GAA GCT CAA TCT TTC ACT GGC TCT CAG GCT GGT GTG    522
Ser Leu Gly Ala Glu Ala Gln Ser Phe Thr Gly Ser Gln Ala Gly Val
                 90              95             100

CTC ACC ACC GAG CGC CAC GGA AAC GCA CGC ATT GTT GAC GTC ACA CCG    570
Leu Thr Thr Glu Arg His Gly Asn Ala Arg Ile Val Asp Val Thr Pro
            105             110             115

GGT CGT GTG CGT GAA GCA CTC GAT GAG GGC AAG ATC TGC ATT GTT GCT    618
Gly Arg Val Arg Glu Ala Leu Asp Glu Gly Lys Ile Cys Ile Val Ala
        120             125             130

GGT TTT CAG GGT GTT AAT AAA GAA ACC CGC GAT GTC ACC ACG TTG GGT    666
Gly Phe Gln Gly Val Asn Lys Glu Thr Arg Asp Val Thr Thr Leu Gly
135             140             145             150

CGT GGT GGT TCT GAC ACC ACT GCA GTT GCG TTG GCA GCT GCT TTG AAC    714
Arg Gly Gly Ser Asp Thr Thr Ala Val Ala Leu Ala Ala Ala Leu Asn
                155             160             165

GCT GAT GTG TGT GAG ATT TAC TCG GAC GTT GAC GGT GTG TAT ACC GCT    762
Ala Asp Val Cys Glu Ile Tyr Ser Asp Val Asp Gly Val Tyr Thr Ala
                170             175             180

GAC CCG CGC ATC GTT CCT AAT GCA CAG AAG CTG GAA AAG CTC AGC TTC    810
Asp Pro Arg Ile Val Pro Asn Ala Gln Lys Leu Glu Lys Leu Ser Phe
            185             190             195

GAA GAA ATG CTG GAA CTT GCT GCT GTT GGC TCC AAG ATT TTG GTG CTG    858
Glu Glu Met Leu Glu Leu Ala Ala Val Gly Ser Lys Ile Leu Val Leu
        200             205             210

CGC AGT GTT GAA TAC GCT CGT GCA TTC AAT GTG CCA CTT CGC GTA CGC    906
Arg Ser Val Glu Tyr Ala Arg Ala Phe Asn Val Pro Leu Arg Val Arg
215             220             225             230

TCG TCT TAT AGT AAT GAT CCC GGC ACT TTG ATT GCC GGC TCT ATG GAG    954
Ser Ser Tyr Ser Asn Asp Pro Gly Thr Leu Ile Ala Gly Ser Met Glu
                235             240             245

GAT ATT CCT GTG GAA GAA GCA GTC CTT ACC GGT GTC GCA ACC GAC AAG   1002
Asp Ile Pro Val Glu Glu Ala Val Leu Thr Gly Val Ala Thr Asp Lys
            250             255             260

TCC GAA GCC AAA GTA ACC GTT CTG GGT ATT TCC GAT AAG CCA GGC GAG   1050
Ser Glu Ala Lys Val Thr Val Leu Gly Ile Ser Asp Lys Pro Gly Glu
        265             270             275

GCT GCC AAG GTT TTC CGT GCG TTG GCT GAT GCA GAA ATC AAC ATT GAC   1098
Ala Ala Lys Val Phe Arg Ala Leu Ala Asp Ala Glu Ile Asn Ile Asp
280             285             290

ATG GTT CTG CAG AAC GTC TCC TCT GTG GAA GAC GGC ACC ACC GAC ATC   1146
Met Val Leu Gln Asn Val Ser Ser Val Glu Asp Gly Thr Thr Asp Ile
295             300             305             310

ACG TTC ACC TGC CCT CGC GCT GAC GGA CGC CGT GCG ATG GAG ATC TTG   1194
Thr Phe Thr Cys Pro Arg Ala Asp Gly Arg Arg Ala Met Glu Ile Leu
                315             320             325

AAG AAG CTT CAG GTT CAG GGC AAC TGG ACC AAT GTG CTT TAC GAC GAC   1242
Lys Lys Leu Gln Val Gln Gly Asn Trp Thr Asn Val Leu Tyr Asp Asp
            330             335             340

CAG GTC GGC AAA GTC TCC CTC GTG GGT GCT GGC ATG AAG TCT CAC CCA   1290
Gln Val Gly Lys Val Ser Leu Val Gly Ala Gly Met Lys Ser His Pro
        345             350             355

GGT GTT ACC GCA GAG TTC ATG GAA GCT CTG CGC GAT GTC AAC GTG AAC   1338
Gly Val Thr Ala Glu Phe Met Glu Ala Leu Arg Asp Val Asn Val Asn
360             365             370

ATC GAA TTG ATT TCC ACC TCT GAG ATC CGC ATT TCC GTG CTG ATC CGT   1386
```

-continued

```
Ile Glu Leu Ile Ser Thr Ser Glu Ile Arg Ile Ser Val Leu Ile Arg
375                 380                 385                 390

GAA GAT GAT CTG GAT GCT GCT GCA CGT GCA TTG CAT GAG CAG TTC CAG     1434
Glu Asp Asp Leu Asp Ala Ala Ala Arg Ala Leu His Glu Gln Phe Gln
                395                 400                 405

CTG GGC GGC GAA GAC GAA GCC GTC GTT TAT GCA GGC ACC GGA CGC TAA     1482
Leu Gly Gly Glu Asp Glu Ala Val Val Tyr Ala Gly Thr Gly Arg
                410                 415                 420

AGTTTTAAAG GAGTAGTTTT ACAATGACCA CCATCGCAGT TGTTGGTGCA ACCGGCCAGG   1542

TCGGCCAGGT TATGCGCACC CTTTTGGAAG AGCGCAATTT CCCAGCTGAC ACTGTTCGTT   1602

TCTTTGCTTC CCCGCGTTCC GCAGGCCGTA AGATTGAATT C                       1643
```

(2) INFORMATION FOR SEQ ID NO:5:

(i) SEQUENCE CHARACTERISTICS:
        (A) LENGTH: 421 amino acids
        (B) TYPE: amino acid
        (D) TOPOLOGY: linear (ii) MOLECULE TYPE: protein (xi) SEQUENCE DESCRIPTION: SEQ ID NO: 5:

```
Met Ala Leu Val Val Gln Lys Tyr Gly Gly Ser Ser Leu Glu Ser Ala
 1               5                  10                  15

Glu Arg Ile Arg Asn Val Ala Glu Arg Ile Val Ala Thr Lys Lys Ala
                20                  25                  30

Gly Asn Asp Val Val Val Cys Ser Ala Met Gly Asp Thr Thr Asp
            35                  40                  45

Glu Leu Leu Glu Leu Ala Ala Ala Val Asn Pro Val Pro Pro Ala Arg
     50                  55                  60

Glu Met Asp Met Leu Leu Thr Ala Gly Glu Arg Ile Ser Asn Ala Leu
 65                  70                  75                  80

Val Ala Met Ala Ile Glu Ser Leu Gly Ala Glu Ala Gln Ser Phe Thr
                85                  90                  95

Gly Ser Gln Ala Gly Val Leu Thr Thr Glu Arg His Gly Asn Ala Arg
            100                 105                 110

Ile Val Asp Val Thr Pro Gly Arg Val Arg Glu Ala Leu Asp Glu Gly
        115                 120                 125

Lys Ile Cys Ile Val Ala Gly Phe Gln Gly Val Asn Lys Glu Thr Arg
    130                 135                 140

Asp Val Thr Thr Leu Gly Arg Gly Gly Ser Asp Thr Thr Ala Val Ala
145                 150                 155                 160

Leu Ala Ala Ala Leu Asn Ala Asp Val Cys Glu Ile Tyr Ser Asp Val
                165                 170                 175

Asp Gly Val Tyr Thr Ala Asp Pro Arg Ile Val Pro Asn Ala Gln Lys
            180                 185                 190

Leu Glu Lys Leu Ser Phe Glu Glu Met Leu Glu Leu Ala Ala Val Gly
        195                 200                 205

Ser Lys Ile Leu Val Leu Arg Ser Val Glu Tyr Ala Arg Ala Phe Asn
    210                 215                 220

Val Pro Leu Arg Val Arg Ser Ser Tyr Ser Asn Asp Pro Gly Thr Leu
225                 230                 235                 240

Ile Ala Gly Ser Met Glu Asp Ile Pro Val Glu Glu Ala Val Leu Thr
                245                 250                 255

Gly Val Ala Thr Asp Lys Ser Glu Ala Lys Val Thr Val Leu Gly Ile
            260                 265                 270
```

-continued

```
Ser Asp Lys Pro Gly Glu Ala Ala Lys Val Phe Arg Ala Leu Ala Asp
        275                 280                 285

Ala Glu Ile Asn Ile Asp Met Val Leu Gln Asn Val Ser Ser Val Glu
        290                 295                 300

Asp Gly Thr Thr Asp Ile Thr Phe Thr Cys Pro Arg Ala Asp Gly Arg
305                 310                 315                 320

Arg Ala Met Glu Ile Leu Lys Lys Leu Gln Val Gln Gly Asn Trp Thr
                325                 330                 335

Asn Val Leu Tyr Asp Asp Gln Val Gly Lys Val Ser Leu Val Gly Ala
            340                 345                 350

Gly Met Lys Ser His Pro Gly Val Thr Ala Glu Phe Met Glu Ala Leu
        355                 360                 365

Arg Asp Val Asn Val Asn Ile Glu Leu Ile Ser Thr Ser Glu Ile Arg
    370                 375                 380

Ile Ser Val Leu Ile Arg Glu Asp Asp Leu Asp Ala Ala Ala Arg Ala
385                 390                 395                 400

Leu His Glu Gln Phe Gln Leu Gly Gly Glu Asp Glu Ala Val Val Tyr
                405                 410                 415

Ala Gly Thr Gly Arg
            420
```

(2) INFORMATION FOR SEQ ID NO:6:

(i) SEQUENCE CHARACTERISTICS:
        (A) LENGTH: 1643 bases
        (B) TYPE: nucleic acid
        (C) STRANDEDNESS: double
        (D) TOPOLOGY: linear (ii) MOLECULE TYPE: genomic DNA (vi) ORIGINAL SOURCE:
        (A) ORGANISM: Brevibacterium lactofermentum
        (B) STRAIN: ATCC 13869

(ix) FEATURE:
        (A) NAME/KEY: CDS
        (B) LOCATION: 964..1482

(xi) SEQUENCE DESCRIPTION: SEQ ID NO: 6:

```
TCGCGAAGTA GCACCTGTCA CTTTTGTCTC AAATATTAAA TCGAATATCA ATATACGGTC    60

TGTTTATTGG AACGCATCCC AGTGGCTGAG ACGCATCCGC TAAAGCCCCA GGAACCCTGT   120

GCAGAAAGAA AACACTCCTC TGGCTAGGTA GACACAGTTT ATAAAGGTAG AGTTGAGCGG   180

GTAACTGTCA GCACGTAGAT CGAAGGTGCA CAAAGGTGG CCCTGGTCGT ACAGAAATAT    240

GGCGGTTCCT CGCTTGAGAG TGCGGAACGC ATTAGAAACG TCGCTGAACG GATCGTTGCC   300

ACCAAGAAGG CTGGAAATGA TGTCGTGGTT GTCTGCTCCG CAATGGGAGA CACCACGGAT   360

GAACTTCTAG AACTTGCAGC GGCAGTGAAT CCCGTTCCGC CAGCTCGTGA AATGGATATG   420

CTCCTGACTG CTGGTGAGCG TATTTCTAAC GCTCTCGTCG CCATGGCTAT TGAGTCCCTT   480

GGCGCAGAAG CTCAATCTTT CACTGGCTCT CAGGCTGGTG TGCTCACCAC CGAGCGCCAC   540

GGAAACGCAC GCATTGTTGA CGTCACACCG GGTCGTGTGC GTGAAGCACT CGATGAGGGC   600

AAGATCTGCA TTGTTGCTGG TTTTCAGGGT GTTAATAAAG AAACCCGCGA TGTCACCACG   660

TTGGGTCGTG GTGGTTCTGA CACCACTGCA GTTGCGTTGG CAGCTGCTTT GAACGCTGAT   720

GTGTGTGAGA TTTACTCGGA CGTTGACGGT GTGTATACCG CTGACCCGCG CATCGTTCCT   780

AATGCACAGA AGCTGGAAAA GCTCAGCTTC GAAGAAATGC TGGAACTTGC TGCTGTTGGC   840

TCCAAGATTT TGGTGCTGCG CAGTGTTGAA TACGCTCGTG CATTCAATGT GCCACTTCGC   900
```

```
GTACGCTCGT CTTATAGTAA TGATCCCGGC ACTTTGATTG CCGGCTCTAT GGAGGATATT         960

CCT GTG GAA GAA GCA GTC CTT ACC GGT GTC GCA ACC GAC AAG TCC GAA        1008
    Met Glu Glu Ala Val Leu Thr Gly Val Ala Thr Asp Lys Ser Glu
    1               5                   10                  15

GCC AAA GTA ACC GTT CTG GGT ATT TCC GAT AAG CCA GGC GAG GCT GCC        1056
Ala Lys Val Thr Val Leu Gly Ile Ser Asp Lys Pro Gly Glu Ala Ala
                20                  25                  30

AAG GTT TTC CGT GCG TTG GCT GAT GCA GAA ATC AAC ATT GAC ATG GTT        1104
Lys Val Phe Arg Ala Leu Ala Asp Ala Glu Ile Asn Ile Asp Met Val
            35                  40                  45

CTG CAG AAC GTC TCC TCT GTG GAA GAC GGC ACC ACC GAC ATC ACG TTC        1152
Leu Gln Asn Val Ser Ser Val Glu Asp Gly Thr Thr Asp Ile Thr Phe
        50                  55                  60

ACC TGC CCT CGC GCT GAC GGA CGT CGT GCG ATG GAG ATC TTG AAG AAG        1200
Thr Cys Pro Arg Ala Asp Gly Arg Arg Ala Met Glu Ile Leu Lys Lys
    65                  70                  75

CTT CAG GTT CAG GGC AAC TGG ACC AAT GTG CTT TAC GAC GAC CAG GTC        1248
Leu Gln Val Gln Gly Asn Trp Thr Asn Val Leu Tyr Asp Asp Gln Val
80                  85                  90                  95

GGC AAA GTC TCC CTC GTG GGT GCT GGC ATG AAG TCT CAC CCA GGT GTT        1296
Gly Lys Val Ser Leu Val Gly Ala Gly Met Lys Ser His Pro Gly Val
                100                 105                 110

ACC GCA GAG TTC ATG GAA GCT CTG CGC GAT GTC AAC GTG AAC ATC GAA        1344
Thr Ala Glu Phe Met Glu Ala Leu Arg Asp Val Asn Val Asn Ile Glu
            115                 120                 125

TTG ATT TCC ACC TCT GAG ATC CGC ATT TCC GTG CTG ATC CGT GAA GAT        1392
Leu Ile Ser Thr Ser Glu Ile Arg Ile Ser Val Leu Ile Arg Glu Asp
        130                 135                 140

GAT CTG GAT GCT GCT GCA CGT GCA TTG CAT GAG CAG TTC CAG CTG GGC        1440
Asp Leu Asp Ala Ala Ala Arg Ala Leu His Glu Gln Phe Gln Leu Gly
    145                 150                 155

GGC GAA GAC GAA GCC GTC GTT TAT GCA GGC ACC GGA CGC TAAAGTTTTAA        1490
Gly Glu Asp Glu Ala Val Val Tyr Ala Gly Thr Gly Arg
160                 165                 170

AGGAGTAGTT TTACAATGAC CACCATCGCA GTTGTTGGTG CAACCGGCCA GGTCGGCCAG        1550

GTTATGCGCA CCCTTTTGGA AGAGCGCAAT TCCCAGCTG ACACTGTTCG TTTCTTTGCT         1610

TCCCCGCGTT CCGCAGGCCG TAAGATTGAA TTC                                     1643

(2) INFORMATION FOR SEQ ID NO:7:

(i) SEQUENCE CHARACTERISTICS:
        (A) LENGTH: 172 amino acids
        (B) TYPE: amino acid
        (D) TOPOLOGY: linear (ii) MOLECULE TYPE: protein (xi) SEQUENCE DESCRIPTION: SEQ ID NO: 7:

Met Glu Glu Ala Val Leu Thr Gly Val Ala Thr Asp Lys Ser Glu Ala
1               5                   10                  15

Lys Val Thr Val Leu Gly Ile Ser Asp Lys Pro Gly Glu Ala Ala Lys
            20                  25                  30

Val Phe Arg Ala Leu Ala Asp Ala Glu Ile Asn Ile Asp Met Val Leu
        35                  40                  45

Gln Asn Val Ser Ser Val Glu Asp Gly Thr Thr Asp Ile Thr Phe Thr
    50                  55                  60

Cys Pro Arg Ala Asp Gly Arg Arg Ala Met Glu Ile Leu Lys Lys Leu
65                  70                  75                  80
```

```
Gln Val Gln Gly Asn Trp Thr Asn Val Leu Tyr Asp Asp Gln Val Gly
                85                  90                  95

Lys Val Ser Leu Val Gly Ala Gly Met Lys Ser His Pro Gly Val Thr
            100                 105                 110

Ala Glu Phe Met Glu Ala Leu Arg Asp Val Asn Val Asn Ile Glu Leu
        115                 120                 125

Ile Ser Thr Ser Glu Ile Arg Ile Ser Val Leu Ile Arg Glu Asp Asp
    130                 135                 140

Leu Asp Ala Ala Ala Arg Ala Leu His Glu Gln Phe Gln Leu Gly Gly
145                 150                 155                 160

Glu Asp Glu Ala Val Val Tyr Ala Gly Thr Gly Arg
                165                 170
```

(2) INFORMATION FOR SEQ ID NO:8:

(i) SEQUENCE CHARACTERISTICS:
        (A) LENGTH: 23 bases
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic DNA"

(iv) ANTI-SENSE: no (xi) SEQUENCE DESCRIPTION: SEQ ID NO: 8:

```
GGATCCCCAA TCGATACCTG GAA                                          23
```

(2) INFORMATION FOR SEQ ID NO:9:

(i) SEQUENCE CHARACTERISTICS:
        (A) LENGTH: 23 bases
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic DNA"

(iv) ANTI-SENSE: yes (xi) SEQUENCE DESCRIPTION: SEQ ID NO: 9:

```
CGGTTCATCG CCAAGTTTTT CTT                                          23
```

(2) INFORMATION FOR SEQ ID NO:10:

(i) SEQUENCE CHARACTERISTICS:
        (A) LENGTH: 2001 bases
        (B) TYPE: nucleic acid
        (C) STRANDEDNESS: double
        (D) TOPOLOGY: linear (ii) MOLECULE TYPE: genomic DNA (vi) ORIGINAL SOURCE:
        (A) ORGANISM: Brevibacterium lactofermentum
        (B) STRAIN: ATCC 13869

(ix) FEATURE:
        (A) NAME/KEY: CDS
        (B) LOCATION: 730..1473

(xi) SEQUENCE DESCRIPTION: SEQ ID NO: 10:

```
GGATCCCCAA TCGATACCTG GAACGACAAC CTGATCAGGA TATCCAATGC CTTGAATATT     60

GACGTTGAGG AAGGAATCAC CAGCCATCTC AACTGGAAGA CCTGACGCCT GCTGAATTGG    120

ATCAGTGGCC CAATCGACCC ACCAACCAGG TTGGCTATTA CCGGCGATAT CAAAAACAAC    180
```

```
TCGCGTGAAC GTTTCGTGCT CGGCAACGCG GATGCCAGCG ATCGACATAT CGGAGTCACC        240

AACTTGAGCC TGCTGCTTCT GATCCATCGA CGGGGAACCC AACGGCGGCA AAGCAGTGGG        300

GGAAGGGGAG TTGGTGGACT CTGAATCAGT GGGCTCTGAA GTGGTAGGCG ACGGGGCAGC        360

ATCTGAAGGC GTGCGAGTTG TGGTGACCGG GTTAGCGGTT TCAGTTTCTG TCACAACTGG        420

AGCAGGACTA GCAGAGGTTG TAGGCGTTGA GCCGCTTCCA TCACAAGCAC TTAAAAGTAA        480

AGAGGCGGAA ACCACAAGCG CCAAGGAACT ACCTGCGGAA CGGGCGGTGA AGGGCAACTT        540

AAGTCTCATA TTTCAAACAT AGTTCCACCT GTGTGATTAA TCTCCAGAAC GGAACAAACT        600

GATGAACAAT CGTTAACAAC ACAGACCAAA ACGGTCAGTT AGGTATGGAT ATCAGCACCT        660

TCTGAATGGG TACGTCTAGA CTGGTGGGCG TTTGAAAAAC TCTTCGCCCC ACGAAAATGA        720

AGGAGCATA ATG GGA ATC AAG GTT GGC GTT CTC GGA GCC AAA GGC CGT           768
          Met Gly Ile Lys Val Gly Val Leu Gly Ala Lys Gly Arg
            1               5                  10

GTT GGT CAA ACT ATT GTG GCA GCA GTC AAT GAG TCC GAC GAT CTG GAG         816
Val Gly Gln Thr Ile Val Ala Ala Val Asn Glu Ser Asp Asp Leu Glu
    15                  20                  25

CTT GTT GCA GAG ATC GGC GTC GAC GAT GAT TTG AGC CTT CTG GTA GAC         864
Leu Val Ala Glu Ile Gly Val Asp Asp Asp Leu Ser Leu Leu Val Asp
30                  35                  40                  45

AAC GGC GCT GAA GTT GTC GTT GAC TTC ACC ACT CCT AAC GCT GTG ATG         912
Asn Gly Ala Glu Val Val Val Asp Phe Thr Thr Pro Asn Ala Val Met
                50                  55                  60

GGC AAC CTG GAG TTC TGC ATC AAC AAC GGC ATT TCT GCG GTT GTT GGA         960
Gly Asn Leu Glu Phe Cys Ile Asn Asn Gly Ile Ser Ala Val Val Gly
            65                  70                  75

ACC ACG GGC TTC GAT GAT GCT CGT TTG GAG CAG GTT CGC GCC TGG CTT        1008
Thr Thr Gly Phe Asp Asp Ala Arg Leu Glu Gln Val Arg Ala Trp Leu
        80                  85                  90

GAA GGA AAA GAC AAT GTC GGT GTT CTG ATC GCA CCT AAC TTT GCT ATC        1056
Glu Gly Lys Asp Asn Val Gly Val Leu Ile Ala Pro Asn Phe Ala Ile
    95                  100                 105

TCT GCG GTG TTG ACC ATG GTC TTT TCC AAG CAG GCT GCC CGC TTC TTC        1104
Ser Ala Val Leu Thr Met Val Phe Ser Lys Gln Ala Ala Arg Phe Phe
110                 115                 120                 125

GAA TCA GCT GAA GTT ATT GAG CTG CAC CAC CCC AAC AAG CTG GAT GCA        1152
Glu Ser Ala Glu Val Ile Glu Leu His His Pro Asn Lys Leu Asp Ala
                130                 135                 140

CCT TCA GGC ACC GCG ATC CAC ACT GCT CAG GGC ATT GCT GCG GCA CGC        1200
Pro Ser Gly Thr Ala Ile His Thr Ala Gln Gly Ile Ala Ala Ala Arg
            145                 150                 155

AAA GAA GCA GGC ATG GAC GCA CAG CCA GAT GCG ACC GAG CAG GCA CTT        1248
Lys Glu Ala Gly Met Asp Ala Gln Pro Asp Ala Thr Glu Gln Ala Leu
        160                 165                 170

GAG GGT TCC CGT GGC GCA AGC GTA GAT GGA ATC CCA GTT CAC GCA GTC        1296
Glu Gly Ser Arg Gly Ala Ser Val Asp Gly Ile Pro Val His Ala Val
    175                 180                 185

CGC ATG TCC GGC ATG GTT GCT CAC GAG CAA GTT ATC TTT GGC ACC CAG        1344
Arg Met Ser Gly Met Val Ala His Glu Gln Val Ile Phe Gly Thr Gln
190                 195                 200                 205

GGT CAG ACC TTG ACC ATC AAG CAG GAC TCC TAT GAT CGC AAC TCA TTT        1392
Gly Gln Thr Leu Thr Ile Lys Gln Asp Ser Tyr Asp Arg Asn Ser Phe
                210                 215                 220

GCA CCA GGT GTC TTG GTG GGT GTG CGC AAC ATT GCA CAG CAC CCA GGC        1440
Ala Pro Gly Val Leu Val Gly Val Arg Asn Ile Ala Gln His Pro Gly
            225                 230                 235
```

```
CTA GTC GTA GGA CTT GAG CAT TAC CTA GGC CTG TAAAGGCTCA TTTCAGCAGC    1493
Leu Val Val Gly Leu Glu His Tyr Leu Gly Leu
            240                 245

GGGTGGAATT TTTTAAAAGG AGCGTTTAAA GGCTGTGGCC AACAAGTTA AATTGAGCGT     1553

GGAGTTGATA GCGTGCAGTT CTTTTACTCC ACCCGCTGAT GTTGAGTGGT CAACTGATGT    1613

TGAGGGCGCG AAGCACTCG TCGAGTTTGC GGGTCGTGCC TGCTACGAAA CTTTTGATAA     1673

GCCGAACCCT CGAACTGCTT CCAATGCTGC GTATCTGCGC ACATCATGG AAGTGGGGCA     1733

CACTGCTTTG CTTGAGCATG CCAATGCCAC GATGTATATC CGAGGCATTT CTCGGTCCGC    1793

GACCCATGAA TTGGTCCGAC ACCGCCATTT TTCCTTCTCT CAACTGTCTC AGCGTTTCGT    1853

GCACAGCGGA GAATCGGAAG TAGTGGTGCC CACTCTCATC GATGAAGATC CGCAGTTGCG    1913

TGAACTTTTC ATGCACGCCA TGGATGAGTC TCGGTTCGCT TTCAATGAGC TGCTTAATGC    1973

GCTGGAAGAA AAACTTGGCG ATGAACCG                                      2001

(2) INFORMATION FOR SEQ ID NO:11:

(i) SEQUENCE CHARACTERISTICS:
           (A) LENGTH: 248 amino acids
           (B) TYPE: amino acid
           (D) TOPOLOGY: linear (ii) MOLECULE TYPE: protein (xi) SEQUENCE DESCRIPTION: SEQ ID NO: 11:

Met Gly Ile Lys Val Gly Val Leu Gly Ala Lys Gly Arg Val Gly Gln
 1               5                  10                  15

Thr Ile Val Ala Ala Val Asn Glu Ser Asp Asp Leu Glu Leu Val Ala
            20                  25                  30

Glu Ile Gly Val Asp Asp Leu Ser Leu Leu Val Asp Asn Gly Ala
        35                  40                  45

Glu Val Val Asp Phe Thr Thr Pro Asn Ala Val Met Gly Asn Leu
    50                  55                  60

Glu Phe Cys Ile Asn Asn Gly Ile Ser Ala Val Val Gly Thr Thr Gly
 65                  70                  75                  80

Phe Asp Asp Ala Arg Leu Glu Gln Val Arg Ala Trp Leu Glu Gly Lys
                85                  90                  95

Asp Asn Val Gly Val Leu Ile Ala Pro Asn Phe Ala Ile Ser Ala Val
            100                 105                 110

Leu Thr Met Val Phe Ser Lys Gln Ala Ala Arg Phe Phe Glu Ser Ala
        115                 120                 125

Glu Val Ile Glu Leu His His Pro Asn Lys Leu Asp Ala Pro Ser Gly
    130                 135                 140

Thr Ala Ile His Thr Ala Gln Gly Ile Ala Ala Arg Lys Glu Ala
145                 150                 155                 160

Gly Met Asp Ala Gln Pro Asp Ala Thr Glu Gln Ala Leu Glu Gly Ser
                165                 170                 175

Arg Gly Ala Ser Val Asp Gly Ile Pro Val His Ala Val Arg Met Ser
            180                 185                 190

Gly Met Val Ala His Glu Gln Val Ile Phe Gly Thr Gln Gly Gln Thr
        195                 200                 205

Leu Thr Ile Lys Gln Asp Ser Tyr Asp Arg Asn Ser Phe Ala Pro Gly
    210                 215                 220

Val Leu Val Gly Val Arg Asn Ile Ala Gln His Pro Gly Leu Val Val
225                 230                 235                 240
```

-continued

```
Gly Leu Glu His Tyr Leu Gly Leu
            245

(2) INFORMATION FOR SEQ ID NO:12:

(i) SEQUENCE CHARACTERISTICS:
        (A) LENGTH: 23 bases
        (B) TYPE: nucleic acid
        (C) STRANDEDNESS: single
        (D) TOPOLOGY: linear (ii) MOLECULE TYPE: other nucleic acid
         (A) DESCRIPTION:   /desc = "synthetic DNA"

(iv) ANTI-SENSE: no (xi) SEQUENCE DESCRIPTION: SEQ ID NO: 12:

GTCGACGGAT CGCAAATGGC AAC                                              23

(2) INFORMATION FOR SEQ ID NO:13:

(i) SEQUENCE CHARACTERISTICS:
        (A) LENGTH: 23 bases
        (B) TYPE: nucleic acid
        (C) STRANDEDNESS: single
        (D) TOPOLOGY: linear (ii) MOLECULE TYPE: other nucleic acid
         (A) DESCRIPTION:   /desc = "synthetic DNA"

(iv) ANTI-SENSE: yes (xi) SEQUENCE DESCRIPTION: SEQ ID NO: 13:

GGATCCTTGA GCACCTTGCG CAG                                              23

(2) INFORMATION FOR SEQ ID NO:14:

(i) SEQUENCE CHARACTERISTICS:
        (A) LENGTH: 1411 bases
        (B) TYPE: nucleic acid
        (C) STRANDEDNESS: double
        (D) TOPOLOGY: linear (ii) MOLECULE TYPE: genomic DNA (vi) ORIGINAL SOURCE:
         (A) ORGANISM: Brevibacterium lactofermentum
         (B) STRAIN: ATCC 13869

(ix) FEATURE:
         (A) NAME/KEY: CDS
         (B) LOCATION: 311..1213

(xi) SEQUENCE DESCRIPTION: SEQ ID NO: 14:

CTCTCGATAT CGAGAGAGAA GCAGCGCCAC GGTTTTTCGG TGATTTTGAG ATTGAAACTT        60

TGGCAGACGG ATCGCAAATG CAACAAGCC CGTATGTCAT GGACTTTTAA CGCAAAGCTC       120

ACACCCACGA GCTAAAAATT CATATAGTTA AGACAACATT TTTGGCTGTA AAAGACAGCC      180

GTAAAAACCT CTTGCTCATG TCAATTGTTC TTATCGGAAT GTGGCTTGGG CGATTGTTAT      240

GCAAAAGTTG TTAGGTTTTT TGCGGGGTTG TTTAACCCCC AAATGAGGGA AGAAGGTAAC      300

CTTGAACTCT ATG AGC ACA GGT TTA ACA GCT AAG ACC GGA GTA GAG CAC         349
            Met Ser Thr Gly Leu Thr Ala Lys Thr Gly Val Glu His
              1               5                  10

TTC GGC ACC GTT GGA GTA GCA ATG GTT ACT CCA TTC ACG GAA TCC GGA        397
Phe Gly Thr Val Gly Val Ala Met Val Thr Pro Phe Thr Glu Ser Gly
 15                  20                  25
```

```
GAC ATC GAT ATC GCT GCT GGC CGC GAA GTC GCG GCT TAT TTG GTT GAT        445
Asp Ile Asp Ile Ala Ala Gly Arg Glu Val Ala Ala Tyr Leu Val Asp
 30              35                  40                  45

AAG GGC TTG GAT TCT TTG GTT CTC GCG GGC ACC ACT GGT GAA TCC CCA        493
Lys Gly Leu Asp Ser Leu Val Leu Ala Gly Thr Thr Gly Glu Ser Pro
                 50                  55                  60

ACG ACA ACC GCC GCT GAA AAA CTA GAA CTG CTC AAG GCC GTT CGT GAG        541
Thr Thr Thr Ala Ala Glu Lys Leu Glu Leu Leu Lys Ala Val Arg Glu
             65                  70                  75

GAA GTT GGG GAT CGG GCG AAC GTC ATC GCC GGT GTC GGA ACC AAC AAC        589
Glu Val Gly Asp Arg Ala Asn Val Ile Ala Gly Val Gly Thr Asn Asn
         80                  85                  90

ACG CGG ACA TCT GTG GAA CTT GCG GAA GCT GCT GCT TCT GCT GGC GCA        637
Thr Arg Thr Ser Val Glu Leu Ala Glu Ala Ala Ala Ser Ala Gly Ala
     95                 100                 105

GAC GGC CTT TTA GTT GTA ACT CCT TAT TAC TCC AAG CCG AGC CAA GAG        685
Asp Gly Leu Leu Val Val Thr Pro Tyr Tyr Ser Lys Pro Ser Gln Glu
110                 115                 120                 125

GGA TTG CTG GCG CAC TTC GGT GCA ATT GCT GCA GCA ACA GAG GTT CCA        733
Gly Leu Leu Ala His Phe Gly Ala Ile Ala Ala Ala Thr Glu Val Pro
                130                 135                 140

ATT TGT CTC TAT GAC ATT CCT GGT CGG TCA GGT ATT CCA ATT GAG TCT        781
Ile Cys Leu Tyr Asp Ile Pro Gly Arg Ser Gly Ile Pro Ile Glu Ser
            145                 150                 155

GAT ACC ATG AGA CGC CTG AGT GAA TTA CCT ACG ATT TTG GCG GTC AAG        829
Asp Thr Met Arg Arg Leu Ser Glu Leu Pro Thr Ile Leu Ala Val Lys
        160                 165                 170

GAC GCC AAG GGT GAC CTC GTT GCA GCC ACG TCA TTG ATC AAA GAA ACG        877
Asp Ala Lys Gly Asp Leu Val Ala Ala Thr Ser Leu Ile Lys Glu Thr
    175                 180                 185

GGA CTT GCC TGG TAT TCA GGC GAT GAC CCA CTA AAC CTT GTT TGG CTT        925
Gly Leu Ala Trp Tyr Ser Gly Asp Asp Pro Leu Asn Leu Val Trp Leu
190                 195                 200                 205

GCT TTG GGC GGA TCA GGT TTC ATT TCC GTA ATT GGA CAT GCA GCC CCC        973
Ala Leu Gly Gly Ser Gly Phe Ile Ser Val Ile Gly His Ala Ala Pro
                210                 215                 220

ACA GCA TTA CGT GAG TTG TAC ACA AGC TTC GAG GAA GGC GAC CTC GTC       1021
Thr Ala Leu Arg Glu Leu Tyr Thr Ser Phe Glu Glu Gly Asp Leu Val
            225                 230                 235

CGT GCG CGG GAA ATC AAC GCC AAA CTA TCA CCG CTG GTA GCT GCC CAA       1069
Arg Ala Arg Glu Ile Asn Ala Lys Leu Ser Pro Leu Val Ala Ala Gln
        240                 245                 250

GGT CGC TTG GGT GGA GTC AGC TTG GCA AAA GCT GCT CTG CGT CTG CAG       1117
Gly Arg Leu Gly Gly Val Ser Leu Ala Lys Ala Ala Leu Arg Leu Gln
    255                 260                 265

GGC ATC AAC GTA GGA GAT CCT CGA CTT CCA ATT ATG GCT CCA AAT GAG       1165
Gly Ile Asn Val Gly Asp Pro Arg Leu Pro Ile Met Ala Pro Asn Glu
270                 275                 280                 285

CAG GAA CTT GAG GCT CTC CGA GAA GAC ATG AAA AAA GCT GGA GTT CTA       1213
Gln Glu Leu Glu Ala Leu Arg Glu Asp Met Lys Lys Ala Gly Val Leu
                290                 295                 300

TAAATATGAA TGATTCCCGA AATCGCGGCC GGAAGGTTAC CCGCAAGGCG GCCCACCAGA     1273

AGCTGGTCAG GAAACCATC TGGATACCCC TGTCTTTCAG GCACCAGATG CTTCCTCTAA      1333

CCAGAGCGCT GTAAAAGCTG AGACCGCCGG AAACGACAAT CGGGATGCTG CGCAAGGTGC     1393

TCAAGGATCC CAACATTC                                                   1411

(2) INFORMATION FOR SEQ ID NO:15:

(i) SEQUENCE CHARACTERISTICS:
```

(A) LENGTH: 301 amino acids
(B) TYPE: amino acid
(D) TOPOLOGY: linear (ii) MOLECULE TYPE: protein (xi) SEQUENCE DESCRIPTION: SEQ ID NO: 15:

```
Met Ser Thr Gly Leu Thr Ala Lys Thr Gly Val Glu His Phe Gly Thr
 1               5                  10                  15

Val Gly Val Ala Met Val Thr Pro Phe Thr Glu Ser Gly Asp Ile Asp
            20                  25                  30

Ile Ala Ala Gly Arg Glu Val Ala Ala Tyr Leu Val Asp Lys Gly Leu
            35                  40                  45

Asp Ser Leu Val Leu Ala Gly Thr Thr Gly Glu Ser Pro Thr Thr Thr
     50                  55                  60

Ala Ala Glu Lys Leu Glu Leu Leu Lys Ala Val Arg Glu Glu Val Gly
 65                  70                  75                  80

Asp Arg Ala Asn Val Ile Ala Gly Val Gly Thr Asn Asn Thr Arg Thr
                85                  90                  95

Ser Val Glu Leu Ala Glu Ala Ala Ser Ala Gly Ala Asp Gly Leu
            100                 105                 110

Leu Val Val Thr Pro Tyr Tyr Ser Lys Pro Ser Gln Glu Gly Leu Leu
            115                 120                 125

Ala His Phe Gly Ala Ile Ala Ala Thr Glu Val Pro Ile Cys Leu
    130                 135                 140

Tyr Asp Ile Pro Gly Arg Ser Gly Ile Pro Ile Glu Ser Asp Thr Met
145                 150                 155                 160

Arg Arg Leu Ser Glu Leu Pro Thr Ile Leu Ala Val Lys Asp Ala Lys
                165                 170                 175

Gly Asp Leu Val Ala Ala Thr Ser Leu Ile Lys Glu Thr Gly Leu Ala
            180                 185                 190

Trp Tyr Ser Gly Asp Asp Pro Leu Asn Leu Val Trp Leu Ala Leu Gly
        195                 200                 205

Gly Ser Gly Phe Ile Ser Val Ile Gly His Ala Ala Pro Thr Ala Leu
    210                 215                 220

Arg Glu Leu Tyr Thr Ser Phe Glu Glu Gly Asp Leu Val Arg Ala Arg
225                 230                 235                 240

Glu Ile Asn Ala Lys Leu Ser Pro Leu Val Ala Ala Gln Gly Arg Leu
                245                 250                 255

Gly Gly Val Ser Leu Ala Lys Ala Ala Leu Arg Leu Gln Leu Gly Ile Asn
            260                 265                 270

Val Gly Asp Pro Arg Leu Pro Ile Met Ala Pro Asn Glu Gln Glu Leu
            275                 280                 285

Glu Ala Leu Arg Glu Asp Met Lys Lys Ala Gly Val Leu
    290                 295                 300
```

(2) INFORMATION FOR SEQ ID NO:16:

(i) SEQUENCE CHARACTERISTICS:
    (A) LENGTH: 23 bases
    (B) TYPE: nucleic acid
    (C) STRANDEDNESS: single
    (D) TOPOLOGY: linear (ii) MOLECULE TYPE: other nucleic acid
    (A) DESCRIPTION: /desc = "synthetic DNA"

(iv) ANTI-SENSE: no (xi) SEQUENCE DESCRIPTION: SEQ ID NO: 16:

GTGGAGCCGA CCATTCCGCG AGG                                                23

(2) INFORMATION FOR SEQ ID NO:17:

(i) SEQUENCE CHARACTERISTICS:
        (A) LENGTH: 23 bases
        (B) TYPE: nucleic acid
        (C) STRANDEDNESS: single
        (D) TOPOLOGY: linear (ii) MOLECULE TYPE: other nucleic acid
        (A) DESCRIPTION:   /desc = "synthetic DNA"

(iv) ANTI-SENSE: yes (xi) SEQUENCE DESCRIPTION: SEQ ID NO: 17:

CCAAAACCGC CCTCCACGGC GAA                                                23

(2) INFORMATION FOR SEQ ID NO:18:

(i) SEQUENCE CHARACTERISTICS:
        (A) LENGTH: 3579 bases
        (B) TYPE: nucleic acid
        (C) STRANDEDNESS: double
        (D) TOPOLOGY: linear (ii) MOLECULE TYPE: genomic DNA (vi) ORIGINAL SOURCE:
        (A) ORGANISM: Brevibacterium lactofermentum
        (B) STRAIN: ATCC 13869

(ix) FEATURE:
        (A) NAME/KEY: CDS
        (B) LOCATION: 533..2182

(ix) FEATURE:
        (A) NAME/KEY: CDS
        (B) LOCATION: 2188..3522

(xi) SEQUENCE DESCRIPTION: SEQ ID NO: 18:

```
GTGGAGCCGA CCATTCCGCG AGGCTGCACT GCAACGAGGT CGTAGTTTTG GTACATGGCT         60

TCTGGCCAGT TCATGGATTG GCTGCCGAAG AAGCTATAGG CATCGCACCA GGGCCACCGA        120

GTTACCGAAG ATGGTGCCGT GCTTTTCGCC TTGGGCAGGG ACCTTGACAA AGCCCACGCT        180

GATATCGCCA AGTGAGGGAT CAGAATAGTG CATGGGCACG TCGATGCTGC CACATTGAGC        240

GGAGGCAATA TCTACCTGAG GTGGGCATTC TTCCCAGCGG ATGTTTTCTT GCGCTGCTGC        300

AGTGGGCATT GATACCAAAA AGGGGCTAAG CGCAGTCGAG GCGGCAAGAA CTGCTACTAC        360

CCTTTTTATT GTCGAACGGG GCATTACGGC TCCAAGGACG TTTGTTTTCT GGGTCAGTTA        420

CCCCAAAAAG CATATACAGA GACCAATGAT TTTTCATTAA AAAGGCAGGG ATTTGTTATA        480

AGTATGGGTC GTATTCTGTG CGACGGGTGT ACCTCGGCTA GAATTTCTCC CC ATG            535
                                                          Met
                                                           1

ACA CCA GCT GAT CTC GCA ACA TTG ATT AAA GAG ACC GCG GTA GAG GTT          583
Thr Pro Ala Asp Leu Ala Thr Leu Ile Lys Glu Thr Ala Val Glu Val
            5                  10                  15

TTG ACC TCC CGC GAG CTC GAT ACT TCT GTT CTT CCG GAG CAG GTA GTT          631
Leu Thr Ser Arg Glu Leu Asp Thr Ser Val Leu Pro Glu Gln Val Val
        20                  25                  30

GTG GAG CGT CCG CGT AAC CCA GAG CAC GGC GAT TAC GCC ACC AAC ATT          679
Val Glu Arg Pro Arg Asn Pro Glu His Gly Asp Tyr Ala Thr Asn Ile
    35                  40                  45
```

```
GCA TTG CAG GTG GCT AAA AAG GTC GGT CAG AAC CCT CGG GAT TTG GCT    727
Ala Leu Gln Val Ala Lys Lys Val Gly Gln Asn Pro Arg Asp Leu Ala
 50              55                  60                  65

ACC TGG CTG GCA GAG GCA TTG GCT GCA GAT GAC GCC ATT GAT TCT GCT    775
Thr Trp Leu Ala Glu Ala Leu Ala Ala Asp Asp Ala Ile Asp Ser Ala
             70                  75                  80

GAA ATT GCT GGC CCA GGC TTT TTG AAC ATT CGC CTT GCT GCA GCA GCA    823
Glu Ile Ala Gly Pro Gly Phe Leu Asn Ile Arg Leu Ala Ala Ala Ala
                 85                  90                  95

CAG GGT GAA ATT GTG GCC AAG ATT CTG GCA CAG GGC GAG ACT TTC GGA    871
Gln Gly Glu Ile Val Ala Lys Ile Leu Ala Gln Gly Glu Thr Phe Gly
            100                 105                 110

AAC TCC GAT CAC CTT TCC CAC TTG GAC GTG AAC CTC GAG TTC GTT TCT    919
Asn Ser Asp His Leu Ser His Leu Asp Val Asn Leu Glu Phe Val Ser
        115                 120                 125

GCA AAC CCA ACC GGA CCT ATT CAC CTT GGC GGA ACC CGC TGG GCT GCC    967
Ala Asn Pro Thr Gly Pro Ile His Leu Gly Gly Thr Arg Trp Ala Ala
130                 135                 140                 145

GTG GGT GAC TCT TTG GGT CGT GTG CTG GAG GCT TCC GGC GCG AAA GTG   1015
Val Gly Asp Ser Leu Gly Arg Val Leu Glu Ala Ser Gly Ala Lys Val
                150                 155                 160

ACC CGC GAA TAC TAC TTC AAC GAT CAC GGT CGC CAG ATC GAT CGT TTC   1063
Thr Arg Glu Tyr Tyr Phe Asn Asp His Gly Arg Gln Ile Asp Arg Phe
            165                 170                 175

GCT TTG TCC CTT CTT GCA GCG GCG AAG GGC GAG CCA ACG CCA GAA GAC   1111
Ala Leu Ser Leu Leu Ala Ala Ala Lys Gly Glu Pro Thr Pro Glu Asp
        180                 185                 190

GGT TAT GGC GGC GAA TAC ATT AAG GAA ATT GCG GAG GCA ATC GTC GAA   1159
Gly Tyr Gly Gly Glu Tyr Ile Lys Glu Ile Ala Glu Ala Ile Val Glu
    195                 200                 205

AAG CAT CCT GAA GCG TTG GCT TTG GAG CCT GCC GCA ACC CAG GAG CTT   1207
Lys His Pro Glu Ala Leu Ala Leu Glu Pro Ala Ala Thr Gln Glu Leu
210                 215                 220                 225

TTC CGC GCT GAA GGC GTG GAG ATG ATG TTC GAG CAC ATC AAA TCT TCC   1255
Phe Arg Ala Glu Gly Val Glu Met Met Phe Glu His Ile Lys Ser Ser
                230                 235                 240

CTG CAT GAG TTC GGC ACC GAT TTC GAT GTC TAC TAC CAC GAG AAC TCC   1303
Leu His Glu Phe Gly Thr Asp Phe Asp Val Tyr Tyr His Glu Asn Ser
            245                 250                 255

CTG TTC GAG TCC GGT GCG GTG GAC AAG GCC GTG CAG GTG CTG AAG GAC   1351
Leu Phe Glu Ser Gly Ala Val Asp Lys Ala Val Gln Val Leu Lys Asp
        260                 265                 270

AAC GGC AAC CTG TAC GAA AAC GAG GGC GCT TGG TGG CTG CGT TCC ACC   1399
Asn Gly Asn Leu Tyr Glu Asn Glu Gly Ala Trp Trp Leu Arg Ser Thr
    275                 280                 285

GAA TTC GGC GAT GAC AAA GAC CGC GTG GTG ATC AAG TCT GAC GGC GAC   1447
Glu Phe Gly Asp Asp Lys Asp Arg Val Val Ile Lys Ser Asp Gly Asp
290                 295                 300                 305

GCA GCC TAC ATC GCT GGC GAT ATC GCG TAC GTG GCT GAT AAG TTC TCC   1495
Ala Ala Tyr Ile Ala Gly Asp Ile Ala Tyr Val Ala Asp Lys Phe Ser
                310                 315                 320

CGC GGA CAC AAC CTA AAC ATC TAC ATG TTG GGT GCT GAC CAC CAT GGT   1543
Arg Gly His Asn Leu Asn Ile Tyr Met Leu Gly Ala Asp His His Gly
            325                 330                 335

TAC ATC GCG CGC CTG AAG GCA GCG GCG GCG GCA CTT GGC TAC AAG CCA   1591
Tyr Ile Ala Arg Leu Lys Ala Ala Ala Ala Leu Gly Tyr Lys Pro
        340                 345                 350

GAA GGC GTT GAA GTC CTG ATT GGC CAG ATG GTG AAC CTG CTT CGC GAC   1639
Glu Gly Val Glu Val Leu Ile Gly Gln Met Val Asn Leu Leu Arg Asp
    355                 360                 365
```

```
GGC AAG GCA GTG CGT ATG TCC AAG CGT GCA GGC ACC GTG GTC ACC CTA                1687
Gly Lys Ala Val Arg Met Ser Lys Arg Ala Gly Thr Val Val Thr Leu
370             375                 380                 385

GAT GAC CTC GTT GAA GCA ATC GGC ATC GAT GCG GCG CGT TAC TCC CTG                1735
Asp Asp Leu Val Glu Ala Ile Gly Ile Asp Ala Ala Arg Tyr Ser Leu
                390                 395                 400

ATC CGT TCC TCC GTG GAT TCT TCC CTG GAT ATC GAT CTC GGC CTG TGG                1783
Ile Arg Ser Ser Val Asp Ser Ser Leu Asp Ile Asp Leu Gly Leu Trp
            405                 410                 415

GAA TCC CAG TCC TCC GAC AAC CCT GTG TAC TAC GTG CAG TAC GGA CAC                1831
Glu Ser Gln Ser Ser Asp Asn Pro Val Tyr Tyr Val Gln Tyr Gly His
        420                 425                 430

GCT CGT CTG TGC TCC ATC GCG CGC AAG GCA GAG ACC TTG GGT GTC ACC                1879
Ala Arg Leu Cys Ser Ile Ala Arg Lys Ala Glu Thr Leu Gly Val Thr
    435                 440                 445

GAG GAA GGC GCA GAC CTA TCT CTA CTG ACC CAC GAC CGC GAA GGC GAT                1927
Glu Glu Gly Ala Asp Leu Ser Leu Leu Thr His Asp Arg Glu Gly Asp
450                 455                 460                 465

CTC ATC CGC ACA CTC GGA GAG TTC CCA GCA GTG GTG AAG GCT GCC GCT                1975
Leu Ile Arg Thr Leu Gly Glu Phe Pro Ala Val Val Lys Ala Ala Ala
                470                 475                 480

GAC CTA CGT GAA CCA CAC CGC ATT GCC CGC TAT GCT GAG GAA TTA GCT                2023
Asp Leu Arg Glu Pro His Arg Ile Ala Arg Tyr Ala Glu Glu Leu Ala
            485                 490                 495

GGA ACT TTC CAC CGC TTC TAC GAT TCC TGC CAC ATC CTT CCA AAG GTT                2071
Gly Thr Phe His Arg Phe Tyr Asp Ser Cys His Ile Leu Pro Lys Val
        500                 505                 510

GAT GAG GAT ACG GCA CCA ATC CAC ACA GCA CGT CTG GCA CTT GCA GCA                2119
Asp Glu Asp Thr Ala Pro Ile His Thr Ala Arg Leu Ala Leu Ala Ala
    515                 520                 525

GCA ACC CGC CAG ACC CTC GCT AAC GCC CTG CAC CTG GTT GGC GTT TCC                2167
Ala Thr Arg Gln Thr Leu Ala Asn Ala Leu His Leu Val Gly Val Ser
530                 535                 540                 545

GCA CCG GAG AAG ATG TAACA ATG GCT ACA GTT GAA AAT TTC AAT GAA                  2214
Ala Pro Glu Lys Met       Met Ala Thr Val Glu Asn Phe Asn Glu
                550         1           5

CTT CCC GCA CAC GTA TGG CCA CGC AAT GCC GTG CGC CAA GAA GAC GGC                2262
Leu Pro Ala His Val Trp Pro Arg Asn Ala Val Arg Gln Glu Asp Gly
 10              15                  20                  25

GTT GTC ACC GTC GCT GGT GTG CCT CTG CCT GAC CTC GCT GAA GAA TAC                2310
Val Val Thr Val Ala Gly Val Pro Leu Pro Asp Leu Ala Glu Glu Tyr
             30                  35                  40

GGA ACC CCA CTG TTC GTA GTC GAC GAG GAC GAT TTC CGT TCC CGC TGT                2358
Gly Thr Pro Leu Phe Val Val Asp Glu Asp Asp Phe Arg Ser Arg Cys
         45                  50                  55

CGC GAC ATG GCT ACC GCA TTC GGT GGA CCA GGC AAT GTG CAC TAC GCA                2406
Arg Asp Met Ala Thr Ala Phe Gly Gly Pro Gly Asn Val His Tyr Ala
     60                  65                  70

TCT AAA GCG TTC CTG ACC AAG ACC ATT GCA CGT TGG GTT GAT GAA GAG                2454
Ser Lys Ala Phe Leu Thr Lys Thr Ile Ala Arg Trp Val Asp Glu Glu
 75                  80                  85

GGG CTG GCA CTG GAC ATT GCA TCC ATC AAC GAA CTG GGC ATT GCC CTG                2502
Gly Leu Ala Leu Asp Ile Ala Ser Ile Asn Glu Leu Gly Ile Ala Leu
 90                  95                 100                 105

GCC GCT GGT TTC CCC GCC AGC CGT ATC ACC GCG CAC GGC AAC AAC AAA                2550
Ala Ala Gly Phe Pro Ala Ser Arg Ile Thr Ala His Gly Asn Asn Lys
                 110                 115                 120

GGC GTA GAG TTC CTG CGC GCG TTG GTT CAA AAC GGT GTG GGA CAC GTG                2598
Gly Val Glu Phe Leu Arg Ala Leu Val Gln Asn Gly Val Gly His Val
             125                 130                 135
```

```
GTG CTG GAC TCC GCA CAG GAA CTA GAA CTG TTG GAT TAC GTT GCC GCT       2646
Val Leu Asp Ser Ala Gln Glu Leu Glu Leu Leu Asp Tyr Val Ala Ala
            140                 145                 150

GGT GAA GGC AAG ATT CAG GAC GTG TTG ATC CGC GTA AAG CCA GGC ATC       2694
Gly Glu Gly Lys Ile Gln Asp Val Leu Ile Arg Val Lys Pro Gly Ile
155                 160                 165

GAA GCA CAC ACC CAC GAG TTC ATC GCC ACT AGC CAC GAA GAC CAG AAG       2742
Glu Ala His Thr His Glu Phe Ile Ala Thr Ser His Glu Asp Gln Lys
170                 175                 180                 185

TTC GGA TTC TCC CTG GCA TCC GGT TCC GCA TTC GAA GCA GCA AAA GCC       2790
Phe Gly Phe Ser Leu Ala Ser Gly Ser Ala Phe Glu Ala Ala Lys Ala
            190                 195                 200

GCC AAC AAC GCA GAA AAC CTG AAC CTG GTT GGC CTG CAC TGC CAC GTT       2838
Ala Asn Asn Ala Glu Asn Leu Asn Leu Val Gly Leu His Cys His Val
            205                 210                 215

GGT TCC CAG GTG TTC GAC GCC GAA GGC TTC AAG CTG GCA GCA GAA CGC       2886
Gly Ser Gln Val Phe Asp Ala Glu Gly Phe Lys Leu Ala Ala Glu Arg
220                 225                 230

GTG TTG GGC CTG TAC TCA CAG ATC CAC AGC GAA CTG GGC GTT GCC CTT       2934
Val Leu Gly Leu Tyr Ser Gln Ile His Ser Glu Leu Gly Val Ala Leu
            235                 240                 245

CCT GAA CTG GAT CTC GGT GGC GGA TAC GGC ATT GCC TAT ACC GCA GCT       2982
Pro Glu Leu Asp Leu Gly Gly Gly Tyr Gly Ile Ala Tyr Thr Ala Ala
250                 255                 260                 265

GAA GAA CCA CTC AAC GTC GCA GAA GTT GCC TCC GAC CTG CTC ACC GCA       3030
Glu Glu Pro Leu Asn Val Ala Glu Val Ala Ser Asp Leu Leu Thr Ala
            270                 275                 280

GTC GGA AAA ATG GCA GCG GAA CTA GGC ATC GAC GCA CCA ACC GTG CTT       3078
Val Gly Lys Met Ala Ala Glu Leu Gly Ile Asp Ala Pro Thr Val Leu
            285                 290                 295

GTT GAG CCC GGC CGC GCT ATC GCA GGC CCC TCC ACC GTG ACC ATC TAC       3126
Val Glu Pro Gly Arg Ala Ile Ala Gly Pro Ser Thr Val Thr Ile Tyr
            300                 305                 310

GAA GTC GGC ACC ACC AAA GAC GTC CAC GTA GAC GAC GAC AAA ACC CGC       3174
Glu Val Gly Thr Thr Lys Asp Val His Val Asp Asp Asp Lys Thr Arg
315                 320                 325

CGT TAC ATC GCC GTG GAC GGA GGC ATG TCC GAC AAC ATC CGC CCA GCA       3222
Arg Tyr Ile Ala Val Asp Gly Gly Met Ser Asp Asn Ile Arg Pro Ala
330                 335                 340                 345

CTC TAC GGC TCC GAA TAC GAC GCC CGC GTA GTA TCC CGC TTC GCC GAA       3270
Leu Tyr Gly Ser Glu Tyr Asp Ala Arg Val Val Ser Arg Phe Ala Glu
            350                 355                 360

GGA GAC CCA GTA AGC ACC CGC ATC GTG GGC TCC CAC TGC GAA TCC GGC       3318
Gly Asp Pro Val Ser Thr Arg Ile Val Gly Ser His Cys Glu Ser Gly
            365                 370                 375

GAT ATC CTG ATC AAC GAT GAA ATC TAC CCA TCT GAC ATC ACC AGC GGC       3366
Asp Ile Leu Ile Asn Asp Glu Ile Tyr Pro Ser Asp Ile Thr Ser Gly
            380                 385                 390

GAC TTC CTT GCA CTC GCA GCC ACC GGC GCA TAC TGC TAC GCC ATG AGC       3414
Asp Phe Leu Ala Leu Ala Ala Thr Gly Ala Tyr Cys Tyr Ala Met Ser
395                 400                 405

TCC CGC TAC AAC GCC TTC ACA CGG CCC GCC GTC GTG TCC GTC CGC GCT       3462
Ser Arg Tyr Asn Ala Phe Thr Arg Pro Ala Val Val Ser Val Arg Ala
410                 415                 420                 425

GGC AGC TCC CGC CTC ATG CTG CGC CGC GAA ACG CTC GAC GAC ATC CTC       3510
Gly Ser Ser Arg Leu Met Leu Arg Arg Glu Thr Leu Asp Asp Ile Leu
                430                 435                 440

TCA CTA GAG GCA TAACGCTTTT CGACGCCTGA CCCCGCCCTT CACCTTCGCC           3562
Ser Leu Glu Ala
            445
```

GTGGAGGGCG GTTTTGG 3579

(2) INFORMATION FOR SEQ ID NO:19:

(i) SEQUENCE CHARACTERISTICS:
        (A) LENGTH: 550 amino acids
        (B) TYPE: amino acid
        (D) TOPOLOGY: linear (ii) MOLECULE TYPE: protein (xi) SEQUENCE DESCRIPTION: SEQ ID NO: 19:

```
Met Thr Pro Ala Asp Leu Ala Thr Leu Ile Lys Glu Thr Ala Val Glu
 1               5                  10                  15

Val Leu Thr Ser Arg Glu Leu Asp Thr Ser Val Leu Pro Glu Gln Val
                20                  25                  30

Val Val Glu Arg Pro Arg Asn Pro Glu His Gly Asp Tyr Ala Thr Asn
            35                  40                  45

Ile Ala Leu Gln Val Ala Lys Lys Val Gly Gln Asn Pro Arg Asp Leu
        50                  55                  60

Ala Thr Trp Leu Ala Glu Ala Leu Ala Ala Asp Asp Ala Ile Asp Ser
 65                  70                  75                  80

Ala Glu Ile Ala Gly Pro Gly Phe Leu Asn Ile Arg Leu Ala Ala Ala
                85                  90                  95

Ala Gln Gly Glu Ile Val Ala Lys Ile Leu Ala Gln Gly Glu Thr Phe
            100                 105                 110

Gly Asn Ser Asp His Leu Ser His Leu Asp Val Asn Leu Glu Phe Val
        115                 120                 125

Ser Ala Asn Pro Thr Gly Pro Ile His Leu Gly Gly Thr Arg Trp Ala
130                 135                 140

Ala Val Gly Asp Ser Leu Gly Arg Val Leu Glu Ala Ser Gly Ala Lys
145                 150                 155                 160

Val Thr Arg Glu Tyr Tyr Phe Asn Asp His Gly Arg Gln Ile Asp Arg
                165                 170                 175

Phe Ala Leu Ser Leu Leu Ala Ala Lys Gly Glu Pro Thr Pro Glu
            180                 185                 190

Asp Gly Tyr Gly Gly Glu Tyr Ile Lys Glu Ile Ala Glu Ala Ile Val
        195                 200                 205

Glu Lys His Pro Glu Ala Leu Ala Leu Glu Pro Ala Ala Thr Gln Glu
210                 215                 220

Leu Phe Arg Ala Glu Gly Val Glu Met Met Phe Glu His Ile Lys Ser
225                 230                 235                 240

Ser Leu His Glu Phe Gly Thr Asp Phe Asp Val Tyr Tyr His Glu Asn
                245                 250                 255

Ser Leu Phe Glu Ser Gly Ala Val Asp Lys Ala Val Gln Val Leu Lys
            260                 265                 270

Asp Asn Gly Asn Leu Tyr Glu Asn Glu Gly Ala Trp Trp Leu Arg Ser
        275                 280                 285

Thr Glu Phe Gly Asp Asp Lys Asp Arg Val Val Ile Lys Ser Asp Gly
290                 295                 300

Asp Ala Ala Tyr Ile Ala Gly Asp Ile Ala Tyr Val Ala Asp Lys Phe
305                 310                 315                 320

Ser Arg Gly His Asn Leu Asn Ile Tyr Met Leu Gly Ala Asp His His
                325                 330                 335

Gly Tyr Ile Ala Arg Leu Lys Ala Ala Ala Ala Leu Gly Tyr Lys
            340                 345                 350
```

-continued

```
Pro Glu Gly Val Glu Val Leu Ile Gly Gln Met Val Asn Leu Leu Arg
        355                 360                 365

Asp Gly Lys Ala Val Arg Met Ser Lys Arg Ala Gly Thr Val Val Thr
    370                 375                 380

Leu Asp Asp Leu Val Glu Ala Ile Gly Ile Asp Ala Ala Arg Tyr Ser
385                 390                 395                 400

Leu Ile Arg Ser Ser Val Asp Ser Ser Leu Asp Ile Asp Leu Gly Leu
                405                 410                 415

Trp Glu Ser Gln Ser Ser Asp Asn Pro Val Tyr Val Gln Tyr Gly
                420                 425                 430

His Ala Arg Leu Cys Ser Ile Ala Arg Lys Ala Glu Thr Leu Gly Val
                435                 440                 445

Thr Glu Glu Gly Ala Asp Leu Ser Leu Leu Thr His Asp Arg Glu Gly
    450                 455                 460

Asp Leu Ile Arg Thr Leu Gly Glu Phe Pro Ala Val Val Lys Ala Ala
465                 470                 475                 480

Ala Asp Leu Arg Glu Pro His Arg Ile Ala Arg Tyr Ala Glu Glu Leu
                485                 490                 495

Ala Gly Thr Phe His Arg Phe Tyr Asp Ser Cys His Ile Leu Pro Lys
                500                 505                 510

Val Asp Glu Asp Thr Ala Pro Ile His Thr Ala Arg Leu Ala Leu Ala
            515                 520                 525

Ala Ala Thr Arg Gln Thr Leu Ala Asn Ala Leu His Leu Val Gly Val
    530                 535                 540

Ser Ala Pro Glu Lys Met
545                 550

(2) INFORMATION FOR SEQ ID NO:20:

(i) SEQUENCE CHARACTERISTICS:
        (A) LENGTH: 445 amino acids
        (B) TYPE: amino acid
        (D) TOPOLOGY: linear (ii) MOLECULE TYPE: protein (xi) SEQUENCE DESCRIPTION: SEQ ID NO: 20:

Met Ala Thr Val Glu Asn Phe Asn Glu Leu Pro Ala His Val Trp Pro
1               5                   10                  15

Arg Asn Ala Val Arg Gln Glu Asp Gly Val Val Thr Val Ala Gly Val
                20                  25                  30

Pro Leu Pro Asp Leu Ala Glu Glu Tyr Gly Thr Pro Leu Phe Val Val
            35                  40                  45

Asp Glu Asp Asp Phe Arg Ser Arg Cys Arg Asp Met Ala Thr Ala Phe
    50                  55                  60

Gly Gly Pro Gly Asn Val His Tyr Ala Ser Lys Ala Phe Leu Thr Lys
65                  70                  75                  80

Thr Ile Ala Arg Trp Val Asp Glu Gly Leu Ala Leu Asp Ile Ala
                85                  90                  95

Ser Ile Asn Glu Leu Gly Ile Ala Leu Ala Ala Gly Phe Pro Ala Ser
                100                 105                 110

Arg Ile Thr Ala His Gly Asn Asn Lys Gly Val Glu Phe Leu Arg Ala
            115                 120                 125

Leu Val Gln Asn Gly Val Gly His Val Val Leu Asp Ser Ala Gln Glu
    130                 135                 140

Leu Glu Leu Leu Asp Tyr Val Ala Ala Gly Glu Gly Lys Ile Gln Asp
145                 150                 155                 160
```

Val Leu Ile Arg Val Lys Pro Gly Ile Glu Ala His Thr His Glu Phe
            165                 170                 175

Ile Ala Thr Ser His Glu Asp Gln Lys Phe Gly Phe Ser Leu Ala Ser
            180                 185                 190

Gly Ser Ala Phe Glu Ala Ala Lys Ala Ala Asn Asn Ala Glu Asn Leu
            195                 200                 205

Asn Leu Val Gly Leu His Cys His Val Gly Ser Gln Val Phe Asp Ala
            210                 215                 220

Glu Gly Phe Lys Leu Ala Ala Glu Arg Val Leu Gly Leu Tyr Ser Gln
225                 230                 235                 240

Ile His Ser Glu Leu Gly Val Ala Leu Pro Glu Leu Asp Leu Gly Gly
            245                 250                 255

Gly Tyr Gly Ile Ala Tyr Thr Ala Ala Glu Glu Pro Leu Asn Val Ala
            260                 265                 270

Glu Val Ala Ser Asp Leu Leu Thr Ala Val Gly Lys Met Ala Ala Glu
            275                 280                 285

Leu Gly Ile Asp Ala Pro Thr Val Leu Val Glu Pro Gly Arg Ala Ile
            290                 295                 300

Ala Gly Pro Ser Thr Val Thr Ile Tyr Glu Val Gly Thr Thr Lys Asp
305                 310                 315                 320

Val His Val Asp Asp Lys Thr Arg Arg Tyr Ile Ala Val Asp Gly
            325                 330                 335

Gly Met Ser Asp Asn Ile Arg Pro Ala Leu Tyr Gly Ser Glu Tyr Asp
            340                 345                 350

Ala Arg Val Val Ser Arg Phe Ala Glu Gly Asp Pro Val Ser Thr Arg
            355                 360                 365

Ile Val Gly Ser His Cys Glu Ser Gly Asp Ile Leu Ile Asn Asp Glu
            370                 375                 380

Ile Tyr Pro Ser Asp Ile Thr Ser Gly Asp Phe Leu Ala Leu Ala Ala
385                 390                 395                 400

Thr Gly Ala Tyr Cys Tyr Ala Met Ser Ser Arg Tyr Asn Ala Phe Thr
            405                 410                 415

Arg Pro Ala Val Val Ser Val Arg Ala Gly Ser Ser Arg Leu Met Leu
            420                 425                 430

Arg Arg Glu Thr Leu Asp Asp Ile Leu Ser Leu Glu Ala
            435                 440                 445

(2) INFORMATION FOR SEQ ID NO:21:

(i) SEQUENCE CHARACTERISTICS:
        (A) LENGTH: 20 bases
        (B) TYPE: nucleic acid
        (C) STRANDEDNESS: single
        (D) TOPOLOGY: linear (ii) MOLECULE TYPE: other nucleic acid
        (A) DESCRIPTION:   /desc = "synthetic DNA"

(iv) ANTI-SENSE: no (xi) SEQUENCE DESCRIPTION: SEQ ID NO: 21:

AACCTCGTCA TGTTTGAGAA                                                        20

(2) INFORMATION FOR SEQ ID NO:22:

(i) SEQUENCE CHARACTERISTICS:
        (A) LENGTH: 20 bases
        (B) TYPE: nucleic acid (C) STRANDEDNESS: single
(D) TOPOLOGY: linear (ii) MOLECULE TYPE: other nucleic acid
    (A) DESCRIPTION:   /desc = "synthetic DNA"

(iv) ANTI-SENSE: yes (xi) SEQUENCE DESCRIPTION: SEQ ID NO: 22:

```
CCGGCCTACA AAATCGTGCA                                             20
```

(2) INFORMATION FOR SEQ ID NO:23:

(i) SEQUENCE CHARACTERISTICS:
        (A) LENGTH: 1331 bases
        (B) TYPE: nucleic acid
        (C) STRANDEDNESS: double
        (D) TOPOLOGY: linear (ii) MOLECULE TYPE: genomic DNA (vi) ORIGINAL SOURCE:
        (A) ORGANISM: Escherichia coli
        (B) STRAIN: JM109

(ix) FEATURE:
        (A) NAME/KEY: CDS
        (B) LOCATION: 10..1197

(xi) SEQUENCE DESCRIPTION: SEQ ID NO: 23:

```
AACCTCGTC ATG TTT GAG AAC ATT ACC GCC GCT CCT GCC GAC CCG ATT        48
          Met Phe Glu Asn Ile Thr Ala Ala Pro Ala Asp Pro Ile
           1               5                  10

CTG GGC CTG GCC GAT CTG TTT CGT GCC GAT GAA CGT CCC GGC AAA ATT      96
Leu Gly Leu Ala Asp Leu Phe Arg Ala Asp Glu Arg Pro Gly Lys Ile
 15              20                  25

AAC CTC GGG ATT GGT GTC TAT AAA GAT GAG ACG GGC AAA ACC CCG GTA     144
Asn Leu Gly Ile Gly Val Tyr Lys Asp Glu Thr Gly Lys Thr Pro Val
 30              35                  40                  45

CTG ACC AGC GTG AAA AAG GCT GAA CAG TAT CTG CTC GAA AAT GAA ACC     192
Leu Thr Ser Val Lys Lys Ala Glu Gln Tyr Leu Leu Glu Asn Glu Thr
                 50                  55                  60

ACC AAA AAT TAC CTC GGC ATT GAC GGC ATC CCT GAA TTT GGT CGC TGC     240
Thr Lys Asn Tyr Leu Gly Ile Asp Gly Ile Pro Glu Phe Gly Arg Cys
                 65                  70                  75

ACT CAG GAA CTG CTG TTT GGT AAA GGT AGC GCC CTG ATC AAT GAC AAA     288
Thr Gln Glu Leu Leu Phe Gly Lys Gly Ser Ala Leu Ile Asn Asp Lys
         80                  85                  90

CGT GCT CGC ACG GCA CAG ACT CCG GGG GGC ACT GGC GCA CTA CGC GTG     336
Arg Ala Arg Thr Ala Gln Thr Pro Gly Gly Thr Gly Ala Leu Arg Val
         95                 100                 105

GCT GCC GAT TTC CTG GCA AAA AAT ACC AGC GTT AAG CGT GTG TGG GTG     384
Ala Ala Asp Phe Leu Ala Lys Asn Thr Ser Val Lys Arg Val Trp Val
110                 115                 120                 125

AGC AAC CCA AGC TGG CCG AAC CAT AAG AGC GTC TTT AAC TCT GCA GGT     432
Ser Asn Pro Ser Trp Pro Asn His Lys Ser Val Phe Asn Ser Ala Gly
                130                 135                 140

CTG GAA GTT CGT GAA TAC GCT TAT TAT GAT GCG GAA AAT CAC ACT CTT     480
Leu Glu Val Arg Glu Tyr Ala Tyr Tyr Asp Ala Glu Asn His Thr Leu
                145                 150                 155

GAC TTC GAT GCA CTG ATT AAC AGC CTG AAT GAA GCT CAG GCT GGC GAC     528
Asp Phe Asp Ala Leu Ile Asn Ser Leu Asn Glu Ala Gln Ala Gly Asp
                160                 165                 170

GTA GTG CTG TTC CAT GGC TGC TGC CAT AAC CCA ACC GGT ATC GAC CCT     576
Val Val Leu Phe His Gly Cys Cys His Asn Pro Thr Gly Ile Asp Pro
                175                 180                 185
```

```
ACG CTG GAA CAA TGG CAA ACA CTG GCA CAA CTC TCC GTT GAG AAA GGC      624
Thr Leu Glu Gln Trp Gln Thr Leu Ala Gln Leu Ser Val Glu Lys Gly
190                 195                 200                 205

TGG TTA CCG CTG TTT GAC TTC GCT TAC CAG GGT TTT GCC CGT GGT CTG      672
Trp Leu Pro Leu Phe Asp Phe Ala Tyr Gln Gly Phe Ala Arg Gly Leu
                210                 215                 220

GAA GAA GAT GCT GAA GGA CTG CGC GCT TTC GCG GCT ATG CAT AAA GAG      720
Glu Glu Asp Ala Glu Gly Leu Arg Ala Phe Ala Ala Met His Lys Glu
                225                 230                 235

CTG ATT GTT GCC AGT TCC TAC TCT AAA AAC TTT GGC CTG TAC AAC GAG      768
Leu Ile Val Ala Ser Ser Tyr Ser Lys Asn Phe Gly Leu Tyr Asn Glu
                240                 245                 250

CGT GTT GGC GCT TGT ACT CTG GTT GCT GCC GAC AGT GAA ACC GTT GAT      816
Arg Val Gly Ala Cys Thr Leu Val Ala Ala Asp Ser Glu Thr Val Asp
255                 260                 265

CGC GCA TTC AGC CAA ATG AAA GCG GCG ATT CGC GCT AAC TAC TCT AAC      864
Arg Ala Phe Ser Gln Met Lys Ala Ala Ile Arg Ala Asn Tyr Ser Asn
270                 275                 280                 285

CCA CCA GCA CAC GGC GCT TCT GTT GTT GCC ACC ATC CTG AGC AAC GAT      912
Pro Pro Ala His Gly Ala Ser Val Val Ala Thr Ile Leu Ser Asn Asp
                290                 295                 300

GCG TTA CGT GCG ATT TGG GAA CAA GAG CTG ACT GAT ATG CGC CAG CGT      960
Ala Leu Arg Ala Ile Trp Glu Gln Glu Leu Thr Asp Met Arg Gln Arg
                305                 310                 315

ATT CAG CGT ATG CGT CAG TTG TTC GTC AAT ACG CTG CAG GAA AAA GGC     1008
Ile Gln Arg Met Arg Gln Leu Phe Val Asn Thr Leu Gln Glu Lys Gly
                320                 325                 330

GCA AAC CGC GAC TTC AGC TTT ATC ATC AAA CAG AAC GGC ATG TTC TCC     1056
Ala Asn Arg Asp Phe Ser Phe Ile Ile Lys Gln Asn Gly Met Phe Ser
335                 340                 345

TTC AGT GGC CTG ACA AAA GAA CAA GTG CTG CGT CTG CGC GAA GAG TTT     1104
Phe Ser Gly Leu Thr Lys Glu Gln Val Leu Arg Leu Arg Glu Glu Phe
350                 355                 360                 365

GGC GTA TAT GCG GTT GCT TCT GGT CGC GTA AAT GTG GCC GGG ATG ACA     1152
Gly Val Tyr Ala Val Ala Ser Gly Arg Val Asn Val Ala Gly Met Thr
                370                 375                 380

CCA GAT AAC ATG GCT CCG CTG TGC GAA GCG ATT GTG GCA GTG CTG         1197
Pro Asp Asn Met Ala Pro Leu Cys Glu Ala Ile Val Ala Val Leu
                385                 390                 395

TAAGCATTAA AAACAATGAA CGCGCTGAAA AGCGGGCTGA GACTGATGAC AAACGCAACA   1257

TTGCCTGATG CTACGCTTA TCAGGCCTAC GCGTCCCCTG CAATATTTTG AATTTGCACG    1317

ATTTTGTAGG CCGG                                                    1331

(2) INFORMATION FOR SEQ ID NO:24:

(i) SEQUENCE CHARACTERISTICS:
        (A) LENGTH: 396 amino acids
        (B) TYPE: amino acid
        (D) TOPOLOGY: linear (ii) MOLECULE TYPE: protein (xi) SEQUENCE DESCRIPTION: SEQ ID NO: 24:

Met Phe Glu Asn Ile Thr Ala Ala Pro Ala Asp Pro Ile Leu Gly Leu
1               5                   10                  15

Ala Asp Leu Phe Arg Ala Asp Glu Arg Pro Gly Lys Ile Asn Leu Gly
                20                  25                  30

Ile Gly Val Tyr Lys Asp Glu Thr Gly Lys Thr Pro Val Leu Thr Ser
            35                  40                  45
```

```
Val Lys Lys Ala Glu Gln Tyr Leu Leu Glu Asn Glu Thr Thr Lys Asn
 50                  55                  60

Tyr Leu Gly Ile Asp Gly Ile Pro Glu Phe Gly Arg Cys Thr Gln Glu
 65                  70                  75                  80

Leu Leu Phe Gly Lys Gly Ser Ala Leu Ile Asn Asp Lys Arg Ala Arg
                 85                  90                  95

Thr Ala Gln Thr Pro Gly Gly Thr Gly Ala Leu Arg Val Ala Ala Asp
                100                 105                 110

Phe Leu Ala Lys Asn Thr Ser Val Lys Arg Val Trp Val Ser Asn Pro
            115                 120                 125

Ser Trp Pro Asn His Lys Ser Val Phe Asn Ser Ala Gly Leu Glu Val
            130                 135                 140

Arg Glu Tyr Ala Tyr Tyr Asp Ala Glu Asn His Thr Leu Asp Phe Asp
145                 150                 155                 160

Ala Leu Ile Asn Ser Leu Asn Glu Ala Gln Ala Gly Asp Val Val Leu
                165                 170                 175

Phe His Gly Cys Cys His Asn Pro Thr Gly Ile Asp Pro Thr Leu Glu
                180                 185                 190

Gln Trp Gln Thr Leu Ala Gln Leu Ser Val Glu Lys Gly Trp Leu Pro
            195                 200                 205

Leu Phe Asp Phe Ala Tyr Gln Gly Phe Ala Arg Gly Leu Glu Glu Asp
210                 215                 220

Ala Glu Gly Leu Arg Ala Phe Ala Ala Met His Lys Glu Leu Ile Val
225                 230                 235                 240

Ala Ser Ser Tyr Ser Lys Asn Phe Gly Leu Tyr Asn Glu Arg Val Gly
                245                 250                 255

Ala Cys Thr Leu Val Ala Ala Asp Ser Glu Thr Val Asp Arg Ala Phe
                260                 265                 270

Ser Gln Met Lys Ala Ala Ile Arg Ala Asn Tyr Ser Asn Pro Pro Ala
            275                 280                 285

His Gly Ala Ser Val Val Ala Thr Ile Leu Ser Asn Asp Ala Leu Arg
            290                 295                 300

Ala Ile Trp Glu Gln Glu Leu Thr Asp Met Arg Gln Arg Ile Gln Arg
305                 310                 315                 320

Met Arg Gln Leu Phe Val Asn Thr Leu Gln Glu Lys Gly Ala Asn Arg
                325                 330                 335

Asp Phe Ser Phe Ile Ile Lys Gln Asn Gly Met Phe Ser Phe Ser Gly
                340                 345                 350

Leu Thr Lys Glu Gln Val Leu Arg Leu Arg Glu Glu Phe Gly Val Tyr
            355                 360                 365

Ala Val Ala Ser Gly Arg Val Asn Val Ala Gly Met Thr Pro Asp Asn
            370                 375                 380

Met Ala Pro Leu Cys Glu Ala Ile Val Ala Val Leu
385                 390                 395
```

(2) INFORMATION FOR SEQ ID NO:25:

(i) SEQUENCE CHARACTERISTICS:
        (A) LENGTH: 2517 bases
        (B) TYPE: nucleic acid
        (C) STRANDEDNESS: double
        (D) TOPOLOGY: linear (ii) MOLECULE TYPE: genomic DNA (vi) ORIGINAL SOURCE:
        (A) ORGANISM: Brevibacterium lactofermentum
        (B) STRAIN: ATCC 13869

(xi) SEQUENCE DESCRIPTION: SEQ ID NO: 25:

```
GATCAGCTTC GGGTGTTGAA GGGGCCGAAT AAGGAACTCG CGCAGTTGGG TCGTAGTTTG      60
TTTAAACGAC TTGGTGATGT GTTGGCGTAT TTCGATGTTG GTGTCTCCAA CGGTCCGGTC     120
GAAGCGATCA ACGGACGGTT GGAGCATTTG CGTGGGATTG CTCTAGGTTT CCGTAATTTG     180
AACCACTACA TTCTGCGGTG CCTTATCCAT TCAGGGCAGT TGGTCCATAA GATCAATGCA     240
CTCTAAAACA GGAAGAGCCC CTTTACAAGC GGCAAGACCA AACTGGGTGA CCGAAAATCT     300
TCAGGCCAAT CAGTTTTGGT CATATGGGAT GGTTTTTAGA CCTCGAAACC ATCCCATATG     360
ACCGAAGCCC GCGAAACTCT GTGTTCGTTG GTCGCCTGGT TCGGTCTCAA TGCCTTGCCG     420
AAACCACAAC GCCCCGAAAC CCAAAACTCC CCAATACATG AAAAAACCAG CTTCCCACCG     480
AAGTGAGAAG CTGGTTTAGT TTGCGGAGGA TAGGGGATTT GAACCCCTGA GGGATTGCTC     540
CCAACCCGCG TTCCAGGCGA GCGACATAGG CCGCTAGTCG AATCCTCCAG CTAGAACGGC     600
TGCAACGCAT GGCTGCTTTG TTCTGGGGAT TAGATTACAC AAAAGTCGTT TAGAAACTCA     660
AATCCGCTCG CAGTTGGCGT TTTCTGGGGC GGTTCAGCTA GAGTTATGCG AAGGATCCCG     720
TGCGGCGTTT ATCTTGTGAA CTCCCCCAGG GCAGGAATGC AGCAAGGGTC AGCGAGCTCT     780
GACGGGTGCG CGGGGTCCCC TAAAACGTCT AGAGTAGTGG CTTGAGGTCA CTGCTCTTTT     840
TTTGTGCCCT TTTTTTGGTC CGTCTATTTT GCCACCACAT GCGGAGGTAC GCAGTTATGA     900
GTTCAGTTTC GCTGCAGGAT TTTGATGCAG AGCGAATTGG TCTGTTCCAC GAGGACATTA     960
AACGCAAGTT TGATGAGCTC AAGTCAAAAA ATCTGAAGCT GGATCTTACT CGCGGTAAGC    1020
CTTCGTCGGA GCAGTTGGAT TTCGCTGATG AGCTGTTGGC GTTGCCTGGT AAGGGCGATT    1080
TCAAGGCTGC GGATGGTACT GATGTCCGTA ACTATGGCGG GCTGGATGGC ATTGTTGATA    1140
TTCGTCAGAT TTGGGCGGAT TTGCTGGGTG TTCCTGTGGA GCAGGTGCTG GCGGGGGATG    1200
CTTCGAGCTT GAACATCATG TTTGATGTGA TCAGCTGGTC GTACATTTTT GGTAACAATG    1260
ATTCGGTTCA GCCTTGGTCG AAGGAAGAAA CTGTTAAGTG GATTTGTCCT GTTCCGGGAT    1320
ATGATCGCCA TTTCTCCATC ACGGAGCGTT TCGGCTTTGA GATGATTTCT GTGCCAATGA    1380
ATGAAGACGG CCCTGATATG GATGCTGTTG AGGAATTGGT CAAGGATCCG CAGGTTAAGG    1440
GCATGTGGGT TGTGCCGGTA TTTTCTAACC CGACTGGTTT CACGGTGTCG GAGGACGTCG    1500
CAAAGCGTCT GAGCACGATG GAAACTGCGG CGCCGGACTT CCGCGTGGTG TGGGATAACG    1560
CTTACGCCGT TCATACTCTG ACCGATGAGT TCCCTGAGGT CATCGACATC GTTGGGCTTG    1620
GTGAGGCGGC GGGTAACCCG AACCGTTTCT GGGCGTTCAC TTCTACTTCG AAGATCACTC    1680
TCGCGGGTGC GGGCGTGTCC TTCTTCATGA CTTCTGCGGA GAACCGTAAG TGGTACTCCG    1740
GTCATGCGGG TATCCGTGGC ATTGGCCCTA ACAAGGTCAA TCAGTTGGCT CATGCGCGTT    1800
ACTTTGGCGA TGCTGAGGGA GTGCGCGCGG TGATGCGTAA GCATGCTGCG TCGTTGGCTC    1860
CGAAGTTCAA CAAGGTTCTG GAGATCCTGG ATTCTCGCCT TGCTGAGTAC GGTGTCGCGC    1920
AGTGGACTGT CCCTGCGGGC GGTTACTTCA TTTCCCTTGA TGTGGTTCCT GGTACGGCAT    1980
CTCGTGTGGC TGAGTTGGCT AAGGAAGCCG GCATTGCGTT GACGGGTGCG GGTTCTTCTT    2040
ACCCGCTGCG TCAGGATCCG GAGAACAAGA ACCTCCGTTT GGCGCCTTCT CTGCCTCCTG    2100
TTGAGGAACT TGAGGTTGCC ATGGATGGCG TGGCTACGTG TGTTTTGCTG GCAGCTGCGG    2160
AGCACTACGC TAGCTAGAGT GAATACCGCG GAAACTGCAC ATTGGATTAA CCGTTTGCTG    2220
CCGGGTCAGC CGGAGTTTCA CCAGGTTGGC GCGTTTAAAG TGGCGGGTTA CACGCTTGAT    2280
GATGAGTCAA TTGCGTGTTC TGTCAATTTC GGGCGCGTCA ACACGGGCCT GGTCACCGAG    2340
```

```
ACAGGCGCGG AAACCGTCGA TGTGCGAAGT GAGATTTTGA GCCTGGCCAG GGCCGACGTG   2400

TCCGTGCCTG GGCGCGCCGT CGGCGCTGCT GCAACAATGC TTCTCGACGC CTCCCTCTCC   2460

TTCAAATCCG CCACCGATTC CAGTGTCACT CCCATGCATG CCCAACCGGG ACAGATC      2517
```

(2) INFORMATION FOR SEQ ID NO:26:

(i) SEQUENCE CHARACTERISTICS:
        (A) LENGTH: 23 bases
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic DNA"

(iv) ANTI-SENSE: no (xi) SEQUENCE DESCRIPTION: SEQ ID NO: 26:

```
GATCAACGGA CGGTTGGAGC ATT                                             23
```

(2) INFORMATION FOR SEQ ID NO:27:

(i) SEQUENCE CHARACTERISTICS:
        (A) LENGTH: 23 bases
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic DNA"

(iv) ANTI-SENSE: yes (xi) SEQUENCE DESCRIPTION: SEQ ID NO: 27:

```
GGTATTCACT CTAGCTAGCG TAG                                             23
```

(2) INFORMATION FOR SEQ ID NO:28:

(i) SEQUENCE CHARACTERISTICS:
        (A) LENGTH: 23 bases
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic DNA"

(iv) ANTI-SENSE: no (xi) SEQUENCE DESCRIPTION: SEQ ID NO: 28:

```
GAGCTCAAGT CAAAAAATCT GAA                                             23
```

(2) INFORMATION FOR SEQ ID NO:29:

(i) SEQUENCE CHARACTERISTICS:
        (A) LENGTH: 23 bases
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic DNA"

(iv) ANTI-SENSE: yes (xi) SEQUENCE DESCRIPTION: SEQ ID NO: 29:

```
GATCTGTCCC GGTTGGGCAT GCA                                             23
```

(2) INFORMATION FOR SEQ ID NO:30:

(i) SEQUENCE CHARACTERISTICS:
        (A) LENGTH: 2517 bases
        (B) TYPE: nucleic acid
        (C) STRANDEDNESS: double
        (D) TOPOLOGY: linear (ii) MOLECULE TYPE: genomic DNA (vi) ORIGINAL SOURCE:
        (A) ORGANISM: Brevibacterium lactofermentum
        (B) STRAIN: ATCC 13869

(ix) FEATURE:
        (A) NAME/KEY: CDS
        (B) LOCATION: 879..2174

(xi) SEQUENCE DESCRIPTION: SEQ ID NO: 30:

```
GATCAGCTTC GGGTGTTGAA GGGGCCGAAT AAGGAACTCG CGCAGTTGGG TCGTAGTTTG      60

TTTAAACGAC TTGGTGATGT GTTGGCGTAT TTCGATGTTG GTGTCTCCAA CGGTCCGGTC     120

GAAGCGATCA ACGGACGGTT GGAGCATTTG CGTGGGATTG CTCTAGGTTT CCGTAATTTG     180

AACCACTACA TTCTGCGGTG CCTTATCCAT TCAGGGCAGT TGGTCCATAA GATCAATGCA     240

CTCTAAAACA GGAAGAGCCC CTTTACAAGC GGCAAGACCA AACTGGGTGA CCGAAAATCT     300

TCAGGCCAAT CAGTTTTGGT CATATGGGAT GGTTTTTAGA CCTCGAAACC ATCCCATATG     360

ACCGAAGCCC GCGAAACTCT GTGTTCGTTG GTCGCCTGGT TCGGTCTCAA TGCCTTGCCG     420

AAACCACAAC GCCCCGAAAC CCAAAACTCC CCAATACATG AAAAAACCAG CTTCCCACCG     480

AAGTGAGAAG CTGGTTTAGT TTGCGGAGGA TAGGGGATTT GAACCCCTGA GGGATTGCTC     540

CCAACCCGCG TTCAGGCGA GCGACATAGG CCGCTAGTCG AATCCTCCAG CTAGAACGGC      600

TGCAACGCAT GGCTGCTTTG TTCTGGGGAT TAGATTACAC AAAAGTCGTT TAGAAACTCA     660

AATCCGCTCG CAGTTGGCGT TTTCTGGGGC GGTTCAGCTA GAGTTATGCG AAGGATCCCG     720

TGCGGCGTTT ATCTTGTGAA CTCCCCCAGG GCAGGAATGC AGCAAGGGTC AGCGAGCTCT     780

GACGGGTGCG CGGGGTCCCC TAAAACGTCT AGAGTAGTGG CTTGAGGTCA CTGCTCTTTT     840

TTTGTGCCCT TTTTTTGGTC CGTCTATTTT GCCACCAC ATG CGG AGG TAC GCA         893
                                         Met Arg Arg Tyr Ala
                                           1               5

GTT ATG AGT TCA GTT TCG CTG CAG GAT TTT GAT GCA GAG CGA ATT GGT      941
Val Met Ser Ser Val Ser Leu Gln Asp Phe Asp Ala Glu Arg Ile Gly
              10                  15                  20

CTG TTC CAC GAG GAC ATT AAA CGC AAG TTT GAT GAG CTC AAG TCA AAA      989
Leu Phe His Glu Asp Ile Lys Arg Lys Phe Asp Glu Leu Lys Ser Lys
                  25                  30                  35

AAT CTG AAG CTG GAT CTT ACT CGC GGT AAG CCT TCG TCG GAG CAG TTG     1037
Asn Leu Lys Leu Asp Leu Thr Arg Gly Lys Pro Ser Ser Glu Gln Leu
          40                  45                  50

GAT TTC GCT GAT GAG CTG TTG GCG TTG CCT GGT AAG GGC GAT TTC AAG     1085
Asp Phe Ala Asp Glu Leu Leu Ala Leu Pro Gly Lys Gly Asp Phe Lys
      55                  60                  65

GCT GCG GAT GGT ACT GAT GTC CGT AAC TAT GGC GGG CTG GAT GGC ATT     1133
Ala Ala Asp Gly Thr Asp Val Arg Asn Tyr Gly Gly Leu Asp Gly Ile
 70                  75                  80                  85

GTT GAT ATT CGT CAG ATT TGG GCG GAT TTG CTG GGT GTT CCT GTG GAG     1181
Val Asp Ile Arg Gln Ile Trp Ala Asp Leu Leu Gly Val Pro Val Glu
                  90                  95                 100

CAG GTG CTG GCG GGG GAT GCT TCG AGC TTG AAC ATC ATG TTT GAT GTG     1229
Gln Val Leu Ala Gly Asp Ala Ser Ser Leu Asn Ile Met Phe Asp Val
             105                 110                 115
```

| | | |
|---|---|---|
| ATC AGC TGG TCG TAC ATT TTT GGT AAC AAT GAT TCG GTT CAG CCT TGG<br>Ile Ser Trp Ser Tyr Ile Phe Gly Asn Asn Asp Ser Val Gln Pro Trp<br>120                       125                       130 | 1277 |
| TCG AAG GAA GAA ACT GTT AAG TGG ATT TGT CCT GTT CCG GGA TAT GAT<br>Ser Lys Glu Glu Thr Val Lys Trp Ile Cys Pro Val Pro Gly Tyr Asp<br>    135                     140                     145 | 1325 |
| CGC CAT TTC TCC ATC ACG GAG CGT TTC GGC TTT GAG ATG ATT TCT GTG<br>Arg His Phe Ser Ile Thr Glu Arg Phe Gly Phe Glu Met Ile Ser Val<br>150                       155                     160               165 | 1373 |
| CCA ATG AAT GAA GAC GGC CCT GAT ATG GAT GCT GTT GAG GAA TTG GTC<br>Pro Met Asn Glu Asp Gly Pro Asp Met Asp Ala Val Glu Glu Leu Val<br>            170                     175                     180 | 1421 |
| AAG GAT CCG CAG GTT AAG GGC ATG TGG GTT GTG CCG GTA TTT TCT AAC<br>Lys Asp Pro Gln Val Lys Gly Met Trp Val Val Pro Val Phe Ser Asn<br>                185                     190                     195 | 1469 |
| CCG ACT GGT TTC ACG GTG TCG GAG GAC GTC GCA AAG CGT CTG AGC ACG<br>Pro Thr Gly Phe Thr Val Ser Glu Asp Val Ala Lys Arg Leu Ser Thr<br>200                       205                     210 | 1517 |
| ATG GAA ACT GCG GCG CCG GAC TTC CGC GTG GTG TGG GAT AAC GCT TAC<br>Met Glu Thr Ala Ala Pro Asp Phe Arg Val Val Trp Asp Asn Ala Tyr<br>    215                     220                     225 | 1565 |
| GCC GTT CAT ACT CTG ACC GAT GAG TTC CCT GAG GTC ATC GAC ATC GTT<br>Ala Val His Thr Leu Thr Asp Glu Phe Pro Glu Val Ile Asp Ile Val<br>230                       235                     240               245 | 1613 |
| GGG CTT GGT GAG GCG GCG GGT AAC CCG AAC CGT TTC TGG GCG TTC ACT<br>Gly Leu Gly Glu Ala Ala Gly Asn Pro Asn Arg Phe Trp Ala Phe Thr<br>            250                     255                     260 | 1661 |
| TCT ACT TCG AAG ATC ACT CTC GCG GGT GCG GGC GTG TCC TTC TTC ATG<br>Ser Thr Ser Lys Ile Thr Leu Ala Gly Ala Gly Val Ser Phe Phe Met<br>                265                     270                     275 | 1709 |
| ACT TCT GCG GAG AAC CGT AAG TGG TAC TCC GGT CAT GCG GGT ATC CGT<br>Thr Ser Ala Glu Asn Arg Lys Trp Tyr Ser Gly His Ala Gly Ile Arg<br>280                       285                     290 | 1757 |
| GGC ATT GGC CCT AAC AAG GTC AAT CAG TTG GCT CAT GCG CGT TAC TTT<br>Gly Ile Gly Pro Asn Lys Val Asn Gln Leu Ala His Ala Arg Tyr Phe<br>    295                     300                     305 | 1805 |
| GGC GAT GCT GAG GGA GTG CGC GCG GTG ATG CGT AAG CAT GCT GCG TCG<br>Gly Asp Ala Glu Gly Val Arg Ala Val Met Arg Lys His Ala Ala Ser<br>310                       315                     320               325 | 1853 |
| TTG GCT CCG AAG TTC AAC AAG GTT CTG GAG ATC CTG GAT TCT CGC CTT<br>Leu Ala Pro Lys Phe Asn Lys Val Leu Glu Ile Leu Asp Ser Arg Leu<br>            330                     335                     340 | 1901 |
| GCT GAG TAC GGT GTC GCG CAG TGG ACT GTC CCT GCG GGC GGT TAC TTC<br>Ala Glu Tyr Gly Val Ala Gln Trp Thr Val Pro Ala Gly Gly Tyr Phe<br>                345                     350                     355 | 1949 |
| ATT TCC CTT GAT GTG GTT CCT GGT ACG GCA TCT CGT GTG GCT GAG TTG<br>Ile Ser Leu Asp Val Val Pro Gly Thr Ala Ser Arg Val Ala Glu Leu<br>                   360                     365                     370 | 1997 |
| GCT AAG GAA GCC GGC ATT GCG TTG ACG GGT GCG GGT TCT TCT TAC CCG<br>Ala Lys Glu Ala Gly Ile Ala Leu Thr Gly Ala Gly Ser Ser Tyr Pro<br>375                       380                     385 | 2045 |
| CTG CGT CAG GAT CCG GAG AAC AAG AAC CTC CGT TTG GCG CCT TCT CTG<br>Leu Arg Gln Asp Pro Glu Asn Lys Asn Leu Arg Leu Ala Pro Ser Leu<br>390                       395                     400               405 | 2093 |
| CCT CCT GTT GAG GAA CTT GAG GTT GCC ATG GAT GGC GTG GCT ACG TGT<br>Pro Pro Val Glu Glu Leu Glu Val Ala Met Asp Gly Val Ala Thr Cys<br>            410                     415                     420 | 2141 |
| GTT TTG CTG GCA GCT GCG GAG CAC TAC GCT AGC TAGAGTGAAT ACCGCGGAAA<br>Val Leu Leu Ala Ala Ala Glu His Tyr Ala Ser<br>                425                     430 | 2194 |

```
CTGCACATTG GATTAACCGT TTGCTGCCGG GTCAGCCGGA GTTTCACCAG GTTGGCGCGT    2254

TTAAAGTGGC GGGTTACACG CTTGATGATG AGTCAATTGC GTGTTCTGTC AATTTCGGGC    2314

GCGTCAACAC GGGCCTGGTC ACCGAGACAG GCGCGGAAAC CGTCGATGTG CGAAGTGAGA    2374

TTTTGAGCCT GGCCAGGGCC GACGTGTCCG TGCCTGGGCG CGCCGTCGGC GCTGCTGCAA    2434

CAATGCTTCT CGACGCCTCC CTCTCCTTCA AATCCGCCAC CGATTCCAGT GTCACTCCCA    2494

TGCATGCCCA ACCGGGACAG ATC                                          2517
```

(2) INFORMATION FOR SEQ ID NO:31:

(i) SEQUENCE CHARACTERISTICS:
        (A) LENGTH: 432 amino acids
        (B) TYPE: amino acid
        (D) TOPOLOGY: linear (ii) MOLECULE TYPE: protein (xi) SEQUENCE DESCRIPTION: SEQ ID NO: 31:

```
Met Arg Arg Tyr Ala Val Met Ser Ser Val Ser Leu Gln Asp Phe Asp
 1               5                  10                  15

Ala Glu Arg Ile Gly Leu Phe His Glu Asp Ile Lys Arg Lys Phe Asp
                20                  25                  30

Glu Leu Lys Ser Lys Asn Leu Lys Leu Asp Leu Thr Arg Gly Lys Pro
            35                  40                  45

Ser Ser Glu Gln Leu Asp Phe Ala Asp Glu Leu Leu Ala Leu Pro Gly
        50                  55                  60

Lys Gly Asp Phe Lys Ala Ala Asp Gly Thr Asp Val Arg Asn Tyr Gly
 65                  70                  75                  80

Gly Leu Asp Gly Ile Val Asp Ile Arg Gln Ile Trp Ala Asp Leu Leu
                85                  90                  95

Gly Val Pro Val Glu Gln Val Leu Ala Gly Asp Ala Ser Ser Leu Asn
               100                 105                 110

Ile Met Phe Asp Val Ile Ser Trp Ser Tyr Ile Phe Gly Asn Asn Asp
            115                 120                 125

Ser Val Gln Pro Trp Ser Lys Glu Glu Thr Val Lys Trp Ile Cys Pro
        130                 135                 140

Val Pro Gly Tyr Asp Arg His Phe Ser Ile Thr Glu Arg Phe Gly Phe
145                 150                 155                 160

Glu Met Ile Ser Val Pro Met Asn Glu Asp Gly Pro Asp Met Asp Ala
                165                 170                 175

Val Glu Glu Leu Val Lys Asp Pro Gln Val Lys Gly Met Trp Val Val
            180                 185                 190

Pro Val Phe Ser Asn Pro Thr Gly Phe Thr Val Ser Glu Asp Val Ala
        195                 200                 205

Lys Arg Leu Ser Thr Met Glu Thr Ala Ala Pro Asp Phe Arg Val Val
    210                 215                 220

Trp Asp Asn Ala Tyr Ala Val His Thr Leu Thr Asp Glu Phe Pro Glu
225                 230                 235                 240

Val Ile Asp Ile Val Gly Leu Gly Glu Ala Ala Gly Asn Pro Asn Arg
                245                 250                 255

Phe Trp Ala Phe Thr Ser Thr Ser Lys Ile Thr Leu Ala Gly Ala Gly
            260                 265                 270

Val Ser Phe Phe Met Thr Ser Ala Glu Asn Arg Lys Trp Tyr Ser Gly
        275                 280                 285

His Ala Gly Ile Arg Gly Ile Gly Pro Asn Lys Val Asn Gln Leu Ala
    290                 295                 300
```

-continued

```
His Ala Arg Tyr Phe Gly Asp Ala Glu Gly Val Arg Ala Val Met Arg
305                 310                 315                 320

Lys His Ala Ala Ser Leu Ala Pro Lys Phe Asn Lys Val Leu Glu Ile
            325                 330                 335

Leu Asp Ser Arg Leu Ala Glu Tyr Gly Val Ala Gln Trp Thr Val Pro
                340                 345                 350

Ala Gly Gly Tyr Phe Ile Ser Leu Asp Val Val Pro Gly Thr Ala Ser
        355                 360                 365

Arg Val Ala Glu Leu Ala Lys Glu Ala Gly Ile Ala Leu Thr Gly Ala
    370                 375                 380

Gly Ser Ser Tyr Pro Leu Arg Gln Asp Pro Glu Asn Lys Asn Leu Arg
385                 390                 395                 400

Leu Ala Pro Ser Leu Pro Pro Val Glu Glu Leu Glu Val Ala Met Asp
            405                 410                 415

Gly Val Ala Thr Cys Val Leu Leu Ala Ala Ala Glu His Tyr Ala Ser
            420                 425                 430
```